US006762170B1

(12) United States Patent
Chan et al.

(10) Patent No.: US 6,762,170 B1
(45) Date of Patent: Jul. 13, 2004

(54) 2-(PURIN-9-YL)-TETRAHYDROFURAN-3,4-DIOL DERIVATIVES

(75) Inventors: Chuen Chan, Hertfordshire (GB); Richard Charles Peter Cousins, Hertfordshire (GB); Brian Cox, Hertfordshire (GB)

(73) Assignee: SmithKlineBeecham Corporation, Philadelphia, PA (US)

( * ) Notice: Subject to any disclaimer, the term of this patent is extended or adjusted under 35 U.S.C. 154(b) by 0 days.

(21) Appl. No.: 09/601,301

(22) PCT Filed: Jan. 29, 1999

(86) PCT No.: PCT/EP99/00503

§ 371 (c)(1),
(2), (4) Date: Jul. 31, 2000

(87) PCT Pub. No.: WO99/38877

PCT Pub. Date: Aug. 5, 1999

(30) Foreign Application Priority Data

Jan. 31, 1998 (GB) .............................................. 9802066
Jun. 23, 1998 (GB) .............................................. 9813528

(51) Int. Cl.$^7$ ..................... A01N 43/04; A61K 31/70; C07H 19/00; C07H 19/16

(52) U.S. Cl. ......................... 514/45; 514/46; 514/47; 514/48; 514/851; 514/885; 514/925; 536/27.13; 536/27.21; 536/27.23; 536/27.81; 544/251; 544/264

(58) Field of Search ..................... 514/45, 826, 851, 514/885, 925, 263.2; 536/27.13, 27.81; 544/251, 264

(56) References Cited

U.S. PATENT DOCUMENTS

| | | |
|---|---|---|
| 3,796,700 A | 3/1974 | Yoshioka et al. |
| 3,864,483 A | 2/1975 | Stein et al. |
| 3,966,917 A | 6/1976 | Prasad et al. |
| 3,983,104 A | 9/1976 | Vorbruggen |
| 4,146,715 A | 3/1979 | Schaeffer et al. ........... 544/276 |
| 4,167,565 A | 9/1979 | Stein et al. |
| 4,224,438 A | 9/1980 | Fauland et al. |
| 4,663,313 A | 5/1987 | Bristol et al. |
| 4,704,381 A | 11/1987 | Schaumann et al. |
| 4,767,747 A | 8/1988 | Hamilton et al. |
| 4,855,288 A | 8/1989 | Gadient et al. |
| 4,962,194 A | 10/1990 | Bridges |
| 4,968,697 A | 11/1990 | Hutchison |
| 4,985,409 A | 1/1991 | Yamada et al. |
| 5,021,574 A | 6/1991 | Hajos et al. ................. 544/276 |
| 5,023,244 A | 6/1991 | Goto et al. |
| 5,043,325 A | 8/1991 | Olsson et al. |
| 5,106,837 A | 4/1992 | Carson et al. |
| 5,219,839 A | 6/1993 | Bru-Magniez et al. |
| 5,219,840 A | 6/1993 | Gadient et al. |
| 5,258,380 A | 11/1993 | Janssens et al. ......... 514/233.2 |
| 5,280,015 A | 1/1994 | Jacobson et al. |
| 5,364,862 A | 11/1994 | Spada et al. |
| 5,424,297 A | 6/1995 | Rubio et al. |

| | | |
|---|---|---|
| 6,426,337 B1 | 7/2002 | Cox et al. |
| 6,495,528 B1 | 12/2002 | Allen et al. |
| 6,528,494 B2 | 3/2003 | Cox et al. |
| 6,534,486 B1 | 3/2003 | Allen et al. |
| 6,610,665 B1 * | 8/2003 | Bays et al. .................... 514/46 |

FOREIGN PATENT DOCUMENTS

| | | |
|---|---|---|
| BE | 768925 | 6/1971 |
| DE | 2034785 | 1/1972 |
| DE | 2213180 | 9/1972 |
| DE | 2317770 | 10/1973 |
| DE | 26 21 470 A | 12/1997 |
| EP | 0066918 A1 | 12/1982 |
| EP | 0139358 A2 | 5/1985 |
| EP | 0161128 A1 | 11/1985 |
| EP | 0181129 A2 | 5/1986 |
| EP | 0222330 A2 | 5/1987 |
| EP | 0232813 A2 | 8/1987 |
| EP | 0 253 962 | 1/1988 |
| EP | 0 277 917 A | 8/1988 |
| EP | 0 417 999 A1 | 3/1991 |
| EP | 0423776 A2 | 4/1991 |
| EP | 0423777 A2 | 4/1991 |
| EP | 0 434 450 A2 | 6/1991 |
| GB | 1386 656 | 3/1975 |
| GB | 1399 670 | 7/1975 |
| GB | 2199036 A | 6/1988 |
| GB | 2203149 A | 10/1998 |
| JP | 58-167599 | 10/1983 |
| JP | 58-174322 | 10/1983 |
| WO | WO 86 00310 A | 1/1986 |
| WO | 88/03147 | 5/1988 |
| WO | 88/03148 | 5/1988 |
| WO | 91/13082 | 9/1991 |
| WO | 92/05177 | 4/1992 |
| WO | 92/20696 | 11/1992 |
| WO | 99/38877 A | 8/1999 |
| WO | 99/41267 A | 8/1999 |

(List continued on next page.)

OTHER PUBLICATIONS

W. Jahn, et. al., "Synthese 5'–substitutierter Adenosinderivate," *Chemische Berichte*, vol. 98, No. 6, 1965, pp. 1705–1708.

A. Rosowsky, et. al., "Synthesis of the 2–Chloro Analogs of 3'–deoxyadenosine,2',3'–Deoxyadenosine, and 2–40 ,3'–didehydro–2',3'–deoxyadenosine as Potential Antiviral Agents," *Journal of Medicinal Chemistry*, vol. 32, No. 5, May 1989, pp. 1135–1140.

K. Isono, et. al., "Ascamycin and Dealanylascamycin, Nucleoside Antibiotics from Streptomyces sp." *Journal of Antibiotics*, vol. XXXVIII, No. 6, May 1984, pp. 670–672.

(List continued on next page.)

*Primary Examiner*—James O. Wilson
*Assistant Examiner*—Traviss C. McIntosh, III
(74) *Attorney, Agent, or Firm*—J. Michael Strickland

(57) ABSTRACT

There are provided according to the invention, novel compounds of formula (I) wherein $R^1$, $R^2$ and $R^3$ are as described in the specification, processes for preparing them, formulations containing them and their use in therapy for the treatment of inflammatory disease.

36 Claims, No Drawings

FOREIGN PATENT DOCUMENTS

| WO | 93/14102 | 7/1993 |
|---|---|---|
| WO | 93/22328 | 11/1993 |
| WO | 94/02497 | 2/1994 |
| WO | 94/17090 A | 8/1994 |
| WO | 94/18215 | 8/1994 |
| WO | 95/02604 | 1/1995 |
| WO | 95/11904 | 5/1995 |
| WO | 95/18817 | 7/1995 |
| WO | 96/02543 A1 | 2/1996 |
| WO | WO 96 02553 | 2/1996 |
| WO | 98/01426 | 1/1998 |
| WO | WO 98 01459 | 1/1998 |
| WO | 98/16539 | 4/1998 |
| WO | 98/28316 A | 7/1998 |

OTHER PUBLICATIONS

Chiara Dianzani, et. al., "Adenosine modulation of primed human neutrophils," *European Journal of Pharmacology* 263 (1994) pp, 223–226.

Keith R.F. Elliott, et. al., "Interactions of formylemethionyl–leucyl–phenylalanine, adenoise, and phosphodiesterase inhibitors in human monocytes," *Feb 07518–FEBS Letters*, vol. 254, No 1,2, pp. 94–98, Aug. 1989.

Thomas H. Burkey, et. al., "Adenosine inhibits fMLP––stimulated adherence and superoxide anion generation by human neutrophils at an early step in signal transduction," *Biochimica et Biophysica Acta*, 1175 (1993) pp. 312–318.

Peter T. Peachell, et. al., "Inhibition by Andenosine of Histamine and Leukotriene Release from Human Basophils," *Biochemical Pharmacology*, vol. 38, No 11, pp. 1717–1725, 1989.

Yutaka Kohno, et. al., "Activation of A3, Adenosine Receptors of Human Eosinophils Elevates Intracellular Calcium," *Blook*, vol. 88, No. 9 (Nov. 1), 1996: pp. 3569–3574.

Erno A. Van Schaick, et. al., "Hemodynamic effects and histamine release elicited by the selective adenosine A3 receptor agonist 2–Cl–IB–MECA in conscious rats," *European Journal of Pharmacology 308*, (1996) pp. 311–314.

Hiroshi Asako, et. al., "Leukocyte Adherence in Rate Mesenteric Venules: Effects of Adenosine and Methotrexate," *Gastroenterology* 1993; 104: pp. 31–37.

Rochelle Hirschborn, "Overview of Biochemical Abnormalities and Molecular Genetics of Adenosine Deaminase Deficiency," *Pediatric Research, Copyright © 1992 International Pediatric Research Foundation, Inc.*, vol. 33 (Suppl.), No. 1, 1993, pp. S35–S41.

Sanna Rosengren, et. al., "Anti–Inflammatory Effects of an Adenosine Kinase Inhibitor," *The Journal of Immunology*, 1995, 154: pp. 5444–5451.

Paul G. Green, et. al., "Purinergic regulation of bradykinin––induced plasma extravasation ad adjuvant–induced arthritis in the rat," *Proc. Natl. Aca. Sci. USA*, vol. 88, pp. 4162–4165, May 1991.

Bruce N. Cronstein, et. al., "the antiinflammatory Mechanism of Methotrexate," *J. Clin. Invest. ©The American Society for Clinical Investigation, Inc.*, vol. 92, Dec. 1993, pp. 2675–2682.

Keith M. Skubitz, et. al., "Endogenous and Exogenous Adenosine Inhibits Granulocyte Aggregation Without Altering the Associated Rise in Intracellular Calcium Concentration," *Blood*, vol. 72, No 1 (Jul.), 1998: pp. 29–33.

Johan Richter, Effect of adenosine analogues and cAMP–raising agents on TNF–, GM–CSF–, and chemotactic peptide–induced degranulation in single, adherent neutrophils, *Journal of Leukocyte Biology*, vol. 51, Mar. 1992, pp. 270–275.

Bruce N. Cronstein, et. al., "Antiinflammatory Effects of Methotrexate are Mediated by Adenosine," *Purine and Pyrimidine Metabolism in Man VIII*, Edited by A. Sahota and M. Taylor, Plenum Press, New York, 1995, pp. 411–416.

Bruce N. Cronstein, et. al., "Adenosine Modulates the Generation of Superoxide Anion by Stimulated Human Neutrophils via Interaction with a Specific Cell Surface Receptor," *Annals of the New York Academy of Sciences*, –Adenosine Deaminase in Disorders of Purine Metabolism and in Immune Deficiency, vol. 451, 1985, pp. 290–301.

Bruce N. Cronstein, et. al., "A New Physiological Function for Adenosine: Regulation of Superoxide Anion Production," *Transactions of the Association of American Physicians*, Ninety–Sixth Session Held at Washington, DC, Apr. 20, 30 and May 1, 2, , vol. XCVI, pp. 384–391, 1993.

Bruce N. Cronstein, "Adenosine, an endogenous anti–inflammatory agent," *Journal of Applied Physiology*, Jan. 1994, vol. 76, No. 1, pp. 5–13.

Bedford CD, et. al., "Nonquaternary Cholinesterase Reactivators. 3. 3(5)–Substituted 1,2,4–Oxadiazol–5(3)–aldoximes and 1,2,4–Oxadiazole–5(3)–thiocarbohydroximates as Reactivators of Organophosphonate–Inhibited Eel and Human Acetylcholinesterase in Vitro," *J. Med Chem.*, vol. 29, pp. 2174–2183 (1986).

Castanon MJ, et. al., "Functional Coupling of Human Adenosine Receptors to a Ligand–Dependent Reporter Gene System," *Biochem. Biophys. Res. Commun.*, vol. 198, No. 2, 1994, pp. 626–631 (Jan. 28, 1994).

Flora KP, et. al., "Antitumor Activity of Amidoximes (Hydroxyurea Analogs) in Murine Tumor Systems," *Cancer Research*, vol. 38, pp. 1291–1295 (May 1978).

Wood KV. (1995) "Marker Proteins for Gene Expression," *Curr Opinion Biotechnology* 6 p 50–58.

J. Kobe, et. al., "Preparation and Utility of 5–B–D–fibofuranosyl–1H–tetrazole as a Key Synthon for C–nucleoside Synthesis," Nucleosides and Nucleotides, vol. 13, No. 10, 1994, pp. 2209–2244.

J.J. Baker, et. al., "5'–Substituted–5'–Deoxy Nucleosides," *Tetrahedron*vol. 30, pp. 2939–2942, Apr. 8, 1974.

Richard R. Schmidt, "Riburonsaurederivate zur gezielten Veranderung der Riobose," Liebigs Ann. Chem., 1974, pp. 1856–1863.

Mester, et. al., "Mode of Action of Some Oxidized Sugar Derivatives of Adenine on Platelet Aggregation," *Pathologie–Biologie*, 20, Suppl., pp 11–14, Dec. 1972.

U.S. patent application 09/720, 391—filed Jun. 29, 1999.

* cited by examiner

2-(PURIN-9-YL)-TETRAHYDROFURAN-3,4-DIOL DERIVATIVES

This application is filed pursuant to 35 U.S.C. §371 as a United States National Phase Application of International Application No. PCT/EP99/00503 filed 29 Jan. 1999, which claims priority from GB9802066.2 filed 31 Jan. 1998 and GB9813528.8 filed 23 Jun. 1998.

This invention relates to new chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation, into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine A2a receptor will have anti-inflammatory actions. The area has been reviewed by Cronstein (1994). Studies on isolated neutrophils show an A2 receptor-mediated inhibition of superoxide generation, degranulation, aggregation and adherence (Cronstein et al, 1983 and 1985; Burkey and Webster, 1993; Richter, 1992; Skubitz et al, 1988. When agents selective for the A2a receptor over the A2b receptor (eg CGS21680) have been used, the profile of inhibition appears consistent with an action on the A2a receptor subtype (Dianzani et al, 1994). Adenosine agonists may also down-regulate other classes of leukocytes (Elliot and Leonard, 1989; Peachell et al, 1989). Studies on whole animals have shown the anti-inflammatory effects of methotrexate to be mediated through adenosine and A2 receptor activation (Asako et at, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschom, 1993).

Certain substituted 4'-carboxamido and 4'-thioamido adenosine derivatives which are useful for the treatment of inflammatory diseases are described in International Patent Application Nos. WO94/17090, WO96/02553, WO96/02543 (Glaxo Group). Substituted 4'-carboxamidoadenosine derivatives useful in the treatment of dementia are described in AU 8771946 (Hoechst Japan). Substituted 4'-hydroxymethyl adenosine derivatives which are useful for the treatment of gastrointestinal motility disorders are described in EP-A423776 and EP-A423777 (Searle). Substituted 4'-hydroxymethyl adenosine derivatives which are useful as platelet aggregation inhibitors are described in BE-768925 (Takeda). 4'-Hydroxymethyl adenosine derivatives and 4'-esters thereof which are useful as antihypertensive agents or have other cardiovascular activity are described in U.S. Pat. No. 4,663,313, EP 139358 and U.S. Pat. No. 4,767,747 (Warner Lambert), U.S. Pat. No. 4,985,409 (Nippon Zoki) and U.S. Pat. No. 5,043,325 (Whitby Research). 4-Hydroxymethyladenosine derivatives useful in the treatment of autoimmune disorders are described in U.S. Pat. No. 5,106,837 (Scripps Research Institute). 4'-Hydroxymethyladenosine derivatives useful as antiallergic agents are described in U.S. Pat. No. 4,704,381 (Boehringer Mannheim). Certain 4'-tetrazolylalkyl adenosine derivatives which are useful in the treatment of heart and circulatory disorders are generically described in DT-A-2621470 (Pharma-Waldhof). Other 4'-carboxamidoadenosine derivatives useful in the treatment of cardiovascular conditions are described in U.S. Pat. No. 5,219,840, GB 2203149 and GB 2199036 (Sandoz), WO94/02497 (US Dept. Health), U.S. Pat. No. 4,968,697 and EP 277917 (Ciba Geigy), U.S. Pat. No. 5,424,297 (Univ. Virginia) and EP 232813 (Warner Lambert).

Other 4'-carboxamidoadenosine derivatives lacking substitution on the purine ring in the 2-position are described in DT 2317770, DT 2213180, U.S. Pat. No. 4,167,565, U.S. Pat. No. 3,864,483 and U.S. Pat. No. 3,966,917 (Abbott Labs), DT 2034785 (Boehringer Mannheim), JP 58174322 and JP 58167599 (Tanabe Seiyaku), WO92/05177 and U.S. Pat. No. 5,364,862 (Rhone Poulenc Rorer), EP 66918 (Procter and Gamble), WO86/00310 (Nelson), EP 222330, U.S. Pat. No. 4,962,194, WO88/03147 and WO88/03148 (Warner Lambert) and U.S. Pat. No. 5,219,839, WO95/18817 and WO93/14102 (Lab UPSA). 4'-Hydroxymethyladenosine derivatives lacking substitution on the purine ring in the 2-position are described in WO95/11904 (Univ Florida).

4'-Substituted adenosine derivatives useful as adenosine kinase inhibitors are described in WO94/18215 (Gensia).

Other 4'-halomethyl, methyl, thioalkylmethyl or alkoxymethyl adenosine derivatives are described in EP 161128 and EP 181129 (Warner Lambert) and U.S. Pat. No. 3,983,104 (Schering). Other 4'-carboxamidoadenosine derivatives are described in U.S. Pat. No. 7,577,528 (NIH), WO91/13082 (Whitby Research) and WO95/02604 (US Dept Health).

Certain tetrazole containing deoxynucleotides which were found to lack anti-infective activity are described in Baker et al (1974) Tetrahedron 30, 2939–2942. Other tetrazole containing adenosine derivatives which show activity as platelet aggregation inhibitors are described in Mester and Mester (1972) Pathologie-Biologie, 20 (Suppl) 11–14.

Certain nitrile containing ribose derivatives are described in Schmidt et al (1974) Liebigs. Ann. Chem. 1856–1863.

Specifications published subsequent to the earliest priority date of this application include: WO 98/28319 (Glaxo Group Limited) describing 4'-substituted tetrazole 2-(purin-9-yl)-tetrahydrofuran-3,4-diol derivatives; WO 98/16539 (Novo Nordisk A/S) which describes adenosine derivatives for the treatment of myocardial and cerebral ischaemia and epilepsy; WO 98/01426 (Rhone-Poulenc Rorer Pharmaceuticals Inc.) which relates to adenosine derivatives possessing antihypertensive, cardioprotective, anti-ischaemic and anti-lipolytic properties; and WO 98/01459 (Novo Nordisk A/S) which describes N,9-disubstituted adenine derivatives which are substituted in the 4' position by unsubstituted oxazolyl or isoxazolyl and the use of such compounds for the treatment of disorders involving cytokines in humans.

We have now found a novel group of compounds with broad anti-inflammatory properties which inhibit leukocyte recruitment and activation and which are agonists of the adenosine 2a receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses may be limited by their side-effect profiles.

More particularly, the compounds of this invention may show an improved profile over known A2a-selective agonists in that they generally lack agonist activity at the human A3 receptor. They may even possess antagonist activity at the human A3 receptor. This profile can be considered of benefit as A3 receptors are also found on leukocytes (eg eosinophil) and other inflammatory cells (eg mast cell) and activation of these receptors may have pro-inflammatory effects (Kohno et al, 1996; Van Schaick et al 1996). It is even considered that the bronchoconstrictor effects of adenosine in asthmatics may be mediated via the adenosine A3 receptor (Kohno et al, 1996).

Thus, according to the invention we provide compounds of formula (I):

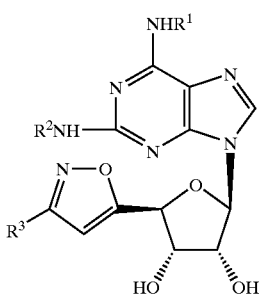

(I)

wherein $R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5$N—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more (e.g. 1, 2 or 3) —(CH$_2$)$_p$R$^6$ groups;
(xii) H$_2$NC(=NH)NHC$_{1-6}$alkyl-;
(xiii) a group of formula

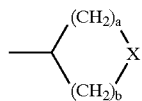

or such a group in which one methylene carbon atom adjacent to X, or both if such exist, is substituted by methyl;
(xiv) —$C_{1-6}$alkyl-OH;
(xv) —$C_{1-8}$haloalkyl;

(xvi) a group of formula

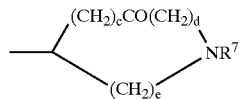

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;
$R^3$ represents methyl, ethyl, —CH=CH$_2$, n-propyl, —CH$_2$CH=CH$_2$, —CH=CHCH$_3$, isopropyl, isopropenyl, cyclopropyl, cyclopropenyl, cydopropylmethyl, cyclopropenylmethyl, —CH(OH)CH$_3$, —(CH)$_q$halogen, —(CH$_2$)$_h$Y(CH$_2$)$_i$H, —(CH$_2$)$_k$Z, —(CH$_2$)$_h$CO(CH$_2$)$_o$H, —(CH$_2$)$_r$S(O)$_t$(CH$_2$)$_s$H or —(CH$_2$)$_k$C((CH$_2$)$_u$H)=NO(CH$_2$)$_v$H;
Y represents O, S or N(CH$_2$)$_j$H;
Z represents —COO(CH$_2$)$_t$H or —CON(CH$_2$)$_m$H((CH$_2$)$_n$H);
a and b independently represent an integer 0 to 4 provided that a+b is in the range 3 to 5;
c, d and e independently represent an integer 0 to 3 provided that c+d+e is in the range 2 to 3;
f represents 2 or 3 and g represents an integer 0 to 2;
p represents 0 or 1;
q represents an integer 0 to 3;
h represents an integer 0 to 2;
i represents an integer 0 to 2 such that h+i is in the range 0 to 3;
j represents an integer 0 to 2 such that h+i+j is in the range 0 to 3;
k represents 0 or 1;
l represents 1 or 2, such that k+l is in the range 1 to 2;
m and n independently represent an integer 0 to 2 such that k+m+n is in the range 0 to 2;
o represents an integer 0 to 2 such that h+o is in the range 0 to 2;
r and s independently represent 1 or 2 such that r+s is in the range 2 to 3;
t represents 1 or 2;
u and v independently represent 0 or 1 such that k+u+v is in the range 0 to 1;
$R^4$ and $R^5$ independently represent hydrogen, $C_{1-4}$alkyl, aryl, aryl$C_{1-6}$alkyl- or NR$^4$R$^5$ together may represent pyridinyl, pyrrolidinyl, piperidinyl, morpholinyl, azetidinyl, azepinyl, piperazinyl, N—$C_{1-6}$alkylpiperazinyl or 2-(1-methyl-1H-imidazol-4-yl)-;
$R^6$ represents —OH, —NH$_2$, —NHCOCH$_3$ or halogen;
$R^7$ represents hydrogen, —$C_{1-6}$alkyl, —$C_{1-6}$alkylaryl or —COC$_{1-6}$alkyl;
X represents NR$^7$, O, S, SO or SO$_2$;
and salts and solvates thereof.

References to $C_{1-6}$alkyl include references to an aliphatic hydrocarbon grouping containing 1 to 6 carbon atoms which may be straight chain or branched and may be saturated or unsaturated. References to $C_{1-4}$alkyl, $C_{1-5}$alkyl and $C_{1-8}$alkyl may be interpreted similarly. References to alkoxy may also be interpreted similarly. Preferably these groups will be saturated.

References to aryl include references to mono- and bicyclic carbocyclic aromatic rings (e.g. phenyl, naphthyl) and heterocyclic aromatic rings containing 1–3 hetero atoms selected from N, O and S (e.g. pyridinyl, pyrimidinyl, thiophenyl, imidazolyl, quinolinyl, furanyl, pyrrolyl, oxazolyl) all of which may be optionally substituted, e.g. by $C_{1-6}$alkyl, halogen, hydroxy, nitro, $C_{1-6}$alkoxy, cyano, amino, $SO_2NH_2$ or —$CH_2OH$.

Examples of $C_{3-8}$cycloalkyl for $R^1$ and $R^2$ include monocyclic alkyl groups (e.g. cyclopentyl, cyclohexyl) and bicyclic alkyl groups (e.g. norbornyl such as exo-norborn-2-yl).

Examples of $(aryl)_2CHCH_2$— for $R^1$ and $R^2$ include $Ph_2CHCH_2$— or such a group in which one or both phenyl moieties is substituted, e.g. by halogen or $C_{1-4}$alkyl.

Examples of $C_{3-8}$cycloalkyl$C_{1-6}$alkyl- for $R^1$ and $R^2$ include ethylcyclohexyl.

Examples of $C_{1-8}$alkyl for $R^1$ and $R^2$ include —$(CH_2)_2C(Me)_3$, —$CH(Et)_2$ and $CH_2$=$C(Me)CH_2CH_2$—.

Examples of aryl$C_{1-6}$alkyl- for $R^1$ and $R^2$ include —$(CH_2)_2Ph$, —$CH_2Ph$ or either in which Ph is substituted (one or more times) by halogen (e.g. fluorine, iodine), amino, methoxy, hydroxy, —$CH_2OH$ or $SO_2NH_2$; —$(CH_2)_2$pyridinyl (e.g.—$(CH_2)_2$pyridin-2-yl) optionally substituted by amino; $(CH_2)_2$imidazolyl (eg 1H-imidazol-4-yl) or this group in which imidazolyl is N-substituted by $C_{1-6}$alkyl (especially methyl).

Examples of $R^4R^5N$—$C_{1-6}$alkyl- for $R^1$ and $R^2$ include ethyl-piperidin-1-yl, ethyl-pyrrolidin-1-yl, ethyl-morpholin-1-yl, —$(CH_2)_2NH$(pyridin-2-yl) and —$(CH_2)_2NH_2$.

Examples of $C_{1-6}$alkyl-$CH(CH_2OH)$— for $R^1$ and $R^2$ include $Me_2CHCH(CH_2OH)$—.

Examples of aryl$C_{1-5}$alkyl-$CH(CH_2OH)$— for $R^1$ and $R^2$ include $PhCH_2CH(CH_2OH)$— particularly Examples of aryl $C_{1-5}$alkyl-$C(CH_2OH)_2$— for $R^1$ and $R^2$ include $PhCH_2C(CH_2OH)_2$—.

Examples of $C_{3-8}$cycloalkyl independently substituted by one or more —$(CH_2)_pR^6$ groups (eg 1, 2 or 3 such groups) for $R^1$ and $R^2$ include 2-hydroxy-cyclopentyl and 4-aminocyclohexyl (especially trans-4-amino-cyclohexyl).

Examples of $H_2NC$(=NH)$NHC_{1-6}$alkyl for $R^1$ and $R^2$ include $H_2NC$(=NH)$NH(CH_2)_2$—

Examples of groups of formula for $R^1$ and $R^2$ include pyrrolidin-3-yl, piperidin-3-yl, piperidin-4-yl, tetrahydro-1,1-dioxide thiophen-3-yl, tetrahydropyran-4-yl, tetrahydrothiopyran-4-yl, 1-oxo-hexahydro-1.lambda.4-thiopyran-4-yl and 1,1-dioxo-hexahydro-1.lambda.6-thiopyran-4-yl, or a derivative in which the ring nitrogen is substituted by $C_{1-6}$alkyl (e.g. methyl), $C_{1-6}$alkylacyl (e.g. acetyl), aryl$C_{1-6}$alkyl- or benzyl.

Examples of —$C_{1-6}$alkyl-OH groups for $R^1$ and $R^2$ include —$CH_2CH_2OH$.

Examples of $C_{1-8}$haloalkyl for $R^1$ and $R^2$ include —$CH_2CH_2Cl$ and $(CH_3)_2ClC(CH_2)_3$—.

Examples of groups of formula for $R^1$ and $R^2$ include 2-oxopyrrolidin-4-yl, 2-oxopyrrolidin-5-yl or a derivative in which the ring nitrogen is substituted by $C_{1-6}$alkyl (e.g. methyl) or benzyl.

Examples of aryl for $R^1$ and $R^2$ include phenyl optionally substituted by halogen (e.g. fluorine, especially 4-fluorine).

An example of a —$(CH_2)_fSO_2NH_g(C_{1-4}alkyl)_{2-g}$ group for $R^1$ and $R^2$ is —$(CH_2)_2SO_2NHMe$, and an example of a —$(CH_2)_fSO_2NH_g(arylC_{1-4}alkyl)_{2-g}$ group for $R^1$ and $R^2$ is —$(CH_2)_2SO_2NHCH_2Ph$.

Examples of $C_{1-6}$alkyl for $R^1$ include methyl, of $C_{1-6}$alkylaryl for $R^7$ include benzyl and of $COC_{1-6}$alkyl for $R^7$ include $COCH_3$.

We prefer that $R^1$ and $R^2$ do not both represent hydrogen.

We prefer $R^1$ to represent $C_{3-6}$cycloalkyl, aryl$_2$CHCH$_2$—, aryl$C_{1-6}$alkyl-, $C_{1-6}$alkyl-, aryl, —$(CH_2)_fSO_2NH_g(C_{1-4}alkyl)_{2-g}$, tetrahydropyran-n-yl or tetrahydrothiopyran-n-yl where n is 3 or 4, $C_{3-8}$cycloalkyl$C_{1-6}$alkyl-, hydrogen, or $R^4R^5N$—$C_{1-4}$alkyl- where $NR^4R^5$ together represents piperidinyl or morpholinyl.

We also prefer $R^1$ to represent $C_{1-6}$alkyl-$CH(CH_2OH)$—, 1,1-dioxo-hexahydro-1.lambda.6-thiopyran-4-yl, N-acetyl-piperidin-4-yl, 1S-hydroxymethyl-2-phenylethyl, piperidin-4-yl and 1-oxo-hexahydro-1.lambda.4-thiopyran-4-yl.

We prefer $R^2$ to represent —$C_{1-6}$alkyl-OH, $H_2NC$(=NH)$NHC_{1-6}$alkyl-, $R^4R^5NC_{1-6}$alkyl- where $NR^4R^5$ together represents pyridinyl, piperidinyl, morpholinyl or 2-(1-methyl-1H-imidazol-4-yl), aryl$C_{1-5}$alkyl$CH(CH_2OH)$—, aryl, $C_{3-8}$cycloalkyl$C_{1-6}$alkyl-, tetrahydro-1,1-dioxide thiophen-3-yl, $C_{3-8}$cycloalkyl, $C_{1-6}$alkyl-$CH(CH_2OH)$—, aryl$C_{1-6}$alkyl-, pyrrolidin-3-yl, 2-oxopyrrolidin-4-yl, 2-oxopyrrolidin-5-yl, piperidin-3-yl, aryl $C_{1-6}$alkyl (e.g. benzyl), $C_{3-8}$cycloalkyl independently substituted by one or more (e.g. 1, 2 or 3) —$(CH_2)_pR^6$ groups, or piperidin-4-yl in which the ring nitrogen is optionally substituted by $C_{1-6}$alkyl.

We also prefer $R^2$ to represent $C_{1-8}$alkyl or $R^4R^5NC_{1-6}$alkyl- wherein $R^4$ and $R^5$ independently represent hydrogen or aryl or $R^4R^5N$ together represents pyrrolidinyl.

When $R^3$ represents halogen, we prefer it to represent bromine or chlorine, especially bromine.

We prefer $R^3$ to represent methyl, ethyl or n-propyl.

We also prefer $R^3$ to represent —CH=NOH, cyclopropyl, —$COOCH_3$, —$COOCH_2CH_3$, —$CH_2OH$, —$CH(OH)CH_3$ or halogen.

More preferably $R^3$ represents methyl, ethyl, n-propyl, —$CH_2OH$, —$CH(OH)CH_3$, —CH=NOH or halogen.

We particularly prefer $R^3$ to represent methyl, ethyl, —$CH_2OH$ or —$CH(OH)CH_3$, more particularly methyl, ethyl or —$CH_2OH$, especially ethyl or —$CH_2OH$, most especially ethyl.

We particularly prefer $R^4$ and $R^5$ independently to represent hydrogen, $C_{1-6}$alkyl, aryl, aryl$C_{1-6}$alkyl- or $NR^4R^5$ together may represent pyrrolidinyl, piperidinyl, morpholinyl, azetidinyl, azepinyl, piperazinyl or N—$C_{1-6}$alkylpiperazinyl.

We more particularly prefer $R^4$ and $R^5$ independently to represent hydrogen, $C_{1-6}$alkyl or aryl or $NR^4R^5$ together to represent pyrrolidinyl, piperidinyl, morpholinyl, azetidinyl, azepinyl, piperazinyl or N-methylpiperazinyl.

We prefer that p represents 0. We prefer that $R^6$ represents OH or $NH_2$ especially OH.

We prefer that q represents 0 or 1, preferably 0. We prefer that Y represents O.

We prefer that Z represents —COOCH$_3$. We prefer that the group —(CH$_2$)$_n$Y(CH$_2$)$_r$H represents —(CH$_2$)$_{1-2}$OH. We prefer that k represents 0. We prefer that u and v represent 0. We prefer that r and s represent 1. We prefer that the group —(CH$_2$)$_h$CO(CH$_2$)$_o$H represents —COCH$_3$. We prefer that I represents 1.

We prefer that a and b both represent 2. We prefer X to represent NR$^7$, O, S or SO$_2$, particularly O or S.

We prefer that c represents 0 and either d represents 2 and e represents 0 or d represents 1 and e represents 1.

We prefer R$^7$ to represent hydrogen, C$_{1-6}$alkyl, C$_{1-6}$alkylaryl or —COCH$_3$, particularly hydrogen, benzyl or —COCH$_3$, especially hydrogen.

We prefer R$^3$ to represent methyl, ethyl or n-propyl and R$^7$ to represent hydrogen, —C$_{1-6}$alkyl, —C$_{1-6}$alkylaryl or —COCH$_3$.

We particularly prefer R$^1$ to represent C$_{4-7}$cycloalkyl (particularly cyclopentyl), Ph$_2$CHCH$_2$—, PhCH$_2$CH$_2$—, C$_{4-7}$alkyl, particularly —(CH$_2$)$_2$C(Me)$_3$ or —CH(Et)$_2$, a phenyl group substituted by both an —OH and a halogen group (e.g. fluorine) (e.g. 3-fluoro-4-hydroxy-phenyl), —(CH$_2$)$_2$SO$_2$NHMe, or tetrahydropyran-n-yl or tetrahydrothiopyran-n-yl where n is 4.

We also particularly prefer R$^1$ to represent hydrogen, 1S-hydroxymethyl-2-methylpropyl, 3-iodophenylmethyl, cyclohexylethyl-, benzyl, 1,1-dioxo-hexahydro-1.lambda.6-thiopyran-4-yl, N-acetyl-piperidin-4-yl, 1S-hydroxymethyl-2-phenylethyl, piperidin-4-yl and 1-oxo-hexahydro-1.lambda.4-thiopyran-4-yl.

Most especially preferred R$^1$ is —CH$_2$CHPh$_2$, —CH(Et)$_2$ or phenylethyl.

We particularly prefer R$^2$ to represent —C$_{2-4}$alkyl-OH, H$_2$NC(=NH)NHC$_{2-4}$alkyl or R$^4$R$^5$N—C$_{1-4}$alkyl- where NR$^4$R$^5$ together represents pyridinyl, piperidinyl, morpholinyl or 2-(1-methyl-1H-imidazol-4-yl).

We also particularly prefer R$^2$ to represent 2-(1-methyl-1H-imidazol-4-yl)ethyl, pyridin-2-ylethyl, 1S-hydroxymethyl-2-phenylethyl, pyridin-2-yl-NH(CH$_2$)$_2$—, 4-(H$_2$NSO$_2$)-phenylethyl, trans-4-aminocyclohexyl, trans-4-(CH$_3$CONH)-cyclohexyl, pyrrolidin-3-yl, 3,4-dimethoxyphenylethyl, N-benzyl-pyrrolidin-3-yl-, pyrrolidin-1-ylethyl, aminoethyl or ethyl.

We especially prefer R$^2$ to represent piperidin-1-ylethyl, morpholin-1-ylethyl, —(CH$_2$)$_2$OH, 2-(1-methyl-1H-imidazol-4-yl)ethyl, H$_2$NC(=NH)NHethyl, pyridin-2-ylethyl, 1S-hydroxymethyl-2-phenylethyl, pyridin-2-yl-NH (CH$_2$)$_2$—, 4-(H$_2$NSO$_2$)-phenylethyl, trans-4-aminocyclohexyl, trans-4-(CH$_3$CONH)-cyclohexyl, pyrrolidin-3-yl, 3,4-dimethoxyphenylethyl, N-benzyl-pyrrolidin-3-yl-, pyrrolidin-1-ylethyl, aminoethyl or ethyl.

Most especially preferred R$^2$ is piperidin-1-ylethyl or 2-(1-methyl-1H-imidazol-4-yl)ethyl.

The most preferred compounds of formula (I) are (2R,3R,4S,5S)-2-[6-(2,2-Diphenyl-ethylamino)-2-(2-piperidin-1-yl-ethylamino)-purin-9-yl]-5-(3-ethyl-isoxazol-5-yl)-tetrahydro-furan-3,4-diol;

(2R,3R,4S,5S)-2-(3-Ethyl-isoxazol-5-yl)-5-[6-phenethylamino-2-(2-piperidin-1-yl-ethylamino)-purin-9-yl]-tetrahydro-furan-3,4-diol;

(2S,3S,4R,5R)-2-(3-Ethyl-isoxazol-5-yl)-5-[6-(1-ethyl-propylamino)-2-(2-piperidin-1-yl-ethylamino)-purin-9yl]-tetrahydro-furan-3,4-diol;

(2R,3R,4S,5S)-2-[6-(1-Ethyl-propylamino)-2-(2-piperidin-1-yl-ethylamino)-purin-9-yl]-5-[3-(1-hydroxy-ethyl)-isoxazol-5-yl]-tetrahydro-furan-3,4-diol;

(2R,3R,4S,5S)-2-{6-(1-Ethyl-propylamino)-2-[2-(1-methyl-1H-imidazol-4-yl)-ethylamino]-purin-9-yl}5-(3-methyl-isoxazol-5-yl)-tetrahydro-furan-3,4-diol;

(2R,3R,4S,5S)-2-{6-(1-Ethyl-propylamino)-2-[2-(1-methyl-1H-imidazol-4-yl)-ethylamino]-purin-9-yl}-5-(3-hydroxymethyl-isoxazol-5-yl)-tetrahydro-furan-3,4-diol;

and salts and solvates thereof.

The representation of formula (I) indicates the absolute stereochemistry. When sidechains contain chiral centres the invention extends to mixtures of enantiomers (including racemic mixtures) and diastereoisomers as well as individual enantiomers. Generally it is preferred to use a compound of formula (I) in the form of a purified single enantiomer.

We also provide a process for preparation of compounds of formula (I) which comprises:

(a) reacting a corresponding compound of formula (II)

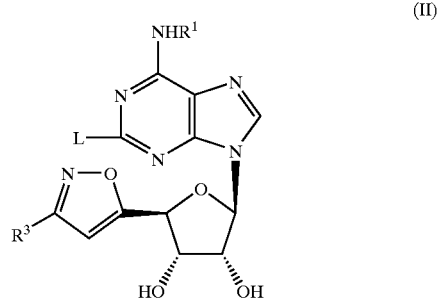

(II)

wherein L represents a leaving group e.g. halogen, particularly chlorine or a protected derivative thereof with a compound of formula R$^2$NH$_2$ or a protected derivative thereof;

(b) reacting a corresponding compound of formula (III)

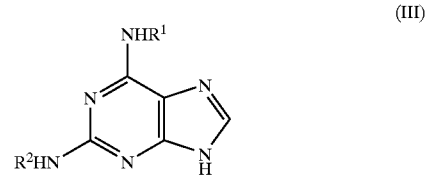

(III)

with a compound of formula (IV)

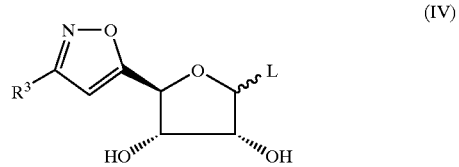

(IV)

wherein L represents a leaving group or a protected derivative thereof;

(c) converting one compound of formula (I) to another compound of formula (I); or (d) deprotecting a compound of formula (I) which is protected;

and where desired or necessary converting a compound of formula (I) or a salt thereof into another salt thereof.

The reaction of process (a) will generally be carried out on heating the reagents to a temperature of 50° C.–150° C. in the presence of an inert solvent such as DMSO. The compound of formula (II) will generally be used in a form which the two hydroxyl groups are protected e.g. with acetyl groups.

In process (b), we prefer to use the compound of formula (IV) when the ribose 2- and 3-hydroxyl groups are protected for example by acetyl. Leaving group L may represent OH but will preferably represent $C_{1-6}$alkoxy (e.g. methoxy or ethoxy) an ester moiety (e.g. acetyloxy or benzoyloxy) or halogen. The preferred group L is acetyloxy. The reaction may be formed by combining the reactants in an inert solvent such as MeCN in the presence of a Lewis Acid (e.g. TMSOTf) and DBU.

Examples of process (c) include converting compounds of formula (I) wherein $R^3$ represents halogen (e.g. Br) to a corresponding compound of formula (I) wherein $R^3$ represents alkyl or a protected alcohol for example by treatment with a corresponding metallic reagent such as a magnesium or zinc halide optionally catalysed by another metal such as Pd in the presence of ligands such as $PPh_3$. Compounds of formula (I) wherein $R^3$ represents halogen (e.g. Br) may be converted to corresponding compounds of formula (I) wherein $R^3$ represents alkoxy by treatment with the corresponding metal alkoxide (eg $KOCH_3$) in the corresponding alcoholic solvent.

In process (d) examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl e.g. benzyloxycarbonyl or t-butoxycarbonyl) and arylalkyl (e.g. benzyl) which may be removed by hydrolysis or hydrogenolysis as appropriate.

We also provide a further process (e) for preparing compounds of formula (I) which comprises reacting a corresponding compound of formula (IIa):

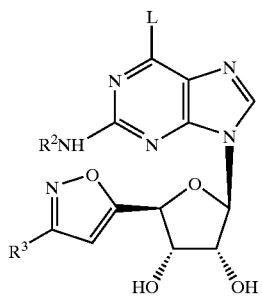

(IIa)

wherein L represents a leaving group eg. halogen, particularly chlorine or a protected derivative thereof, with a compound of formula $R^1NH_2$ or a protected derivative thereof.

This reaction may be performed under conditions analogous to those described above for process (a).

Suitable salts of the compounds of formula (I) include physiologically acceptable salts such as acid addition salts derived from inorganic or organic acids, for example hydrochlorides, hydrobromides, sulphates, phosphates, acetates, benzoates, citrates, succinates, lactates, tartrates, fumarates, maleates, 1-hydroxynathanoate, methanesulphonate, and if appropriate, inorganic base salts such as alkali metal salts, for example sodium salts. Other salts of the compounds of formula (I) include salts which are not physiologically acceptable but may be useful in the preparation of compounds of formula (I) and physiologically acceptable salts thereof. Examples of such salts include trifluoroacetates and formates.

Examples of suitable solvates of the compounds of formula (I) include hydrates.

Acid-addition salts of compounds of formula (I) may be obtained by treating a free-base of formula (I) with an appropriate acid.

The compounds of formula (II) may be prepared by a process which comprises reacting a compound of formula (V)

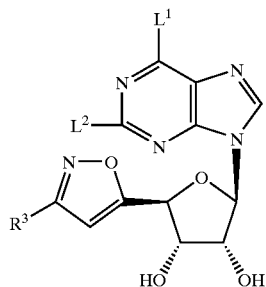

(V)

wherein $L^1$ and $L^2$ independently represent a leaving group, especially halogen (eg chlorine) or a protected derivative thereof with a compound of formula $R^1NH_2$.

This reaction will preferably be performed in the presence of a base such as an amine base (e.g. diisopropyl ethylamine) in a solvent such as DMF or an alcohol (e.g. isopropanol) at elevated temperature (e.g. 50° C.).

The compounds of formula (V) may be prepared by a process which comprises reacting a compound of formula (IV) with a purine derivative such as dihalopurine especially 2,6 dichloropurine under conditions analogous to those described above in process (b).

Compounds of formula (II) may be prepared by a route analogous to process (b) also.

The compounds of formula (IV) or a protected derivatives thereof may be prepared from a compound of formula (VI)

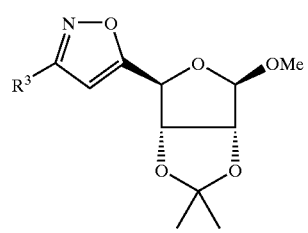

(VI)

by a process comprising treating the compound of formula (VI) with trifluoroacetic acid in water followed by acetic anhydride in a solvent such as pyridine, $Et_3N$, DCM or a combination of these.

Compounds of formula (IV) in which L represents halogen may be prepared from the corresponding 5-alcohol or a 5-ester such as the acetate. Reaction will generally occur on treatment with anhydrous HCl or HBr. 5-Iodides may be prepared directly on treatment with trimethylsilyliodide and 5-fluorides may be prepared on treatment with DAST. An inert solvent, e.g. diethylether, DCM, THF or $CCl_4$ will generally be suitable.

The compound of formula (VI) may be prepared following Scheme 1.

Scheme 1

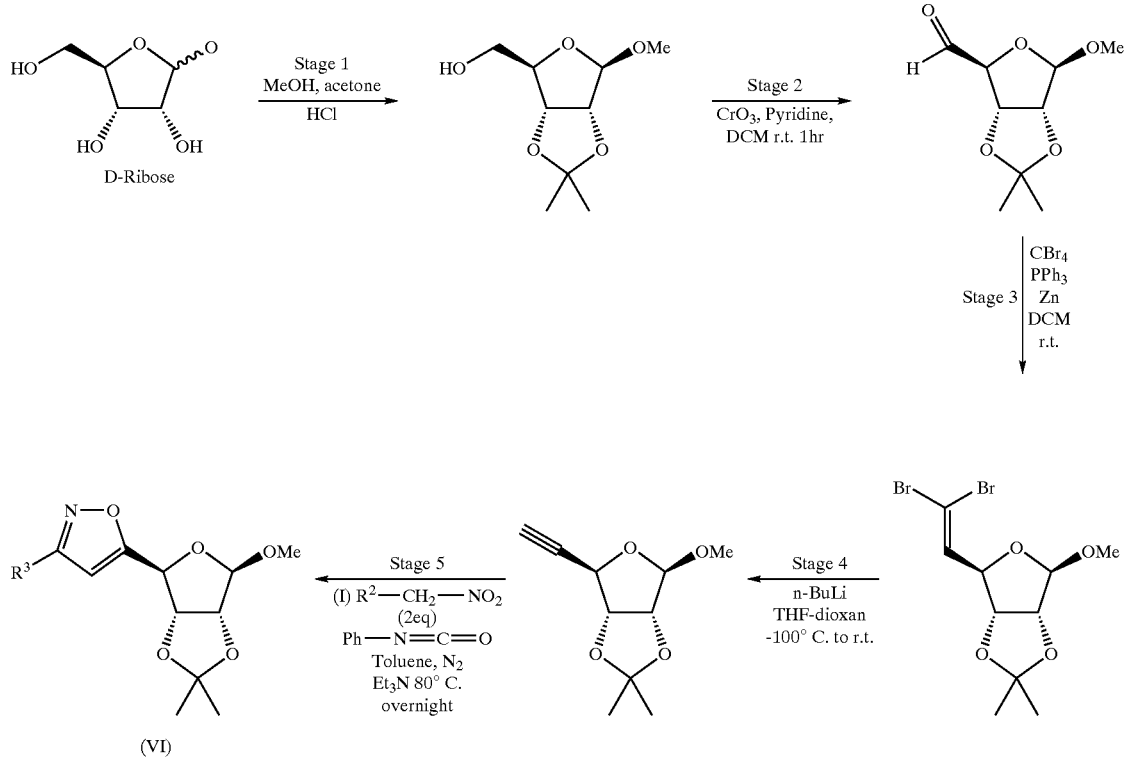

General conditions for Stages 1–5 will be known to persons skilled in the art. It will also be appreciated that the reagents and conditions set out in Scheme 1 are example conditions and alternative reagents and alternative conditions for achieving the same chemical transformation involving modification of protecting groups may be known to persons skilled in the art. For example an alternative alcohol e.g. a $C_{1-6}$alkyl alcohol may be used in Stage 1 to give a different $C_{1-6}$alkyloxy leaving group in compounds of formula (VI).

Certain compounds of formula (IV), in which L represents OMe may also be prepared following Scheme 1A:

Scheme 1A

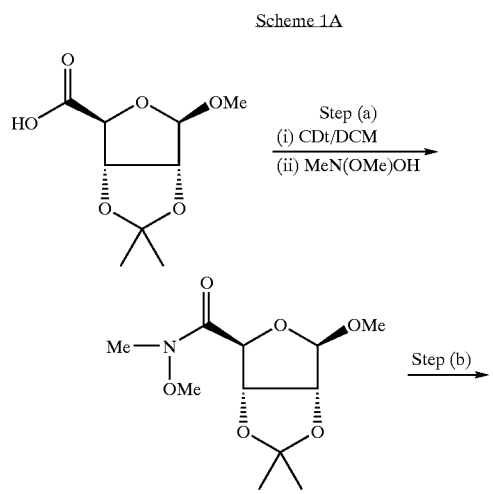

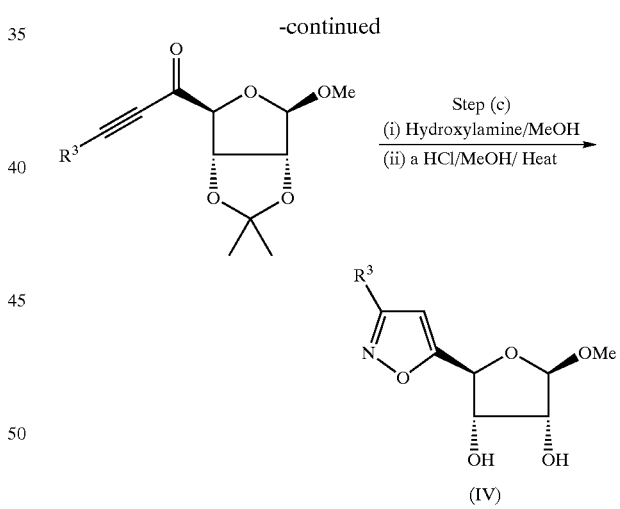

When $R^3$ represents —$CH_2OH$, suitable conditions for step (b) comprise treatment with a suitable lithium reagent, such as nBuLi/HC≡$CCH_2$OTHP followed by $BF_3.Et_2O$ in the presence of an inert solvent eg. THF at low temperatures (typically −78° C.). When $R^3$ represents alkyl, particularly ethyl, the transformation may be performed using a Grignard reagent, eg. MgBrC≡C—$CH_2CH_3$ in an inert solvent eg. THF, followed by work-up.

Compounds of formula (III) may be prepared, for example, following Scheme 2:

Scheme 2
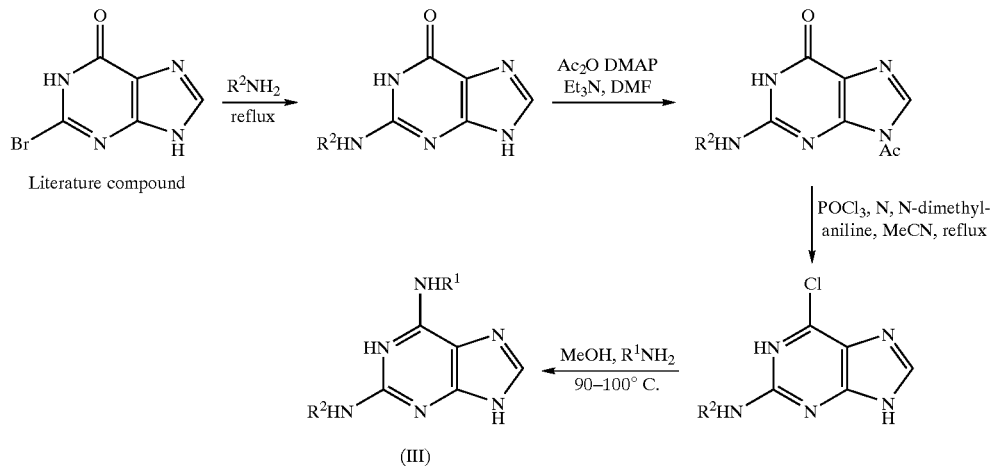
Compounds of formula (II) may also be prepared following Scheme 3:
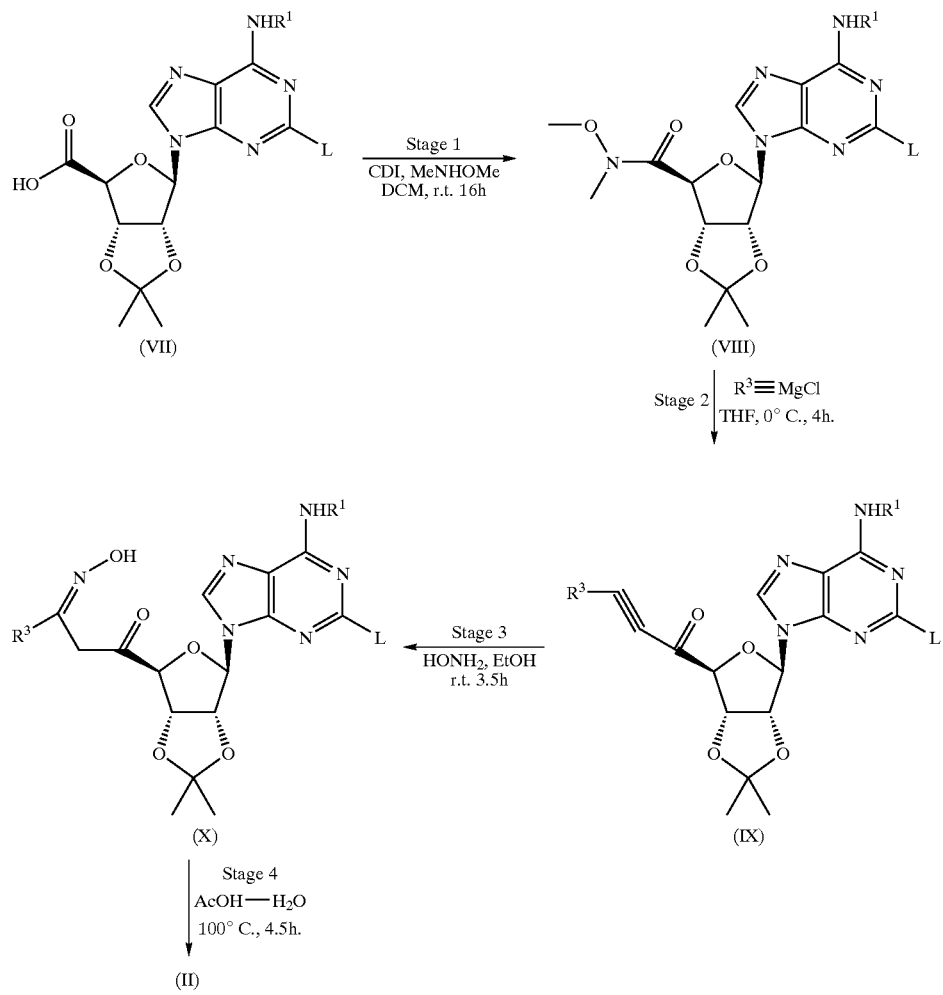

Preferred leaving group L is halogen, especially chlorine.

General conditions for Stages 1–4 will be known to persons skilled in the art. It will also be appreciated that the reagents and conditions set out in Scheme 2 are example conditions and alternative reagents and alternative conditions for achieving the same chemical transformation involving modification (or absence) of protecting groups may be known to persons skilled in the art.

The conditions of Scheme 3 Stages 1–4 may also be suitable for forming the substituted isoxazolyl ring of compounds of formula (IV), (V) and (VI).

Compounds of formula (II) may also be prepared by a process which comprises reacting a compound of formula (XI)

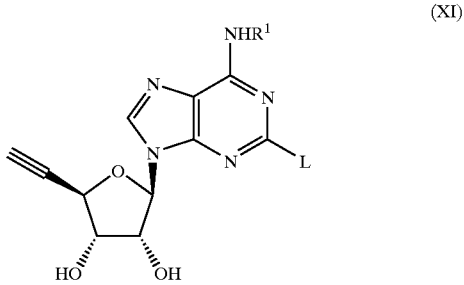

(XI)

wherein L is a leaving group such as halogen, especially chlorine or a protected derivative thereof, with a nitrile oxide derived from a compound of formula $R_3CH_2NO_2$. Suitable conditions are described above for Scheme 1, Stage 5. We prefer to use the compound of formula (XI) as a derivative in which both hydroxy groups are protected as the acetyl ester.

Compounds of formula (XI) (especially those wherein L represents chlorine) may be prepared from the corresponding dichloropurine derivatives which may in turn be prepared from the compound which is the product of Scheme 1, Stage 4 using conventional methods or methods described herein.

Compounds of formula (II) may also be prepared by a process comprising reacting a compound of formula (XI), or a protected derivative thereof, with a compound of formula (XII).

(XII)

wherein Hal represents halogen, eg chlorine or bromine.

This reaction may proceed on combining the reagents in the presence of a mild base eg $NaHCO_3$ or triethylamine in the presence of a polar organic solvent system such as ethylacetate/water or DMF.

Compounds of formula (II) in which $R^3$ represents $CH(OH)CH_3$ may be prepared by reduction of the corresponding methylketone (using conventional reagents such as $NaBH_4$) The corresponding methylketone can be prepared from a derivative compound of formula (XII) in which $R^3$ represents $COCH_3$.

Compounds of formula (IIa) may be prepared by reaction of a compound of formula (XIII):

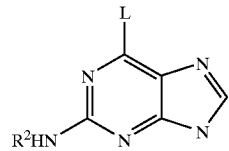

(XIII)

with a compound of formula (IV) under analogous conditions to those described for main process (b) above.

Compounds of formula (XIII) in which L represents chlorine can be prepared by reacting 2-bromoxanthine with $R^2NH_2$ followed by $POCl_3$. Derivatives of compounds of formula (XIII) containing a different leaving group, L may be prepared by an analogous method.

Compounds of formula $R^1NH_2$, $R^2NH_2$ and $R_3CH_2NO_2$ are either known or may be prepared by conventional methods known per se.

Compounds of formula (VII) may be prepared following methods described in International Patent Application No. WO94/17090.

Compounds of formula $R^1$—≡—MgCl may be prepared by conventional methods known to those skilled in the art. For example, they may be prepared by reacting methyl magnesium chloride with a terminal acetylene compound at 0–25° C. in THF.

Compounds of formula (XII) are either known or may be prepared by conventional methods known per se.

As indicated above, certain intermediates may be used in a protected form and examples of such protecting groups and methods of deprotection are described in main process (d) above.

The potential for compounds of formula (I) to inhibit leukocyte function may be demonstrated, for example, by their ability to inhibit superoxide ($O_2$—) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component eg Alzheimer's disease and multiple sclerosis.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis and promoting wound healing.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable carriers or excipients.

There is also provided a process for preparing such a pharmaceutical formulation which comprises mixing the ingredients.

The compounds according to the invention may, for example, be formulated for oral, buccal, parenteral, topical or rectal administration, preferably for parenteral or topical (e.g. by aerosol) administration. The most preferred route is by topical administration to the lung (eg. by aerosol or dry powder composition).

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluorethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (eg fluticasone propionate, beclomethasone dipropionate, mometasone furoate, triamcinolone acetonide or budesonide) or NSAIDs (eg sodium cromoglycate)) or beta adrenergic agents (such as salmeterol, salbutamol, formoterol, fenoterol or terbutaline and salts thereof) or antiinfective agents (eg antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

Certain intermediate compounds described herein are new and these are also provided as an aspect of the invention.

The compounds of the invention have the advantage that they may be more efficacious, show greater selectivity, have fewer side effects, have a longer duration of action, be more bioavailable by the preferred route, show less systemic activity when administered by inhalation or have other more desirable properties than similar known compounds.

In particular the compounds of the invention have the advantage that they may show greater selectivity for the adenosine 2a receptor subtype over other adenosine receptor subtypes (especially the A1 and A3 receptor subtypes) than hitherto known compounds.

Compounds of the invention may be tested for in vitro and in vivo biological activity in accordance with the following screens:

(1) Agonist Activity Against Adenosine 2a, Adenosine 1 and Adenosine 3 Receptor Subtypes.

Agonist selectivity of compounds against other human adenosine receptors is determined using Chinese hamster ovary (CHO) cells transfected with the gene for the relevant human adenosine receptor following a method based on that of Castanon and Spevak, 1994. The CHO cells are also transfected with cyclic AMP response elements promoting the gene for secreted placental alkaline phosphatase (SPAP) (Wood, 1995). The effect of test compounds may be determined by their effects on basal levels of cAMP (A2a) or on forskolin-enhanced cAMP (A1 and A3) as reflected by changes in levels of SPAP. $EC_{50}$ values for compounds may then be determined as a ratio to that of the non-selective agonist N-ethyl carboxamide adenosine (NECA).

(2) Antigen-induced Lung Eosinophil Accumulation in Sensitised Guinea Pigs.

Ovalbumin sensitised guinea pigs are dosed with mepyramine (1 mg/kg ip) to protect against anaphylactic bronchospasm. A compound of the invention is then given by the inhaled route (30 min breathing of an aerosol of the compound) immediately prior to ovalbumin challenge (30 min breathing of an aerosol generated from a 50 ug/ml solution of ovalbumin). Twenty four hours after challenge, the guinea pigs are killed and the lungs lavaged. Total and differential leukocyte counts are then obtained for the bronchoalveolar lavage fluid and the dose of test compound giving a 50% reduction in eosinophil accumulation ($ED_{50}$) is determined (Sanjar et al. 1992).

References

Asako H, Wolf, R E, Granger, D N (1993), Gastroenterology 104, pp 31–37;
Burkey T H, Webster, R O, (1993), Biochem. Biophys Acta 1175, pp 312–318;
Castanon M J, Spevak W, (1994), Biochem. Biophys Res. Commun. 198, pp 626–631;
Cronstein B N, Kramer S B, Weissmann G, Hirschhorn R, (1983), Trans. Assoc. Am. Physicians 96, pp 384–91;
Cronstein B N, Kramer S B, Rosenstein E D, Weissmann G, Hirschhorn R, (1985), Ann N.Y. Acad. Sci. 451, pp 291–301;
Cronstein B N, Naime D, Ostad E, (1993), J. Clin. Invest. 92, pp 2675–82;
Cronstein B N, Naime D, Ostad E, (1994), Adv. Exp. Med. Biol., 370, pp 411–6;
Cronstein B N, (1994), J. Appl. Physiol. 76, pp 5–13;
Dianzani C, Brunelleschi S, Viano I, Fantozzi R, (1994), Eur. J. Pharmacol 263, pp 223–226;
Elliot K R F, Leonard E J, (1989), FEBS Letters 254, pp 94–98;
Green P G, Basbaum A I, Helms C, Levine J D, (1991), Proc. Natl. Acad Sci. 88, pp 4162–4165;
Hirschom R, (1993), Pediatr. Res 33, pp S35–41;
Kohno Y; Xiao-duo J; Mawhorter S D; Koshiba M; Jacobson K A. (1 996).Blood 88 p3569–3574.
Peachell P T, Lichtenstein L M, Schleimer R P, (1989), Biochem Pharmacol 38, pp 1717–1725;
Richter J, (1992), J. Leukocyte Biol. 51, pp 270–275;
Rosengren S, Bong G W, Firestein G S, (1995), J. Immunol. 154, pp 5444–5451;
Sanjar S, McCabe P J, Fattah D, Humbles A A, Pole S M, (1992), Am. Rev. Respir. Dis. 145, A40;
Skubitz K M, Wickman N W, Hammerschmidt D E, (1988), Blood 72, pp 29–33
Van Schaick E A; Jacobson K A; Kim H O; Ijzerman A P; Danhof M. (1996) Eur J Pharmacol 308 p311–314.
Wood K V. (1995) Curr Opinion Biotechnology 6 p50–58.

The invention is illustrated by the following Examples:

EXAMPLES

General Experimental Details

Where products were purified by column chromatography, 'flash silica' refers to silica gel for chromatography, 0.040 to 0.063 mm mesh (e.g. Merck Art 9385), where column elution was accelerated by an applied pressure of nitrogen at up to 5 p.s.i. 'Biotage' refers to the use of the Biotage Flash 40 system using pre-packed normal phase silica columns where column elution was accelerated by an applied pressure of nitrogen up to 20 p.s.i.

Where thin layer chromatography (TLC) has been used it refers to silica gel TLC using 5×10 cm silica gel 60 $F_{254}$ plates (e.g. Merck Art 5719).

Where products were purified by preparative HPLC, this was carried out on a C18-reverse-phase column (1" Dynamax), eluting with a gradient of acetonitrile (containing 0.1% trifluoroacetic acid) in water (containing 0.1% trifluoroacetic acid) and the compounds isolated as their trifluoroacetate salts unless otherwise specified.

Standard Automated Preparative HPLC Column, Conditions & Eluent

Automated preparative high performance liquid chromatography (autoprep. HPLC) was carried out using a Supelco ABZ+ 51 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 5–95% over 20 minutes.

LC/MS System

The Liquid Chromatography Mass Spectroscopy (LC/MS) systems used:

LC/MS System A—A Supelco ABZ+, 3.3 cm×4.6 mm i.d. column eluting with solvents: A—0.1% v/v formic acid+ 0.077% w/v ammonium acetate in water, and B—95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% B over 0.3 mins. Positive and negative electrospray ionization was employed.

LC/MS System B—A Supelco ABZ+, 5 cm×2.1 mm i.d. column eluting with solvents: A—0.1% v/v formic acid+ 0.077% w/v ammonium acetate in water, and B—95:5 acetonitrile:water+0.05% v/v formic acid. The following gradient protocol was used: 0–100% B over 3.5 mins; hold at 100% B for 1.50 mins; return to 0% B over 0.50 mins. Positive and negative electrospray ionization was employed.

LC/MS System C—A Supelco ABZ+, 3.3 cm×4.6 mm i.d. column eluting with solvents: A—0.1% v/v formic acid+10 mmol ammonium acetate in water, and B—95:5 acetonitrile:water+0.05% v/v formic acid. The following gradient protocol was used: 100% A for 0.7 mins; A+B mixtures, gradient profile 0–100% B over 3.7 mins; hold at 100% B for 0.9 mins; return to 0% B over 0.2 mins. Positive and negative electrospray ionization was employed.

Intermediates

Intermediate 1: 3-Ethyl-5-(6R-methoxy-2,2-dimethyl-tetrahydro-(3aR,6aR)-furo[3,4-d][1,3]dioxol-4S-yl)-isoxazole.

To a stirring mixture of 4R-ethynyl-6R-methoxy-2,2-dimethyl-tetrahydro-(3aR,6aR)-furo[3,4-d][1,3]dioxole [lit. compd.; ref *Helv. Chim. Acta* 1980, 63, 1181–1189.] (0.271 g, 1.37 mmol) and phenyl isocyanate (0.328 ml, 3.01 mmol) in dry toluene (1.5 ml) under nitrogen, a mixture of 1-nitropropane (0.134 ml, 1.51 mmol) and triethylamine (0.038 ml, 0.27 mmol) in dry toluene (1 ml) was added dropwise over 5 mins. A precipitate was formed slowly during the addition. The resultant mixture was heated at 73 to 82° C. for 18 h. The cooled reaction mixture was filtered through 3 ins. of silica gel, washed well with ether and then 40% ethyl acetate—cyclohexane. Removal of solvent in vacuo gave a light brown solid (0.487 g) which was subjected to flash column chromatography (20%, 25% then 30% ethyl acetate-cyclohexane) to give the title compound as a clear oil (0.329 g). TLC (40% ethyl acetate-cyclohexane, visualised in an iodine vapour tank) rf=0.49.

Intermediate 2

Intermediate 2a: Acetic acid 4R,5S-diacetoxy-2S-(3-ethyl-isoxazol-5-yl)-tetrahydro-furan-3R-yl ester and Intermediate 2b: acetic acid 4R,5R-diacetoxy-2S-(3-ethyl-isoxazol-5-yl)-tetrahydro-furan-3R-yl ester.

A solution of Intermediate 1 (0.355 g, 1.32 mmol) in a mixture of trifluoroacetic acid (5 ml) and water (0.05 ml) was stirred at room temperature for 27 h and then evaporated in vacuo. The residue was azeotroped with toluene (3×) and dissolved in dry dichloromethane (10 ml) under nitrogen and then cooled to 0° C. 4-(N,N-dimethylamino)pyridine (0.048 g, 0.4 mmol), triethylamine (8.3 ml, 60 mmol) followed by acetic anhydride (2.49 ml, 26.4 mmol) were added. Mixture was stirred at 0° C. to room temperature overnight. The resultant mixture was evaporated in vacuo to a brown liquid (1.34 g). Flash column chromatography (20%, 30% then 40% ethyl acetate-cyclohexane) afforded Intermediate 2a (0.192 g) as a light brown oil, TLC (40% ethyl acetate-cyclohexane, visualised with ammonium molydate stain reagent) rf=0.28and Intermediate 2b (0.16 g) as a light brown oil. TLC (40% ethyl acetate-cyclohexane, visualised with ammonium molydate stain reagent) rf=0.22.

Intermediate 3: Acetic acid 4R-acetoxy-2R-(2,6-dichloro-purin-9-yl)-5S-(3-ethyl-isoxazol-5-yl)-tetrahydro-furan-3R-yl ester.

To a mixture of Intermediate 2a and Intermediate 2b (0.909 g, 2.67 mmol) in dry acetonitrile (5 ml) at 0° C. under nitrogen was added 2,6-dichloropurine (0.779 g, 4.0 mmol), DBU (0.692 ml, 4.53 mmol) followed by trimethylsilyl triflate (0.99 ml, 5.06 mmol). The reaction was stirred at room temperature for 20 h, quenched with saturated aqueous sodium bicarbonate solution (30 ml). Extraction with ethyl acetate (3×40 ml) gave a brown liquid (3.54 g). Purification by flash column chromatography (40% then 50% ethyl acetate-cyclohexane) gave the title compound as a creamy white foam (0.798 g). TLC (60% ethyl acetate-cyclohexane, visualised with ammonium molydate stain reagent or under an UV lamp) rf=0.25.

Intermediate 4: (3aS,4S,6R,6aR)-6-[2-Chloro-6-(2,2-diphenyl-ethylamino)-purin-9-yl]-2,2-dimethyl-tetrahydro-furo[3,4-d][1,3]dioxole-4-carboxylic acid methoxy-methyl-amide.

Carbonyl di-imidazole (2.37 g, 14.6 mmol) was added to a stirring solution of (3aS,4S,6R,6aR)-6-[2-chloro-6-(2,2-diphenyl-ethylamino)-purin-9-yl]-2,2-dimethyl-tetrahydro-furo[3,4-d][1,3]dioxole-4-carboxylic acid (prepared by following the method of Preparation 4 in International Patent Application No. WO94/17090) (6.015 g, 11.23 mmol) in dry dichloromethane (30 ml) under nitrogen. Mixture was stirred for 1 h. A dichloromethane solution of N,O-dimethylhydroxylamine (25.8 mmol; generated by basification of a 10 ml aqueous solution of 2.57 g of the corresponding hydrochloride at 0° C. with aqueous sodium hydroxide, followed by extraction with 3×5 ml dichloromethane and dried over sodium sulphate) was added. Mixture was stirred at room temperature for 60 h, quenched with aqueous citric acid (10% w/v, 40 ml). Organic solution was separated, washed with aqueous sodium bicarbonate (8% w/v, 40 ml), dried (sodium sulphate) and filtered. Removal of solvent in vacuo gave the title compound as a creamy white foam (6.66 g). TLC (100% ethyl acetate, visualised under an UV lamp) rf=0.51.

Intermediate 5: 1-{6R-[2-Chloro-6-(2,2-diphenyl-ethylamino)-purin-9-yl]2,2-dimethyl-tetrahydro-(3aS,6aR)-furo[3,4-d][1,3]dioxol-4S-yl}-pent-2-yn-1-one.

A tetrahydrofuran solution of chloromagnesium ethylacetylide was generated by stirring a mixture of ethylacetylene (ca. 10 ml) and methylmagnesium chloride (3M in tetrahydrofuran, 8.7 ml, 26 mmol) under nitrogen at 0° C. to room temperature overnight. To this resultant grey gelatinous mixture under nitrogen and cooled at 0° C. was added a solution of Intermediate 4 (5.012 g, 8.66 mmol) in dry tetrahydrofuran (40 ml). Mixture was stirred at 0° C. for 4 h, quenched with saturated aqueous ammonia chloride solution (50 ml). The resultant mixture was extracted with ethyl acetate (3×50 ml), dried over magnesium sulphate and evaporated in vacuo to give the title compound as a creamy white foam (4.91 g).

TLC (7:3 ethyl acetate: cyclohexane, visualised under an UV lamp) rf=0.54.

Intermediate 6: 1-{6R-[2-Chloro-6-(2,2-diphenyl-ethylamino)-purin-9-yl]2,2-dimethyl-tetrahydro-(3aS,6aR)-furo[3,4-d][1,3]dioxol-4S-yl}-pentane-1,3-dione 3-oxime.

An aqueous solution of hydroxylamine (50 wt % in water, 0.019 ml, 0.304 mmol) was added to a stirring solution of Intermediate 5 (0.116 g, 0.203 mmol) in ethanol (0.5 ml) at room temperature. After stirring for 19 h, mixture was evaporated in vacuo. The resultant residue was partitioned in hydrochloric acid (0.1M, 5 ml) and ethyl acetate (10 ml). Aqueous solution was extracted with ethyl acetate (2×5 ml). Combined ethyl acetate extracts were dried over magnesium sulphate and evaporated in vacuo to give the title compound as a gummy solid (0.121 g). LC/MS System A Rt=4.78 mins, m/z 605 (MH$^+$ for $C_{31}H_{33}^{35}ClN_6O_5$).

Intermediate 7: (2R,3R,4S,5S)-2-[2-Chloro-6-(2,2-diphenyl-ethylamino)-purin-9-yl]-5-(3-ethyl-isoxazol-5-yl)-tetrahydro-furan-3,4-diol.

A solution of Intermediate 6 (0.12 g, 0.199 mmol) in a mixture of acetic acid (8 ml) and water (1 ml) was heated at 100° C. for 4.5 h. The cooled reaction mixture was evaporated in vacuo to give a brown gummy residue. Purification by flash column chromatography (50% then 70% ethyl acetate-cyclohexane) gave the title compound as a clear gummy solid (0.073 g). TLC (100% ethyl acetate, visualised under an UV lamp) rf=0.43.

Intermediate 8: Acetic acid 4R-acetoxy-2R-[2-chloro-6-(1-ethyl-propylamino)-purin-9-yl]-5S-(3-ethyl-isoxazol-5-yl)-tetrahydrofuran-3R-yl ester Intermediate 3 (0.518 g, 1.10 mmol), diisopropylethylamine (0.29 ml, 1.65 mmol) and 1-ethylpropylamine (0.14 ml, 1.21 mmol) was stirred in isopropanol at 50° C. for 21 hrs. Solvent was removed in vacuo leaving the title compound as a brown gum (0.528 g). TLC $SiO_2$ (cyclohexane, ethyl acetate, 1:1) Rf=0.19.

Intermediate 9: 2-Chloro-N-(1-Ethylpropyl)-adenosine

A mixture of 2,6-dichloro-9-(2,3,5-tri-O-acetyl-β-D-ribofuranosyl)-9H-purine ** (10.1 g, 22.6 mM), isopropanol (300 ml), $K_2CO_3$ (5 g) and 1-ethylpropylamine (2.17 g, 24.84 mM) was stirred at 20° C. for 24 hrs. The reaction mixture was heated at 54° C. for 73 hrs. Solvent was removed in vacuo, water (50 ml) was added, extracted with ethyl acetate (3×80 ml), the combined extracts were dried ($MgSO_4$) affording the title compound as a creamy light brown foam (9.44 g). LC/MS system A $R_t$=2.66 min, m/z= 372 MH$^+$.

** M. J. Robins and B. Uznanski, Canad. J. Chem., 1981, 59(17), 2608.

Intermediate 10: {6R-[2-Chloro-6-(1-ethyl-propylamino)-purin-9-yl]-2,2-dimethyl-tetrahydro-(3aR,6aR)-furo[3,4-d][1,3]dioxol-4R-yl}-methanol Intermediate 9 (9.300 g, 22.6 mol), 2,2-dimethoxypropane (35 ml) and para-toluenesulfonic acid (8.100 g) in acetone (250 ml) was stirred at 20° C. for 22 hrs. Solvent was removed in vacuo, ethyl acetate (200 ml) was added, washed with aqueous saturated $NaHCO_3$ (3×70 ml). Combined organics were extracted with ethyl acetate (50 ml) and the combined organics were dried ($MgSO_4$) and solvent was removed in vacuo. Purification using column chromatography on flash silica eluted with 50%, 60% then 70% ethyl acetate in cyclohexane furnished the title compound as a white foam (5.67 g). TLC $SiO_2$ (50% ethyl acetate in cyclohexane) Rf=0.17.

Intermediate 11: (3aS,4S,6R,6aR)-6-[2-Chloro-6-(1-ethyl-propylamino)-purin-9-yl]-2,2-dimethyl-tetrahydro-furo[3,4-d][1,3]dioxole-4-carboxylic acid To a vigorously stirred solution of Intermediate 10 (2.02 g, 4.9 mmol) in a mixture of ethyl acetate (76 ml) and saturated aqueous $NaHCO_3$ (51 ml) at 0° C. (pre-cooled for 30 mins.) containing KBr (0.059 g) and TEMPO (0.004 g), a solution freshly prepared from $NaHCO_3$ (0.156 g), aqueous NaOCl (2.7 ml, 13% active chlorine) and water (ca. 0.5 ml) was added dropwise over 10 mins. After 30 mins. and 2 hrs. further reagents were added (same amounts of KBr, TEMPO, $NaHCO_3$ and NaOCl in $H_2O$). Reaction mixture was poured onto a mixture of water (100 ml) and ethyl acetate (50 ml) containing $Na_2SO_3$ (10 g). The aqueous basic layer was cooled to 0° C., acidified to pH 2 and extracted with ethyl acetate (2×100 ml) and combined extracts dried ($MgSO_4$). The original organic layer was separated and washed with water (2×100 ml). The resultant aqueous wash was acidified to pH 3, extracted with ethyl acetate (2×50 ml) and combined extracts dried ($MgSO_4$). Combined dried organic extracts were evaporated in vacuo to yield the title compound as a white foam (1.309 g).

LC/MS SYSTEM B $R_t$=3.25 mins, m/z=426 MH$^+$.

Intermediate 12: (3aS,4S,6R,6aR)-6-[2-Chloro-6-(1-ethyl-propylamino)-purin-9-yl]-2,2-dimethyl-tetrahydro-furo[3,4-d][1,3]dioxole-4-carboxylic acid methoxy-methyl-amide Carbonyidiimidazole (0.348 g, 2.15 mmol) was added to a stirred solution of Intermediate 11 (0.700 g, 1.65 mmol) in dichloromethane (10 ml) at 20° C. under nitrogen. After 2 hrs. N,O-dimethylhydroxylamine (3.8 mmol, generated by extraction of an aqueous solution of the corresponding hydrochloride basified with aqueous 2N sodium hydroxide, with dichloromethane (3×1.5 ml), dried over $Na_2SO_4$) in dichloromethane (4.5 ml+0.5 ml rinse) was added. Mixture stirred at 20° C. over 3 days. Reaction diluted with dichloromethane (40 ml), washed with aqueous citric acid (40 ml, 10% w/v), aqueous saturated $NaHCO_3$ (40 ml), dried ($MgSO_4$) and solvent was removed in vacuo to yield the title compound as a white foam. (0.624 g). TLC $SiO_2$ (neat ethyl acetate, visualised by UV light) Rf=0.40.

Intermediate 13: 1-{6R-([2-Chloro-6-(1-ethyl-propylamino)-purin-9-yl]-2,2-dimethyl-tetrahydro-(3aS, 6aR)-furo[3,4-d][1,3]dioxol-4S-yl}-pent-2-yn-1-one Methyl magnesium chloride (1.9 ml, 5.69 mmol; 3 molar in THF) was added to excess ethylacetylene (ca. 3 ml) condensed into flask containing dry THF (1 ml) at −78° C. under nitrogen. The mixture was allowed to warm to 0° C. and stirred for 6 hrs. To the reaction mixture at 0° C. was cannulated Intermediate 12 (0.533 g, 1.14 mmol) in dry THF (6 ml). After 1 hr. at 0° C. saturated aqueous ammonium chloride (10 ml), extracted with ethyl acetate (3×10 ml), dried ($MgSO_4$) and solvent was removed in vacuo affording the title compound as a light brown gum (0.577 g). TLC $SiO_2$ (50% ethyl acetate in cyclohexane, visualised by UV light) Rf=0.33.

Intermediate 14: (2R,3R,4S,5S)-2-[2-Chloro-6-(1-ethyl-propylamino)-purin-9-yl]-5-(3-ethyl-isoxazol-5yl)-tetrahydro-furan-3,4-diol A mixture of Intermediate 13 (0.577 g, 1.25 mmol) and hydroxylamine (50 wt. % in $H_2O$, 0.13 ml, 1.88 mmol) in ethanol (3 ml) was stirred at 20° C. for 6 hrs. and allowed to stand at 20° C. for 3 days. Solvent was removed in vacuo and replaced with acetic acid (24 ml) and water (3 ml) which was heated to reflux for 2 h. and then at 100° C. for 3 h. The cooled reaction was evaporated to dryness and azeotroped with toluene (2×). Purification using column chromatography on flash silica eluted with 50%, 60% then 70% ethyl acetate in cyclohexane furnished the title compound as a light brown gum (0.413 g).

TLC SiO$_2$ (neat ethyl acetate, visualised by UV light) Rf=0.44.

Intermediate 15a and 15b: Acetic acid 2S,4R-diacetoxy-5R-ethynyl-tetrahydro-furan-3R-yl ester (Intermediate 15a) and Acetic acid 2R,4R-diacetoxy-5R-ethynyl-tetrahydro-furan-3R-yl ester (Intermediate 15b)

4R-Ethynyl-6R-methoxy-2,2-dimethyl-tetrahydro-(3aR,6aR)-furo[3,4-d][1,3]dioxole [lit. compd.; ref: Helv. Chim. Acta 1980, 63, 1181–1189.] (0.104 g, 0.53 mmol) was stirred in a mixture of water (0.2 mL) and trifluoroacetic acid (1.8 mL) for 1 h at room temperature. Removal of volatile matters in vacuo gave a residue. This was stirred with acetic anhydride (0.5 mL, 5.25 mmol), triethylamine (1.65 mL, 11.8 mmol) and 4-dimethylaminopyridine (0.019 g, 0.16 mmol) in dry dichloromethane (5 mL) at room temperature for 19.5 h. Mixture was evaporated in vacuo and then azeotroped with toluene (2×). The resultant dark brown residue was chromatographed on a SiO$_2$ column and eluted with 20% followed by 30% EtOAc-cyclohexane to give Intermediate 15a as a clear gum (0.039 g): TLC (50% EtOAc-cyclohexane, visualised with ammonium molydate staining solution) Rf=0.43.

and Intermediate 15b as a clear gum (0.038 g) which solidified to waxy needles on standing at room temperature: TLC (50% EtOAc-cyclohexane, visualised with ammonium molydate staining solution) Rf=0.36.

Intermediate 16: Acetic acid 4R-acetoxy-2R-(2,6-dichloro-purin-9-yl)-5R-ethynyl-tetrahydro-furan-3R-yl ester A mixture of Intermediate 15a and 15b (0.098 g, 0.36 mmol), 2,6-dichloropurine (0.106 g, 0.55 mmol) and DBU (0.094 mL, 0.62 mmol) in acetonitrile (0.7 mL) under N$_2$ was cooled 0° C. Trimethylsilyl triflate (0.135 mL, 0.69 mmol) was added dropwise. Mixture was allowed to warm to r.t. and stirred for 18.5 h. The reaction was quenched with saturated aqueous NaHCO$_3$ (5 mL), extracted with EtOAc (3×5 mL), dried (MgSO$_4$) and evaporated. The resultant brown residue was subjected to flash column chromatography (SiO$_2$/50% EtOAc-cyclohexane) to give the title product as a white solid (0.096 g). TLC (50% EtOAc-cyclohexane, visualised with ammonium molydate staining solution) Rf=0.25.

Intermediate 17: Acetic acid 4R-acetoxy-2R-[2-chloro-6-(1-ethyl-propylamino)-purin-9-yl]-5R-ethynyl-tetrahydro-furan-3R-yl ester A mixture of Intermediate 16 (1.111 g, 2.78 mmol), 1-ethylpropylamine (0.34 mL, 2.92 mmol) and di-isopropylethylamine (0.534 mL, 3.06 mmol) in DMF (10 mL) was heated at 50° C. for 17.5 h. Most DMF was removed by rotary-evaporation in vacuo. The resultant residue was diluted with saturated aqueous NaHCO$_3$ (30 mL). Extraction with EtOAc (50 mL then 2×25 mL) gave a brown foam (1.249 g). Purification using a Varian Mega Bonded Elut cartridge (10 g Si, 60 mL size) and eluted with 50% EtOAc-cyclohexane gave the title product as a light brown foam (1.135 g). TLC (50% EtOAc-cyclohexane, visualised under UV) Rf=0.29.

Intermediate 18: Acetic acid 4R-acetoxy-5S-(3-bromo-isoxazol-5-yl)-2R-[2-chloro-6-(ethyl-propylamino)-purin-9-yl]-tetrahydro-furan-3R-yl ester A mixture of dibromoformaldoxime (0.035 g, 0.17 mmol) and Intermediate 17 (0.052 g, 0.12 mmol) in ethyl acetate (4 mL) and water (0.2 mL) was stirred vigorously with solid sodium bicarbonate (0.11 g, 1.26 mmol) for 89 h at room temperature. More dibromoformaldoxime (0.035 g, 0.17 mmol), solid sodium bicarbonate (0.11 g, 1.26 mmol) and water (0.2 mL) were added. After a further 21 h, the reaction was diluted with water (5 mL), extracted with ethyl acetate (3×5 mL). Combined organic solution was evaporated in vacuo to give the crude product which was dissolved in toluene (2 mL). This solution was loaded onto a Varian Mega Bond Elut cartridge (5 g Si, 20 mL size) and eluted with 30%, 40%, 50%, 60% then 70% ethyl acetate-cyclohexane. Fractions containing the product were combined and evaporated to give the title compound as a light brown gum (0.043 g). LC/MS SYSTEM B Rt=3.66 mins, m/z=571 MH$^+$ for C$_{21}$H$_{24}$$^{79}$Br$^{35}$ClN$_6$O$_6$.

Intermediate 19: Acetic acid 4R-acetoxy-5S-(3-acetyl-isoxazol-5-yl)-2R-[2-chloro-6-(1-ethyl-propylamino)-purin-9-yl]-tetrahydro-furan-3R-yl ester Intermediate 19 was prepared in an analogous manner to Intermediate 18 using N-hydroxy-2-oxo-propionimidoyl chloride (0.021 g, 0.17 mmol). Further quantities of reagents were added at 89 h [N-hydroxy-2-oxo-propionimidoyl chloride (0.021 g, 0.17 mmol), solid sodium bicarbonate (0.11 g, 1.26 mmol) and water (0.2 mL)], 132 h [N-hydroxy-2-oxo-propionimidoyl chloride (0.05 g, 0.41 mmol) and solid sodium bicarbonate (0.11 g, 1.26 mmol)] and 180 h [N-hydroxy-2-oxo-propionimidoyl chloride (0.075 g, 0.62 mmol) and solid sodium bicarbonate (0.16 g, 1.26 mmol)]. After a further 24 h at r.t., the title product was isolated as a brown gum (0.043 g). LC/MS SYSTEM B Rt=3.51 mins, m/z=535 MH$^+$ for C$_{23}$H$_{27}$$^{35}$ClN$_6$O$_7$.

Intermediate 20: Acetic acid 4R-acetoxy-2R-[2-chloro-6-(1-ethyl-propylamino)-purin-9-yl]-5S-(3-methyl-isoxazol-5-yl)-tetrahydro-furan-3R-yl ester To a stirring mixture of Intermediate 17 (0.1 g, 0.22 mmol), triethylamine (0.031 mL, 0.22 mmol) and phenyl isocyanate (0.063 mL, 0.58 mmol) in dry toluene (1 mL) under N$_2$, a solution of nitroethane (0.021 mL, 0.29 mmol) in dry toluene (1 mL) was added. Mixture was heated at 80° C. for 21 h. The cooled reaction mixture was loaded onto a Varian Mega Bond Elut cartridge (5 g Si, 20 mL size), eluted with 30% to 60% EtOAc-cyclohexane. Fractions containing the product were pooled together and evaporated in vacuo. The resultant material was dissolved in toluene (2 mL), filtered through a plug of cotton wool and directly loaded onto another Varian Mega Bond Elut cartridge (5 g Si, 20 mL size). Elution with 20% EtOAc-cyclohexane (200 mL), 30% EtOAc-cyclohexane (100 mL). 40%, 50% and then 60% EtOAc-cyclohexane (50 mL each) gave the title product as a creamy white foam (0.099 g). LC/MS SYSTEM B Rt=3.47 mins, m/z=507 MH$^+$ for C$_{22}$H$_{27}$$^{35}$ClN$_6$O$_6$.

Intermediate 21: Acetic acid 4R-acetoxy-2R-[2-chloro-6-(1-ethyl-propylamino)-purin-9-yl]-5S-(3-propyl-isoxazol-5-yl)-tetrahydro-furan-3R-yl ester Intermediate 21 was prepared in an analogous manner to Intermediate 20 using nitrobutane (0.031 mL, 0.29 mmol). After 21 h, more phenyl isocyanate (0.063 mL, 0.58 mmol) and nitrobutane (0.031 mL, 0.29 mmol) in dry toluene (0.5 mL) were added. After a further 23 h at 80° C., the title product was isolated as a creamy white foam (0.093 g). LC/MS SYSTEM B Rt=3.68 mins, m/z=535 MH$^+$ for C$_{24}$H$_{31}$$^{35}$ClN$_6$O$_6$.

Intermediate 22: Acetic acid 4R-acetoxy-2R-[2-chloro-6-(1-ethyl-propylamino)-purin-9-yl]-5S-[3-(tetrahydro-pyran-2-yloxymethyl)-isoxazol-5-yl]-tetrahydro-furan-3R-yl ester Intermediate 22 was prepared in an analogous manner to Intermediate 20 using 2-(2-nitroethoxy)tetrahydropyran (0.045 mL, 0.29 mmol). Further quantities of reagents phenyl isocyanate (0.063 mL, 0.58 mmol) and 2-(2-nitroethoxy)tetrahydropyran (0.045 mL, 0.29 mmol) in dry toluene (0.5 mL) were added at 21 h. After a further 120 h at 80° C., the title product was isolated as a light brown foam (0.113 g). LC/MS SYSTEM B Rt=3.64 mins, m/z=607 MH$^+$ for C$_{27}$H$_{35}$$^{35}$ClN$_6$O$_6$.

Intermediate 23: (2R,3R,4S,5S)-2-[2-Chloro-6-(1-ethyl-propylamino)-purin-9-yl]-5-[3-(1-hydroxy-ethyl)-isoxazol-5-yl]-tetrahydro-furan-3,4-diol Sodium borohydride (12 mg, 0.31 mmol) was added to a stirring solution of Intermediate 19 (42 mg, 0.08 mmol) in methanol (1 mL) at 0° C. under nitrogen. After 4 h, reaction mixture was evaporated to give the title product as a light brown solid (0.057 g) in the isomeric ratio of 2:1. LC/MS SYSTEM A Rt=4.12 and 4.23 mins in the ratio 2:1 respectively, m/z=453 MH$^+$ for $C_{19}H_{25}{}^{35}ClN_6O_6$.

Intermediate 24: (2R,3R,4S,5S)-2-[2-Chloro-6-(1-ethyl-propylamino)-purin-9-yl]-5-(3-hydroxymethyl-isoxazol-5-yl)-tetrahydro-furan-3,4-diol trifluoroacetate A mixture of Intermediate 22 (0.061 g, 0.1 mmol) and sodium methoxide (25 wt % in methanol, 0.01 mL) in methanol (2 mL) was stirred at room temperature for 19 h. Acetic acid (0.1 mL) was added. Mixture was evaporated in vacuo. The resultant residue was dissolved in a mixture of TFA (0.9 mL) and water (0.1 mL) at 0° C. for 6 h. Removal of volatile matters gave the title product as a brown residue (0.19). LC/MS SYSTEM A Rt=4.05 mins, m/z=439 MH$^+$ for $C_{18}H_{23}{}^{35}Cl_6O_5$.

Intermediate 24 (Alternative Preparation): (2R,3R,4S,5S)-2-[2-Chloro-6-(1-ethyl-propylamino)-purin-9-yl]-5-(3-hydroxymethyl-isoxazol-5-yl)-tetrahydro-furan-3,4-diol trifluoroacetate To a methanol (3 ml) solution of Intermediate 34 (0.104 g, 0.2 mmol) was added 25% sodium methoxide in methanol solution (0.1 ml) and stirred for 30 mins. Acetic acid (0.1 ml) was added and evaporated to dryness. To the residue was added trifluoroacetic acid (1.8 ml) and water (0.2 ml). The mixture was stirred at 0° C. for 2 hours then evaporated to dryness to yield title compound as a brown solid (0.082 g). LC/MS SYSTEM C R$_t$=2.83 mins, m/z=439 MH$^+$.

Intermediate 25: (2R,3R,4S,5S)-2-[2-Chloro-6-(3-iodo-benzylamino)-purin-9-yl]-5-(3-ethyl-isoxazol-5-yl)-tetrahydro-furan-3,4-diol acetate A mixture of m-iodobenzylamine hydrochloride (0.032 g 0.12 mmol), diisopropylethylamine (0.046 ml) and Intermediate 3 (0.050 g 0.11 mmol) in isopropanol (2 ml) was heated to 50° C. for 24 h. Further addition of m-iodobenzylamine hydrochloride (0.032 g 0.12 mmol), diisopropylethylamine (0.22 ml) was made and the mixture heated to 50° C. for 8 h. Solvent was removed in vacuo and the residue dissolved in anhydrous methanol (2 ml) and treated with sodium methoxide (25% wt. solution in methanol, 0.25 ml) with stirring at 20° C. for 1 h., acetic acid (1 ml) was added and solvent was removed in vacuo. Purification using column chromatography on flash silica eluted with 50% cyclohexane in ethyl acetate furnished the title compound as a white solid after tituration with methanol (0.035 g). TLC SiO$_2$ (50% ethyl acetate in cyclohexane) Rf=0.17.

Intermediate 26: (2R,3R,4S,5S)-2-[2-Chloro-6-(1S-hydroxymethyl-2-phenyl-ethylamino)-purin-9-yl]-5-(3-ethyl-isoxazol-5-yl)-tetrahydro-furan-3,4-diol acetate A mixture of 3-(S)-(−)-2-amino-3-phenyl propanol (0.053 to 0.35 mmol), diisopropylethylamine (0.067 ml, 0.39 mmol and Intermediate 3 (0.152 g, 0.32 mmol) in isopropanol (2 ml) was heated to 50° C. for 17 h. Solvent was removed in vacuo the residue dissolved in anhydrous methanol (2 ml) and treated with sodium methoxide (25% wt. solution in methanol, 0.25 ml) with stirring at 20° C. for 1 h., acetic acid (0.5 ml) was added and solvent was removed in vacuo. Purification using column chromatography on flash silica eluted with ethyl acetate furnished the title compound as a crisp white foam (0.112 g). TLC SiO$_2$ (neat ethyl acetate) Rf=0.26.

Intermediate 27: 2(Pyridin-2-ylamino)-ethylamine

2-Bromopyridine (10.00 g, 63.3 mmol) was added dropwise to 1,2-diaminoethane (76.00 g, 126.6 mmol) under nitrogen at 20° C. with stirring. The reaction mixture was stirred at 20° C. for 4 h. and then under reflux for 24 h. The reaction mixture was concentrated in vacuo and purified by column chromatography on flash silica eluting with dichloromethane, ethanol and ammonia (30:8:1) to afford the title compound as a red oil (10.23 g). TLC SiO$_2$, (Dichloromethane, ethanol, ammonia; 30:8:1) Rf=0.14. Mass Spectrum m/z 138 (MH$^+$ for $C_6H_{11}N_3$).

Intermediate 28: (2R,3R,4S,5R)-2-{6-(1-Ethyl-propylamino)-2-[2-(1-methyl-1H-imidazol-4-yl)-ethylamino]-purin-9-yl}-5-ethynyl-tetrahydro-furan-3,4-diol A mixture of Intermediate 17 (0.45 g, 1.0 mmol), 1-methylhistamine (6.97 mmol: generated from 1.38 g of the corresponding bishydrochloride by neutralisation with 0.48 g solid sodium hydroxide in 5 mL methanol, filtered and evaporation in vacuo) and dis-isopropylethylamine (1 mL) in dry DMSO (3 mL) was heated at 95° C. for 114 h and then 110° C. for 71 h under nitrogen in a round-bottom flask. More 1-methylhistamine (6.97 mmol; generated from 1.38 g of the corresponding bishydrochloride as above) was added. After another 24 h the cooled reaction mixture was diluted with CH$_2$Cl$_2$, loaded onto a Varian Mega Bond Elut cartridge (10 g Si, 50 mL size). The cartridge was eluted under suction with CH$_2$Cl$_2$ (50 mL), Ethyl acetate (2×50 mL), 5%, 10% then 20% Methanol-Ethyl acetate (2×50 mL for each of the incremental increase). Eluates from CH$_2$Cl$_2$ to 10% Methanol-Ethyl acetate were combined and evaporated to an oil. Residual DMSO were removed under high vacuum. The resultant brown residue was dissolved in CH$_2$Cl$_2$ (30 mL) and filtered through another Varian Mega Bond Elut cartridge (10 g Si, 50 mL size). Elution with 50 mL of each of 50% to 90% Ethyl acetate-cyclohexane at 10% incremental increase, 100% Ethyl acetate followed by 10% Methanol-Ethyl acetate (4×50 mL), 15% Methanol-Ethyl acetate (2×50 mL), 20% Methanol-Ethyl acetate (2×50 mL) gave the title product as a light brown foam (0.126 g). LC/MS SYSTEM B R$_t$=2.10 mins, m/z=455 MH$^+$.

Intermediate 29: (2R,3R,4S,5S)-2-[2-Chloro-6-(1S-hydroxymethyl-2-methyl-propylamino)-purin-9-yl]-5-(3-ethyl-isoxazol-5-yl)-tetrahydro-furan-3,4-diol acetate L-2-Amino-3-methylbutanol (0.063 g 0.35 mmol), diisopropylethylamine (0.067 ml, 0.39 mmol) and Intermediate 3 (0.148 g, 0.32 mmol) in isopropanol (2 ml) was heated to 50° C. for 26 h. Solvent was removed in vacuo the residue dissolved in anhydrous methanol (2 ml) and treated with sodium methoxide (25% wt. solution in methanol, 0.25 ml) with stirring at 20° C. for 1.5 h., acetic acid (1 ml) was added and solvent was removed in vacuo. Purification using column chromatography on flash silica eluted with ethyl acetate followed by 10% methanol in ethyl acetate furnished the title compound as a cream coloured foam (0.126 g). TLC SiO$_2$ (neat ethyl acetate) Rf=0.21.

Intermediate 30: (3aS,4S,6R,6aR)-6-Methoxy-2,2-dimethyl-tetrahydro-furo[3,4-d][1,3]dioxole-4-carboxylic acid methoxy-methyl-amide To (3aS,4S,6R,6aR)-Methoxy-2,2-dimethyl-tetrahydro-furo[3,4-d][1,3]dioxole-4-carboxylic acid, prepared by following the method of Intermediate 1 in International Patent Application No. WO98/28319, (5.0 g, 22.9 mmol) in DCM (100 ml) was added carbonyldiimidazole (4.83 g, 29.8 mmol) in DCM (50 ml), portionwise, at room temperature, under nitrogen, and stirred for 1 hour. N,O-dimethylhydroxylamine hydrochloride (4.47 g, 45.8 mmol)

was dissolved in 2.0M sodium hydroxide solution (100 ml) and extracted with DCM (2×50 ml). The organic extracts were combined, added to the original reaction mixture and stirred for 24 h. Solvent was removed by evaporation and the resulting residue taken into ethyl acetate (150 ml), washed with saturated citric acid (50 ml), sat. sodium bicarbonate (50 ml), sat. brine (100 ml) and dried (MgSO$_4$). The solvent was removed in vacuo to furnish the title compound as a pale brown oil (5.786 g). Mass spectrum m/z=262 (MH$^+$ for C$_{11}$H$_{19}$NO$_6$).

Intermediate 31: 1-(6R-Methoxy-2,2-dimethyl-tetrahydro-(3aS,6aR)-furo[3,4-d][1,3]dioxol-4S-yl)-4-(tetrahydro-pyran-2-yloxy)-but-2-yn-1-one To a THF solution (20 ml) of tetrahydro-2-(2-propanyloxy)-2H-pyran (1.609 g, 11.48 mmol) was added n-butyllithium 1.6M in hexanes (7.7 ml, 11.48 mmol), at −78° C. under nitrogen, and stirred for 20 mins. Boron trifluoride diethyl etherate (1.79 g, 12.61 mmol) was added and the solution stirred for 30 mins. An anhydrous THF solution (2 ml) of Intermediate 30 (1.0 g, 3.82 mmol) was added and the mixture stirred at −78° C., under nitrogen, for 3 hours. The reaction was quenched with sat. ammonium chloride solution (100 ml) and extracted with ethyl acetate (3×100 ml). The combined organic layers were dried (MgSO$_4$) and solvent removed in vacuo to give a crude product as a brown oil (2.52 g). A portion of this crude product (0.5 g) was purified using flash column chromatography (Biotage, pre-packed 40 g SiO$_2$) eluted with 10% ethyl acetate in cyclohexane to yield the title compound as a colourless oil (0.182 g). Mass spectrum m/z=341 (MH$^+$ for C$_{17}$H$_{24}$O$_7$).

Intermediate 32: Acetic acid 4R-acetoxy-2S-(3-acetoxymethyl-isoxazol-5yl)-5R-methoxy-tetrahydrofuran-3R-yl ester To a methanol solution (30 ml) of Intermediate 31 (3.18 g, 9.34 mmol) was added 50 wt % hydroxylamine in water (1.15 ml, 18.6 mmol) and the mixture stirred under nitrogen at room temperature for 16 hours. Solvent was removed by evaporation to give a yellow oil (3.4 g). A portion (1.0 g) of this intermediate was dissolved in methanol (30 ml), acidified with 37% hydrochloric acid solution (1 ml) and stirred, under nitrogen, for 24 hours at 50° C. and a further 16 hours at reflux. The reaction was cooled, diluted with methanol (30 ml), 50% of solvent removed by evaporation and replaced with pyridine (2 ml) and toluene (30 ml). The mixture evaporated to dryness to give a dark brown/black viscous oil. To this residue was added pyridine(20 ml), 4N,N-dimethylaminopyridine and acetic anhydride (4 ml). The mixture was stirred for 3 hours, solvent removed by evaporation, residue taken into DCM (150 ml), washed with sat. citric acid solution (50 ml), 8% sodium bicarbonate solution (100 ml), brine (100 ml) and dried (MgSO$_4$). Solvent was removed in vacuo and the residue was purified using flash column chromatography (Biotage, pre-packed 40 g SiO$_2$) eluted with ethyl acetate, cyclohexane (2:1) to yield the title compound as a yellow oil (0.841 g). TLC SiO$_2$ (neat ethyl acetate) Rf=0.66.

Intermediate 33: Acetic acid 4R-acetoxy-5S-(3-acetoxymethyl-isoxazol-5-yl)-2R-(2,6-dichloro-purin-9-yl)-tetrahydro-furan-3R-yl ester To 2,6-dichloropurine (0.158 g, 0.84 mmol) was added HMDS (5 ml) and mixture stirred under nitrogen for 16 hours at 100° C. Reaction was cooled, solvent removed by evaporation, azeotroped with anhydrous toluene (5 ml) and evaporated to dryness to give a white amorphous solid. To this solid was added anhydrous acetonitrile (1.35 ml) solution Intermediate 32 (0.100 g, 0.279 mmol) and further anhydrous acetonitrile (2 ml). The mixture was cooled to 0° C. and TMSOTf (0.165 ml, 0.92 mmol) added with stirring. The mixture was allowed to warm to room temperature over 20 mins, and heated with stirring at 80° C. for 20 hours. Reaction was cooled and poured into 8% sodium bicarbonate solution (20 ml), extracted with ethyl acetate (2×30 ml), dried (MgSO$_4$) and evaporated to afford a brown gum. Purification using flash column chromatography (Biotage, prepacked 8 g SiO$_2$) eluted with 1:1 ethyl acetate cyclohexane to furnish title compound as a white crystalline solid (0.140 g). TLC SiO$_2$ (neat ethyl acetate) Rf=0.55.

Intermediate 34: Acetic acid 4R-acetoxy-5S-(3-acetoxymethyl-isoxazol-5-yl)-2R-[2-chloro-6-(1-ethyl-propylamino)-purin-9-yl]-tetrahydro-furan-3R-yl ester To an isopropylalcohol (5 ml) solution of Intermediate 33 (0.100 g, 0.194 mmol) was added 1-ethylpropylamine (0.025 g, 0.29 mmol) and N,N-diisopropylethylamine (0.033 g, 0.252 mmol). The mixture was heated with stirring at 50° C. for 16 hours and solvent removed by evaporation to yield title compound as a yellow gum (0.104 g). LC/MS SYSTEM C R$_t$=3.50 min, m/z=565 MH$^+$.

Intermediate 35: 1-(6R-Methoxy-2,2-dimethyl-tetrahydro-(3aS,6aR)-furo[3,4-d][1,3]dioxol-4S-yl)-pent-2-yn-1-one 1-Butyne (ca. 20 ml) was condensed into a flask at −78° C. under nitrogen and to this was added THF (140 ml) followed by methyl magnesium chloride (25 ml, 75 mol, 3M in THF) added over 10 mins. The mixture was allowed to warm to ambient temperature and stirred for 5 hrs. The solution was cooled to 0–5° C. and Intermediate 30 (21.07 g, 80.73 mmol) was added in THF (40 ml) over 20 mins. The solution was stirred for 1 hr. at 0–5° C. and then left to stand at 4 C overnight. To a stirred solution at 0–5 C was added 30% ammonium chloride (200 ml) followed by 2M hydrochloric acid (150 ml) and extraction with ethyl acetate (2×200 ml). The combined organic layers were dried (Na$_2$SO$_4$), solvent was removed in vacuo and purification using column chromatography on flash silica eluted with a hexane, ethyl acetate mixture (4:1) afforded the title compound as a white solid (13.76 g).

TLC SiO$_2$ (20% ethyl acetate in hexane) Rf=0.35.

Intermediate 36: 1-(6R-Methoxy-2,2-dimethyl-tetrahydro-(3aS,6aR)-furo[3,4-d][1,3]dioxol-4S-yl)-pentane-1,3-dione 3-oxime Intermediate 35 (15.02 g, 59.1 mmol) in methanol (300 ml) was treated with hydroxylamine (50% aqueous solution, 7.20 ml, 235.2 mmol) and stirred at 22 C for 5 hrs. The solution was concentrated and the resultant white solid was taken up in ethyl acetate (500 ml), washed with water (100 ml) and brine (100 ml), dried (Na$_2$SO$_4$) and solvent was removed in vacuo leaving the title compound as a white solid dried overnight under high vacuum (15.81 g). TLC SiO$_2$ (diethyl ether, hexane) Rf=0:10.

Intermediate 37: 2-(2-Piperidin-1-yl-ethylamino)-1,9-dihydro-purin-6-one

A mixture of 2-bromohypoxanthine (6 g, 28 mmol) and 2-piperidinoethylamine (7 ml, 56 mmol) in 2-methoxyethanol (30 ml) was heated to reflux overnight. The mixture was cooled to ambient temperature, giving rise to a yellow precipitate. Additional precipitate was generated on addition of water (50 ml). After stirring for 1 hour, the suspension was filtered and the solid obtained was washed with water and dried under vacuum to give the title compound (5.6 g). LC/MS SYSTEM C R$^t$=0.82 mins, m/z=263 MH$^+$.

Intermediate 38: (6-Chloro-9H-purin-2-yl)-(2-piperidin-1-yl-ethyl)-amine

A mixture of N,N-dimethylaniline (4 ml, 31 mmol) and phosphorus oxychloride (30 ml, 314 mmol) was stirred at ambient temperature for 10 min before Intermediate 37 (5.5 g, 20 mmol) was added portionwise and was then refluxed for 15 min. On cooling the phosphorus oxychloride was evaporated in vacuo, the residue obtained was azeotroped with toluene (3×50 ml). Purification using flash column chromatography with a Biotage column (90 g, $SiO_2$) eluting with 10% methanol/chloroform 1% ammonia gave the title compound as a pale yellow solid (4.980 g). LC/MS SYSTEM C $R_t$=1.61 min, m/z=281 $MH^+$.

Intermediate 39: N6-(2,2-Diphenyl-ethyl)-N2-(2-piperidin-1-yl-ethyl)-9H-purine-2,6-diamine A mixture of Intermediate 38 (5.000 g, 17.8 mmol), 2,2-diphenylethylamine (5.200 g, 27 mmol) and N,N-diisopropylethylamine (6.2 ml, 36 mmol) in isopropanol (100 ml) was heated to reflux overnight. Upon cooling the solvent was removed in vacuo and the residue was purified using flash column chromatography with a Biotage column (90 g, $SiO_2$) eluting with 5% methanol/chloroform/1% ammonia gave the title compound as an off white solid (4.500 g).

LC/MS SYSTEM C $R_t$=2.47 min, m/z=442 $MH^+$.

Intermediate 40: Acetic acid 4R-acetoxy-2S-(3-ethyl-isoxazol-5-yl)-5R-methoxy-tetrahydrofuran-3R-yl ester Intermediate 36 (15.769 54.91 mmol) in methanol (400 ml) was treated with concentrated hydrochloric acid (25 ml) and heated to reflux for 22 hrs. The solution was concentrated under reduced pressure and co-evaporated with methanol/toluene (×2). The residue was dissolved in DCM (200 ml) and treated with pyridine (100 ml), acetic anhydride (30 ml, 318 mmol and DMAP (0.064 g) and stirred at ambient temperature for 16 hrs. The reaction mixture was diluted with DCM (200 ml) and washed with 8% sodium bicarbonate (400 ml), 2M hydrochloric acid (3×300 ml). The aqueous layer was extracted with DCM (100 ml) and the combined organic layers were dried ($Na_2SO_4$) and solvent was removed in vacuo leaving a brown residue. Purification using column chromatography on flash silica eluted with hexane, ethyl acetate (1:1) afforded the title compound as an orange coloured oil (5.710 g). TLC $SiO_2$ (50% ethyl acetate in hexane) Rf=0.38.

Intermediate 41: Acetic acid 4S-acetoxy-5S-[6-(2,2-diphenyl-ethylamino)-2R-(2-piperidin-1-yl-ethylamino)-purin-9-yl]-2-(3-ethyl-isoxazol-5-yl)-tetrahydro-furan-3R-yl ester A suspension of Intermediate 39 (0.500 g, 1 mmol) in HMDS (5 ml) was heated to reflux for 3.5 hours whereupon the solvent was removed in vacuo. The residue obtained was azeotroped with anhydrous toluene (3×5 ml). To the residue in acetonitrile (2 ml) was added Intermediate 40 (0.420 g, 1.3 mmol) and 1,8-diazabicyclo[5.5.0]undec-7-ene (0.16 ml, 1 mmol). The mixture was cooled to 0° C. and the TMSOTf (0.6 ml, 3.3 mmol) was added. The mixture was allowed to warm to room temperature, and then heated to reflux overnight. On cooling the mixture was poured into saturated bicarbonate solution (10 ml) and extracted with ethyl acetate (3×15 ml). The combined organic layers were washed with water (10 ml), dried ($MgSO_4$) and the solvent removed in vacuo. Purification using flash column chromatography with a Biotage column (8 g, $SiO_2$) eluting with 5% methanol/chloroform/1% ammonia furnished the title compound as a light brown solid (0.198 g). LC/MS SYSTEM C $R_t$=2.89 min, m/z=722 $MH^+$.

EXAMPLES

Example 1

(2R,3R,4S,S)-2-[6-(2,2-Diphenyl-ethylamino)-2-(2-piperidin-1-yl-ethylamino)-purin-9-yl]-5-(3-ethyl-isoxazol-5-yl)-tetrahydro-furan-3,4-diol diformate A mixture of Intermediate 3 (0.02 g, 0.043 mmol), 2,2-diphenylethylamine (0.1 mmol/ml in isopropanol, 0.581 ml, 0.058 mmol) and diisopropylethylamine (0.2 mmol/ml in isopropanol, 0.345 ml, 0.069 mmol) in a sealed vial (e.g. Reacti-vial™) was heated at 53° C. for 16 h. Volatile matters were blown off under a jet of nitrogen. 2-Piperidin-1-yl-ethylamine (0.044 g, 0.344 mmol) and DMSO (0.2 ml) were added to the resultant residue. Mixture was heated at 92° C. for 4 days. The resultant crude product was purified by autoprep. HPLC to afford the title compound after freeze-drying as a pale brown solid (0.0029 g). LC/MS SYSTEM B $R_t$=4.24 mins, m/z=639 $MH^+$.

We envisage an alternative process for preparation of Example 1 which comprises reacting Intermediate 7 with 2-piperidin-1-yl-ethylamine in DMSO at elevated temperature.

Example 1 (Alternative Preparation)

2R-[6-(2,2-Diphenyl-ethylamino)-2-(2-piperidin-1-yl-ethylamino)-purin-9-yl]-5S-(3-ethyl-isoxazol-5-yl)-tetrahydro-furan-3R,4S-diol trifluoroacetate A solution of Intermediate 41 (0.125 g, 0.1 mmol) in 10% ammonia in methanol (5 ml) was stirred at room temperature overnight. The solvent was evaporated in vacuo and purification of the residue with preparative HPLC (gradient 5–95% acetonitrile) afforded the title compound (0.100 g).

LC/MS SYSTEM C $R_t$=2.77 min, m/z=639 $MH^+$.

Example 2

(2R,3R,4S,5S)-2-[6-(2,2-Diphenyl-ethylamino)-2-(2-morpholin-4-yl-ethylamino)-purin-9-yl]-5-(3-ethyl-isoxazol-5-yl)-tetrahydro-furan-3,4-diol diformate.

Example 2 was prepared in an analogous manner to Example 1 using 2-(morpholin-4-yl)-ethylamine (0.045 g. 0.344 mmol). The title compound was afforded after freeze-drying as a brown solid (0.01 g). LC/MS SYSTEM B $R_t$=4.07 mins, m/z=641 $MH^+$.

Example 3

(2R,3R,4S,5S)-2-(3-Ethyl-isoxazol-5-yl)-5-[6-phenethylamino-2-(2-piperidin-1-yl-ethylamino)-purin-9-yl]-tetrahydro-furan-3,4-diol diformate Example 3 was prepared in an analogous manner to Example 1 using phenethylamine (0.1 mmol/ml in isopropanol, 0.581 ml, 0.058 mmol) and 2-(2-piperidin-1-yl)-ethylamine (0.045 g, 0.344 mmol). A mixture of Intermediate 3 (0.02 g, 0.043 mmol), phenethylamine (0.1 mmol/ml in isopropanol, 0.581 ml, 0.058 mmol) and diisopropylethylamine (0.2 mmol/ml in isopropanol, 0.345 ml, 0.069 mmol) in a sealed vial (e.g. Reacti-vial™) was heated at 53° C. for 16 h. Volatile matters were blown off under a jet of nitrogen. 2-Piperidin-1-yl-ethylamine (0.045 g, 0.344 mmol) and DMSO (0.2 ml) were added to the resultant residue. The mixture was heated at 92° C. for 4 days. The resultant crude product was purified by autoprep. HPLC to afford the title compound after freeze-drying as a brown solid (0.004 g).

LC/MS SYSTEM B $R_t$=3.90 mins, m/z=563 $MH^+$.

Example 4

(2R,3R,4S,5S)-2-[6-(2,2-Diphenyl-ethylamino)-2-(2-hydroxy-ethylamino)-purin-9-yl]-5-(3-ethyl-isoxazol-5-yl)-tetrahydro-furan-3,4-diol formate A mixture of Intermediate 3 (0.044 g/ml, 0.5 ml, 0.047 mmol), 2,2-diphenylethylamine (0.011 g, 0.056 mmol) and diisopropylethylamine (0.013 ml, 0.074 mmol) was heated in a sealed vial (e.g., Reacti-vial™) at 53° C. for 16 h. Volatile matters were blown off under a jet of nitrogen. Ethanolamine (0.017 g, 0.28 mmol) was added. DMSO (0.1 ml) was added to the residue. Mixture was heated at 90° C. for 5 days. The resultant crude product was purified by autoprep. HPLC to afford the title compound after freeze-drying as a brown solid (0.007 g).

LC/MS SYSTEM B $R_t$=2.98 mins, m/z=572 MH$^+$.

Example 5

(2S,3S,4R,5R)-2-(3-Ethyl-isoxazol-5-yl)-5-{6-(1-ethyl-propylamino)-2-[2-(1-methyl-1H-imidazol-4-yl)-ethylamino]-purin-9-yl}-tetrahydro-furan-3,4-diol diformate Example 5 was prepared in an analogous manner to Example 4 using 1-ethylpropylamine (0.005 g, 0.056 mmol) and 2-(1-methyl-1H-imidazol-4-yl)ethylamine (0.035 g, 0.28 mmol; generated from the corresponding bishydrochloride by neutralisation with slight deficient of solid sodium hydroxide in methanol and evaporation of any volatile matters under a jet of nitrogen) at 90° C. for 5 days. The title compound was afforded after freeze-drying as a pale brown solid (0.009 g). LC/MS SYSTEM A $R_t$=3.61 mins, m/z=526 MH$^+$.

Example 6

(2S,3S,4R,5R)-2-(3-Ethyl-isoxazol-5-yl)-5-[6-(1-ethyl-propylamino)-2-(2-piperidin-1-yl-ethylamino)-purin-9-yl]-tetrahydro-furan-3,4-diol diformate Example 6 was prepared in an analogous manner to Example 4 using 1-ethylpropylamine (0.005 g, 0.056 mmol) and 2-(2-piperidin-1-yl)-ethylamine (0.036 g, 0.28 mmol) at 90° C. for 5 days. A mixture of Intermediate 3 (0.044 g/ml, 0.5 ml, 0.047 mmol), 1-ethylpropylamine (0.005 g, 0.056 mmol) and diisopropylethylamine (0.013 ml, 0.074 mmol) was heated in a sealed vial (e.g., Reacti-via™) at 53° C. for 16 h. Volatile matters were blown off under a jet of nitrogen. 2-Piperidin-1-yl-ethylamine (0.036 g, 0.28 mmol) DMSO (0.1 ml) were added to the residue. The mixture was heated at 90° C. for 5 days. The resultant crude product was purified by autoprep. HPLC to afford the title compound after freeze-drying as a brown solid (0.004 g).

LC/MS SYSTEM A $R_t$=3.76 mins, m/z=529 MH$^+$.

Example 7

(2R,3R,4S,5S)-2-{6-(3,3-Dimethyl-butylamino)-2-[2-(1-methyl-1H-imidazol-4-yl)-ethylamino]-purin-9-yl}-5-(3-ethyl-isoxazol-5-yl)-tetrahydro-furan-3,4-diol diformate Example 7 was prepared in an analogous manner to Example 4 using 3,3-dimethylbutylamine (0.006 g, 0.056 mmol) and 2-(1-methyl-1H-imidazol-4-yl)ethylamine (0.035 g, 0.28 mmol; generated as in Example 5) at 90° C. for 5 days. The title compound was afforded after freeze-drying as a brown solid (0.007 g). LC/MS SYSTEM A $R_t$=3.80 mins, m/z=540 MH$^+$.

Example 8

(2S,3S,4R,5R)-2-(3-Ethyl-isoxazol-5-yl)-5-[6-(cyclopentylamino)-2-(2-piperidin-1-yl)-ethylamino)-purin-9-yl]-tetrahydro-furan-3,4-diol diformate Example 8 was prepared in an analogous manner to Example 4 using cyclopentylamine (0.005 g, 0.056 mmol) and 2-piperidin-1-yl-ethylamine (0.036 g, 0.28 mmol) at 90° C. for 5 days. The title compound was afforded after freeze-drying as a brown solid (0.003 g). LC/MS SYSTEM A $R_t$=3.44 mins, m/z=527 MH$^+$.

Example 9

N-{2-[9-[5S-(3-Ethyl-isoxazol-5-yl)-3R,4S-dihydroxy-tetrahydro-furan-2R-yl]-6-tetrahydro-thiopyran-4-ylamino)-9H-purin-2-ylamino]-ethyl}-guanidine diformate A mixture of Intermediate 3 (0.15 g, 0.32 mmol), tetrahydro-thiopyran-4-ylamine (0.041 g, 0.35 mmol) and diisopropylethylamine (0.139 ml, 0.8 mmol) in isopropanol (2.5 ml) was heated in a sealed vial (e.g., Reacti-vial™) at 50° C. for 19 h. Volatile matters were blown off under a jet of nitrogen. The resultant residue was dissolved in DMSO (0.6 ml). One-sixth volume of this solution was transferred to another sealed vial and ethylenediamine (0.021 ml, 0.32 mmol) was added. The mixture was heated at 90–92° C. for 3 days, cooled to room temperature and diluted with 50% aqueous ethanol (0.5 ml). 1H-Pyrazole carboxamidine hydrochloride (0.016 g, 0.11 mmol) and imidazole (0.007 g, 0.11 mmol) were added. Mixture was heated at 60° C. for 4 days. More 1H-pyrazole carboxamidine hydrochloride (0.016 g, 0.11 mmol) and imidazole (0.007 g, 0.11 mmol) were added. Heating was continued for another 4 days. Volatile matters were then blown off under a jet of nitrogen. The resultant crude product was purified by autoprep. HPLC to afford the title compound after freeze-drying as a light brown solid (0.003 g). LC/MS SYSTEM B $R_t$=2.47 mins, m/z=533 MH$^+$.

Example 10

(2S,3S,4R,5R)-2-(3-Ethyl-isoxazol-5-yl)-5-[6-(3-fluoro-4-hydroxy-phenylamino)-2-(2-piperidin-1-yl-ethylamino)-purin-9-yl]-tetrahydro-furan-3,4-diol diformate A mixture of Intermediate 3 (0.15 g, 0.32 mmol), 3-fluoro-4-hydroxyaniline (0.045 g, 0.35 mmol) and diisopropylethylamine (0.139 ml, 0.8 mmol) in isopropanol (2.5 ml) was heated in a sealed vial (e.g., Reacti-vial™) at 5° C. for 19 h. Volatile matters were blown off under a jet of nitrogen. The resultant residue was dissolved in DMSO (0.6 ml). One-sixth volume of this solution was transferred to another sealed vial and 2-piperidin-1-yl-ethylamine (0.041 g, 0.32 mmol) was added. The mixture was heated at 90–92° C. for 4 days. The resultant crude product was purified by autoprep. HPLC to afford the title compound after freeze-drying as a whitish light brown solid (0.01 g).

LC/MS SYSTEM A $R_t$=3.53 mins, m/z=569 MH$^+$.

Example 11

2-[9-[5S-(3-Ethyl-isoxazol-5-yl)-3R,4S-dihydroxy-tetrahydro-furan-2R-yl]-2-(2-piperidin-1-yl-ethylamino)-9H-purin-6-ylamino]-ethanesulfonic acid methylamide diformate Example 11 was prepared in an analogous manner to Example 10 using 2-aminoethylsulfonic acid, methylamide (0.048 g, 0.35 mmol) and 2-piperidin-1-yl-ethylamine (0.041 g, 0.32 mmol) at 90° C. for 4 days. The title compound was afforded after freeze-drying as a whitish brown solid (0.011 g).

LC/MS SYSTEM A $R_t$=3.41 mins, m/z=580 MH$^+$.

Example 12

(2S,3S,4R,5R)-2-(3-Ethyl-isoxazol-5-yl)-5-[2-(2-piperidin-1-yl-ethylamino)-6-(tetrahydro-thiopyran-4-ylamino)-purin-9-yl]-tetrahydro-furan-3,4-diol diformate Example 12 was prepared in an analogous manner to Example 10 using tetrahydro-thiopyran-4-ylamine (0.041 g, 0.35 mmol) and 2-piperidin-1-yl-ethylamine (0.041 g, 0.32 mmol) at 90° C. for 3 days. The title compound was afforded after freeze-drying as a whitish brown solid (0.01 1 g). LC/MS SYSTEM B $R_t$=2.33 mins, m/z=559 MH$^+$.

Example 13

(2S,3S,4R,5R)-2-(3-Ethyl-isoxazol-5-yl)-5-[2-(2-pyridin-2-yl-ethylamino)-6-(tetrahydro-pyran-4-ylamino)-purin-9-yl]-tetrahydro-furan-3,4-diol diformate Example 13 was prepared in an analogous manner to Example 10 using tetrahydropyran-4-ylamine (0.035 g, 0.35 mmol) and 2-pyridin-2-yl-ethylamine (0.039 g, 0.32 mmol) at 90° C. for 10 days. The title compound was afforded after freeze-drying as a brown solid (0.013 g). LC/MS SYSTEM B $R_t$=2.21 mins, m/z=537 MH$^+$.

Example 14

(2S,3S,4R,5R)-2-(3-Ethyl-isoxazol-5-yl)-5-[2-(2-piperidin-1-yl-ethylamino)-6-(tetrahydro-pyran-4-ylamino)-purin-9-yl]-tetrahydro-furan-3,4-diol diformate Example 14 was prepared in an analogous manner to Example 10 using tetrahydropyran-4-ylamine (0.035 g, 0.35 mmol) and 2-piperidin-1-yl-ethylamine (0.041 g, 0.32 mmol) at 90° C. for 3 days. The title compound was afforded after freeze-drying as a brown solid (0.004 g). LC/MS SYSTEM B $R_t$=2.17 mins, m/z=543 MH$^+$.

Example 15

(2S,3S,4R,5R)-2-(3-Ethyl-isoxazol-5-yl)-5-[2-(1S-hydroxymethyl-2-phenyl-ethylamino)-6-(tetrahydro-pyran-4-ylamino)-purin-9yl]-tetrahydro-furan-3,4-diol formate Example 15 was prepared in an analogous manner to Example 10 using tetrahydropyran-4-ylamine (0.035 g, 0.35 mmol) and (S)-(−)-2-amino-3-phenyl-1-propanol (0.048 g, 0.32 mmol) at 90° C. for 12 days. The title compound was afforded after freeze-drying as a yellowish brown solid (0.015 g).

LC/MS SYSTEM B $R_t$=2.64 mins, m/z=566 MH$^+$.

Example 16

(2R,3R,4S,5S)-2-{6-(2,2-Diphenyl-ethylamino)-2-[2-(pyridin-2-ylamino)-ethylamino]-purin-9-yl}-5-(3-ethyl-isoxazol-5-yl)-tetrahydro-furan-3,4-diol diformate Example 16 was prepared in an analogous manner to Example 1 using 2-(pyridin-2-ylamino)-ethylamine (0.047 g, 0.344 mmol) at 92° C. for 4 days. The title compound was afforded after freeze-drying as a brown solid (0.004 g). LC/MS SYSTEM B $R_t$=4.27 mins, m/z=648 MH$^+$.

Example 17

(2R,3R,4S,5S)-2-[6-(2,2-Diphenyl-ethylamino)-2-(1S-hydroxymethyl-2-phenyl-ethylamino)-purin-9-yl]-5-(3-ethyl-isoxazol-5-yl)-tetrahydro-furan-3,4-diol formate Example 17 was prepared in an analogous manner to Example 1 using (S)-(−)-2-amino-3-phenyl-1-propanol (0.104 g, 0.688 mmol) at 92° C. for 9 days. The title compound was afforded after freeze-drying as a brown solid (0.0054 g).

LC/MS SYSTEM B $R_t$=4.67 mins, m/z=662 MH$^+$.

Example 18

4-(2-{6-Amino-9-[5S-(3-ethyl-isoxazol-5-yl)-3R,4S-dihydroxy-tetrahydro-furan-2R-yl]-9H-purin-2-ylamino}-benzenesulfonamide formate To a stirring solution of Intermediate 3 (0.13 g, 0.28 mmol) in tetrahydrofuran (10 mL) at −78° C. under nitrogen, gaseous ammonia (ca. 20 mL) was condensed into the reaction. Reaction mixture was stirred at room temperature overnight, evaporated in vacuo to a yellow foam (0.153 g). One-sixth of this material (0.0255 g) was heated with 4-(2-aminoethyl)benzenesulfonamide (0.069 g, 0.344 mmol) in DMSO (0.2 ml) at 92° C. for 4 days. The resultant crude product was purified by autoprep. HPLC to afford the title compound after freeze-drying as a pale brown solid (0.002 g). LC/MS SYSTEM B $R_t$=3.47 mins, m/z=531 MH$^+$.

Example 19

(2R,3R,4S,5S)-2-[2-(trans-4-Amino-cyclohexylamino)-6-(2,2-diphenyl-ethylamino)-purin-9-yl]-5-(3-ethyl-isoxazol-5-yl)-tetrahydro-furan-3,4-diol diformate Example 19 was prepared in an analogous manner to Example 4 using trans-cyclohexane-1,4-diamine (0.032 g, 0.28 mmol) at 90° C. for 5 days. The title compound was afforded after freeze-drying as a pale brown solid (0.005 g).

LC/MS SYSTEM B $R_t$=2.62 mins, m/z=625 MH$^+$.

Example 20

(2S,3S,4R,5R)-2-(3-Ethyl-isoxazol-5-yl)-5-{6-(3-iodo-benzylamino)-2-[2-(1-methyl-1H-imidazol-4-yl)-ethylamino]-purin-9-yl}-tetrahydro-furan-3,4-diol diformate Example 20 was prepared in an analogous manner to Example 4 using 3 iodobenzylamine (0.013 g, 0.056 mmol) and 2-(1-methyl-1H-imidazol-4-yl)ethylamine (0.035 g, 0.28 mmol; generated from the corresponding bishydrochloride by neutralisation with slight deficient of solid sodium hydroxide in methanol and evaporation of any volatile matters under a jet of nitrogen) at 90° C. for 5 days. The title compound was afforded after freeze-drying as a pale brown solid (0.011 g). LC/MS SYSTEM A $R_t$=3.64 mins, m/z=672 MH$^+$.

Example 21

(2R,3R,4S,5S)-2-{6-(2-Cyclohexyl-ethylamino)-2-[2-(1-methyl-1H-imidazol-4-yl)-ethylamino]-purin-9-yl}5-(3-ethyl-isoxazol-5-yl)-tetrahydro-furan-3,4-diol diformate Example 21 was prepared in an analogous manner to Example 4 using 2-cyclohexylethylamine (0.007 g, 0.056 mmol) and 2-(1-methyl-1H-imidazol-4-yl)ethylamine (0.035 g, 0.28 mmol; generated from the corresponding bishydrochloride by neutralisation with slight deficient of solid sodium hydroxide in methanol and evaporation of any volatile matters under a jet of nitrogen) at 90° C. for 5 days.

Example 22

(2R,3R,4S,5S)-2-[6-(2-Cyclohexyl-ethylamino)-2-(1 S-hydroxy-methyl-2-phenyl-ethylamino)-purin-9-yl]-5-(3-ethyl-isoxazol-5-yl)-tetrahydro-furan-3,4-diol formate Example 22 was prepared in an analogous manner to Example 4 using 2-cyclohexylethylamine (0.007 g, 0.056 mmol) and (S)-(–)-2-amino-3-phenyl-1-propanol (0.1 13 g, 0.75 mmol) at 90° C. for 9 d and then 100° C. for 3 days. The title compound was afforded after freeze-drying as a pale brown solid (0.006 g).

LC/MS SYSTEM A $R_t$=4.53 mins, m/z=592 MH$^+$.

Example 23

N-2-{6-(2,2-Diphenyl-ethylamino)-9-[5S-(3-ethyl-isoxazol-5-yl)-3R,4S-dihydroxy-tetrahydro-furan-2R-yl]-9H-purin-2-ylamino}-ethyl)-guanidine diformate (2R,3R,4S,5S)-2-[2-(2-Amino-ethylamino)-6-(2,2-Diphenyl-ethylamino)-purin-9-yl]-5-(3-ethyl-isoxazol-5-yl)-tetrahydro-furan-3,4-diol diformate, as a pale brown solid (0.009 g) after freeze-drying, was prepared in an analogous manner to Example 4 using ethylene-1,2-diamine (0.017 g, 0.28 mmol) at 90° C. for 2 days.

LC/MS SYSTEM A $R_t$=2.61 mins, m/z=571 MH$^+$.

This amine was heated with imidazole (0.002 g, 0.03 mmol) and 1H-pyrazole carboxamidine hydrochloride (5 mg, 0.03 mmol) in a mixture of water (0.25 mL) and ethanol (0.25 mL) at 62° C. for 24 h. Removal of solvent gave a residue which was purified by autoprep. HPLC to afford the title compound after freeze-drying as a pale brown solid (0.001 g). LC/MS SYSTEM A $R_t$=3.84 mins, m/z=613 MH$^+$.

Example 24

N-(4-{6-(2,2-Diphenyl-ethylamino)-9-[5S-(3-ethyl-isoxazol-5-yl)-3R,4S-dihydroxy-tetrahydro-furan-2R-yl]-9H-purin-2-ylamino}-cyclohexyl)-acetamide formate Example 24 was isolated as a by-product with Example 19. The title compound was afforded after freeze-drying as a pale brown solid (0.003 g).

LC/MS SYSTEM B $R_t$=3.02 mins, m/z=667 MH$^+$.

Example 25

2-[2-9-[5S-(3-Ethyl-isoxazol-5-yl)-3R,4S-dihydroxy-tetrahydro-furan-2R-yl]-2-(2-guanidino-ethylamino)-9H-purin-6-ylamino]-ethanesulfonic acid methylamide diformate Example 25 was prepared in an analogous manner to Example 9 using 2-aminoethylsulfonic acid, methylamide (0.041 g, 0.35 mmol). The title compound was afforded after freeze-drying as a hygroscopic brown solid (0.013 g).

LC/MS SYSTEM A $R_t$=3.38 mins, m/z=554 MH$^+$.

Example 26

N-(2-{6-(1,1-Dioxo-hexahydro-1.lambda.6-thiopyran-4-ylamino)-9-[5S-(3-ethyl-isoxazol-5-yl)-3R ,4S-dihydroxy-tetrahydro-furan-2R-yl]-9H-purin-2-ylamino}-ethyl)-guanidine diformate Example 26 was prepared in an analogous manner to Example 9 using 1,1-dioxo-hexahydro-1.lambda.6-thiopyran-4-ylamine (0.052 g, 0.35 mmol) at 50° C. for 4 days and then with ethylenediamine (0.021 ml, 0.32 mmol) at 90° C. for 5 days. The title compound was afforded after freeze-drying as an orange-brown solid (0.002 g). LC/MS SYSTEM B $R_t$=2.31 mins, m/z=565 MH$^+$.

Example 27

2-[9-[5S-(3-Ethyl-isoxazol-5-yl)-3R,4S-dihydroxy-tetrahydro-furan-2R-yl]-2-(1S-hydroxymethyl-2-phenyl-ethylamino)-9H-purin-6-ylamino]-ethanesulfonic acid methylamide formate Example 27 was prepared in an analogous manner to Example 10 using 2-aminoethylsulfonic acid, methylamide (0.048 g, 0.35 mmol) and large excess (S)-(–)-2-amino-phenyl-1-propanol at 90° C. for 12 days. The title compound was afforded after freeze-drying as a yellowish brown solid (0.014 g).

LC/MS SYSTEM A $R_t$=3.88 mins, m/z=603 MH$^+$.

Example 28

1-{4-[9-[5S-(3-Ethyl-isoxazol-5-yl)-3R,4S-dihydroxy-tetrahydro-furan-2R-yl]-2-(1S-hydroxymethyl-2-phenyl-ethylamino)-9H-purin-6-ylamino]-piperidin-1-yl}-ethanone formate Example 28 was prepared in an analogous manner to Example 10 using 1-(4-aminopiperidin-1-yl)-ethanone (0.050 g, 0.35 mmol) and large excess (S)-(–)-2-amino-3-phenyl-1-propanol at 90° C. for 12 days. The title compound was afforded after freeze-drying as a hygroscopic brown solid (0.022 g).

LC/MS SYSTEM B $R_t$=2.57 mins, m/z=607 MH$^+$.

Example 29

1-(4-{2-(trans-4-Amino-cyclohexylamino)-9-[5S-(3-ethyl-isoxazol-5-yl)-3R,4S-dihydroxy-tetrahydro-furan-2R-yl]-9H-purin-6-ylamino}-piperidin-1-yl)-ethanone diformate Example 29 was prepared in an analogous manner to Example 10 using 1-(4-aminopiperidin-1-yl)-ethanone (0.050 g, 0.35 mmol) and trans-cyclohexane-1,4-diamine (0.037 g, 0.32 mmol) at 90° C. for 3 days. The title compound was afforded after freeze-drying as a brown solid (0.013 g). LC/MS SYSTEM B $R_t$=2.09 mins, m/z=570 MH$^+$.

Example 30

(2R,3R,4S,5S)-2-(3Ethyl-isoxazol-5-yl)-5-[2-(2-pyridin-2-yl-ethylamino)-6-(tetrahydro-thiopyran-4-ylamino)-purin-9-yl]-tetrahydro-furan-3,4-diol diformate Example 30 was prepared in an analogous manner to Example 10 using tetrahydro-thiopyran-4-ylamine (0.037 g, 0.35 mmol) and 2-pyridin-2-yl-ethylamine (0.039 g, 0.32 mmol) at 90° C. for 7 days. The title compound was afforded after freeze-drying as a dark brown solid (0.01 g).

LC/MS SYSTEM B $R_t$=2.41 mins, m/z=553 MH$^+$.

Example 31

(2R,3R,4S,5S)-2-[6-(1,1-Dioxo-hexahydro-1.lambda.6-thiopyran-4-ylamino)-2-(2-piperidin-1-yl-ethylamino)-purin-9-yl]-5-(3-ethyl-isoxazol-5-yl)-tetrahydro-furan-3,4-diol diformate Example 31 was prepared in an analogous manner to Example 10 using 1,1-dioxo-hexahydro-1.lambda.6- thiopyran-4-ylamine (0.052 g, 0.35 mmol) at 50° C. for 4 days and 2-piperidin-1-yl-ethylamine (0.041 g, 0.32 mmol) at 90° C. for 5 days. The title compound was afforded after freeze-drying as a light brown solid (0.006 g). LC/MS SYSTEM B $R_t$=2.17 mins, m/z=591 MH$^+$.

Example 32

(2R,3R,4S,5S)-2-[2-trans-4-Amino-cyclohexylamino)-6-(1-dioxo-hexahydro-1.lambda.6-thiopyran-4-ylamino)-purin-9-yl]-5-(3-ethyl-isoxazol-5-yl)-tetrahydro-furan-3,4-diol diformate Example 32 was prepared in an analogous manner to Example 10 using 1,1-dioxo-hexahydro-1.lambda.6-thiopyran-4-ylamine (0.052 g, 0.35 mmol) at 50° C. for 4 days and trans-cyclohexane-1,4-diamine (0.037 g, 0.32 mmol) at 90° C. for 5 days. The title compound was afforded after freeze-drying as a light brown solid (0.008 g). LC/MS SYSTEM B $R_t$=2.12 mins, m/z=577 MH$^+$.

Examples 33A and B

N-(2-{(6-(1-Acetyl-piperidin-4-ylamino)-9-[5S-(3-ethyl-isoxazol-5-yl)-3R,4S-dihydroxy-tetrahydro-furan-2R-yl]-9H-purin-2-ylamino}-ethyl)-guanidine in 1:1 mixture with N-{2-[9-[5S-(3-ethyl-isoxazol-5-yl)-3R,4S-dihydroxy-tetrahydro-furan-2R-yl]-6-(piperidin-4-ylamino)-9H-purin-2-ylamino]-ethyl}-guanidine diformate Example 33 was prepared in an analogous manner to Example 9 using 1-(4-aminopiperidin-1-yl)-ethanone (0.050 g, 0.35 mmol). The title compounds in the ratio of ca. 1:1 were afforded after freeze-drying as a light brown solid (0.003 g).
LC/MS SYSTEM B $R_t$=2.25 and 2.13 mins, m/z=558 and 516 MH$^+$.

Examples 34A and B (2S,3S,4R,5R)-2-(3-Ethyl-isoxazol-5-yl)-5-[2-(1S-hydroxymethyl-2-phenyl-ethylamino)-6-(tetrahydro-thiopyran-4-ylamino)-purin-9-yl]-tetrahydro-furan-3,4-diol in 1:1 mixture with (2S,3S,4R,5R)-2-(3-ethyl-isoxazol-5-yl)-5-[2-(1S-hydroxymethyl-2-phenyl-ethylamino)-6-(1-oxo-hexahydro-1.lambda.4-thiopyran-4-ylamino)-purin-9-yl]-tetrahydro-furan-3,4-diol formate)

Example 34 was prepared in an analogous manner to Example 10 using tetrahydro-thiopyran-4-ylamine (0.052 g, 0.35 mmol) and large excess (S)-(–)-2-amino-3-phenyl-1-propanol at 90° C. for 12 days. The title compounds as a 1:1 mixture were afforded after freeze-drying as an orange-brown solid (0.008 g).
LC/MS SYSTEM B $R_t$=2.90 and 2.50 mins, m/z=582 and 598 MH$^+$.

Example 35

(2S,3S,4R,5R)-2-(3-Ethyl-4-isoxazol-5-yl)-5-[6-(1-ethyl-propylamino)-2-(1S-hydroxymethyl-2-phenyl-ethylamino)-purin-9-yl]-tetrahydro-furan-3,4-diol formate Intermediate 8 (0.046 g, 0.09 mmol) and 3-(S)-(–)-2-amino-3-phenyl propanol (0.130 g, 0.89 mmol) in anhydrous DMSO (0.5 ml) in a sealed vial (e.g. Reacti-vial™) were heated at 90° C. for 177.5 hrs. Further 3-(S)-(–)-2-amino-3-phenyl propanol (0.130 g, 0.89 mmol) and heated at 90° C. for 67 hrs. The reaction mixture was diluted to a volume of 2 ml with a 1:1 mixture of acetonitrile and water containing 0.1% formic acid, and purified with using Autoprep. HPLC to afford the title compound after freeze drying as a cream coloured solid (0.017 g).
LC/MS System B $R_t$=2.91 mins, m/z=552 MH$^+$.

Example 36

(2S,3S,4R,5R)-2-(3-Ethyl-isoxazol-5-yl)-5-[6-(1(-ethyl-propylamino)-2-(pyrrolidin-3R-ylamino)-purin-9-yl]-tetrahydro-furan-3,4-diol diformate Example 36 was prepared in an analogous manner to Example 35 using (3R)-(+)-3-aminopyrrolidine (0.117 g, 0.89 mmol) with heating at 90° C. for 177.5 hrs. to afford the title compound after freeze drying as a beige coloured solid (0.020 g).
LC/MS System B $R_t$=2.35 mins, m/z=487 MH$^+$.

Example 37

(2S,3S,4R,5R)-2-(3-Ethyl-isoxazol-5-yl)-5-[61-ethyl-propylamino)-2-(2-pyridin-2-yl-ethylamino)-purin-9-yl]-tetrahydro-furan-3,4-diol diformate Example 37 was prepared in an analogous manner to Example 36 with 2-(2-aminoethyl)-pyridine (0.110 g, 0.89 mmol) with heating at 90° C. for 177.5 hrs. to afford the title compound after freeze drying as a beige coloured solid (0.020 g).
LC/MS System B $R_t$=2.44 mins, m/z=523 MH$^+$.

Example 38

(2S,3S,4R,5R)-2-(3Ethyl-isoxazol-5-yl)-5-[6(1-ethyl-propylamino)-2-(2-morpholin-4-yl-ethylamino)-purin-9-yl]-tetrahydro-furan-3,4-diol diformate Intermediate 14 (0.020 g, 0.045 mmol) and 2-ethylamino-morpholine (0.060 g, 0.46 mmol) in DMSO (0.5 ml) were heated at 90° C. in a sealed vial (e.g. Reactivial™) for 19 hrs. The reaction mixture was diluted to a volume of 2 ml with a 1:1 mixture of acetonitrile and water containing 0.1% formic acid, and purified with using Autoprep. HPLC to afford the title compound after freeze drying as a beige coloured solid (0.017 g). LC/MS System A $R_t$=3.57 mins, m/z=531 MH$^+$.

Example 39

(2R,3R,4S,5S)-2-[2(trans-4-Amino-cyclohexylamino)-6(1-ethyl-propylamino)-purin-9-yl]-5-(3-ethyl-isoxazol-5-yl)-tetrahydro-furan-3,4-diol diformate Example 39 was prepared in an analogous manner to Example 35 using trans-1,4-diaminocyclohexane (0.101 g, 0.89 mmol) with heating at 90° C. for 177.5 hrs. A further addition of trans-1,4-diaminocyclohexane (0.101 g, 0.89 mmol) with further heating at 90° C. for 67 hrs. to afford the title compound after freeze drying as a brown coloured solid (0.017 g). LC/MS System B $R_t$=2.21 mins, m/z=515 MH$^+$.

Example 40

N-{2-[9-[5S-(3-Ethyl-isoxazol-5-yl)-3R,4S-dihydroxy-tetrahydro-furan-2R-yl]6-(1-ethyl-propylamino)-9H-purin-2-ylamino]-ethyl}-guanidine diformate Example 40 was prepared in an analogous manner to Example 35 using ethylenediamine (0.054 g, 0.89 mmol)

with heating at 90° C. for 86.5 hrs. To the reaction mixture was added imidazole (0.061 g, 0.89 mmol) and 1H-pyrazolecarboxamidine hydrochloride (0.132 g, 0.89 mmol) which was heated at 90° C. for 18 hrs. to afford the title compound after freeze drying as cream coloured solid (0.015 g). LC/MS System A $R_t$=3.45 mins, m/z=503 MH$^+$.

Example 41

(2R,3R,4S,5S)-2-[6-(3,3-Dimethyl-butylamino)-2-(2-piperidin-1-yl-ethylamino)-purin-9-yl]-5-(3-ethyl-isoxazol-5-yl)-tetrahydro-furan-3,4-diol diformate Intermediate 3 (0.025 g), 3,3-dimethylbutylamine (0.005 g), N,N-diisopropylethylamine (0.007 g) in isopropanol (0.7 ml) were allowed to stand at room temperature for 16 h. The solvent was removed, 2-piperidinoethylamine (0.05 ml) and dimethylsulphoxide (0.05 ml) were added and the mixture heated in a sealed vial (eg Reacti-vial™) at 90° C. for 32 hrs. 2-Piperidinoethylamine (0.05 ml) was added and the mixture heated at 110° C. for a further 16 h. Purification by Autoprep HPLC followed by freeze-drying yielded the title compound as a yellow solid (0.005 g). LC/MS System A $R_t$=3.52 min, m/z 543 (MH$^+$).

Example 42

(2R,3R,4S,5S)-2-[6-(3,3-Dimethyl-butylamino)-2-(2-morpholin-4-ethylamino)-purin-9-yl]-5-(3-ethyl-isoxazol-5-yl)-tetrahydro-furan-3,4-diol diformate]

Example 42 was prepared in an analogous manner to Example 41 using 4-(2-aminoethyl)morpholine (0.05 ml) at 90° C. for 32 h. Further 4(2-aminoethyl)morpholine (0.05 ml) was added and the mixture heated at 110° C. for 16 h. The title compound was afforded after freeze-drying as a pale brown solid (0.004 g). LC/MS System B $R_t$=2.48 min, m/z 545 (MH$^+$).

Example 43

(2R,3R,4S,5S)-2-{6-Benzylamino-2-[2-(1-methyl-1H-imidazol-1-yl)-ethylamino]-purin-9-yl}-5-(3-ethyl-isoxazol-5-yl)-tetrahydro-furan-3,4-diol diformate Example 43 was prepared in an analogous manner to Example 41 using benzylamine (0.006 g) at room temperature for 16 h then 2-(1-methyl-1H-imidazol-4-yl)ethylamine (0.033 g) at 90° C. for 32 h. Further 2-(1-methyl-1H-imidazol-4-yl)ethylamine (0.033 g) was added and the mixture heated at 110° C. for 16 h. The title compound was afforded after freeze-drying as a cream coloured solid (0.009 g). LC/MS System A $R_t$=3.43 min, m/z 546 (MH$^+$).

Example 44

(2R,3R,4S,5S)-2-[6-Benzylamino-2-(2-piperidin-1-yl-ethylamino)-purin-9-yl]-5-(3-ethyl-isoxazol-5-yl)-tetrahydro-furan-3,4-diol diformate Example 43 was prepared in an analogous manner to Example 41 using benzylamine (0.006 g) at room temperature for 16 h then 2-piperidinoethylamine (0.05 ml) at 90° C. for 32 h. Further 2-piperidinoethylamine (0.05 ml) was added and the mixture heated at 110° C. for 16 h. The title compound was afforded after freeze-drying as a pale yellow solid (0.005 g). LC/MS System B $R_t$=2.48 min, m/z 549 (MH$^+$).

Example 45

(2S,3S,4R,5R)-2-(3-Ethyl-isoxazol-5-yl)-5-[6-(1S-hydroxymethyl-2-phenyl-ethylamino)-2-(2-piperidin-1-yl-ethylamino)-purin-9-yl]-tetrahydro-furan-3,4-diol diformate Example 43 was prepared in an analogous manner to Example 41 using (S)-(−)-2-amino-3-phenyl-1-propanol (0.008 g) at room temperature for 16 h. then 2-piperidinoethylamine (0.05 ml) at 90° C. for 32 h. Further 2-piperidinoethylamine (0.05 ml) was added and the mixture heated at 110° C. for 16 h. The title compound was afforded after freeze-drying as a pale yellow solid (0.006 g).
LC/MS System B $R_t$=2.40 min m/z 593 (MH$^+$).

Example 46

(2R,3R,4S,5S)-2-[2-(Cyclopentylamino)-6-(1-ethyl-propylamino)-purin-9-yl]-5-(3-ethyl-isoxazol-5-yl)-tetrahydro-furan-3,4-diol formate Intermediate 14 (0.206 g, 0.471 mmol) was dissolved in dry DMSO (2.2 ml). An a aliquot of this solution (0.1 ml, 0.021 mmol) was added to cyclopentylamine (0.011 g, 0.126 mmol) in a 1 ml sealed vial (e.g. Reacti-vial™). Mixture was heated at 90° C. for 114.75 h. The resultant crude product was purified by autoprep. HPLC to afford the title compound after freeze-drying as a white solid (0.001 g). LC/MS SYSTEM B $R_t$=3.07 mins, m/z=486 MH$^+$.

Example 47

(2R,3R,4S,5S)-2-[2-(3,4-Dimethoxyphenyl-ethylamino)-6-(1-ethyl-propylamino)-purin-9-yl]-5-(3-ethyl-isoxazol-5-yl)-tetrahydro-furan-3,4-diol formate Example 47 was prepared in an analogous manner to Example 46 using 3,4-dimethoxyphenyl-ethylamine (0.023 g, 0.126 mmol) at 90° C. for 73.5 h. The title compound was afforded after freeze-drying as a white solid (0.003 g).
LC/MS SYSTEM A $R_t$=4.28 mins, m/z=582 MH$^+$.

Example 48

(2R,3R,4S,5S)-2-[2-(4-tetrahydropyranyl-amino)-6-(1-ethyl-propylamino)-purin-9-yl]-5-(3-ethyl-isoxazol-5-yl)-tetrahydro-furan-3,4-diol formate Example 48 was prepared in an analogous manner to Example 46 using tetrahydro-pyran-4-ylamine (0.013 g, 0.126 mmol) at 90° C. for 204.75 h. More tetrahydro-pyran-4-ylamine (0.013 g, 0.126 mmol) was added. Mixture heated at 110° C. for a further 67 h. The title compound was afforded after freeze-drying as a light brown solid (0.001 g).
LC/MS SYSTEM B $R_t$=2.73 mins, m/z=502 MH$^+$.

Example 49

(2R,3R,4S,5S)-2-[2-(1-Benzyl-pyrrolidin-3S-1-ylamino)-6-(1-ethyl-propylamino)purin-9-yl]-5-(3-ethyl-isoxazol-5-yl)-tetrahydro-furan-3,4-diol formate Example 49 was prepared In an analogous manner to Example 46 using (3S)-(+)-1-benzyl-3-aminopyrrolidine (0.022 g, 0.126 mmol) at 90° C. for 204.75 h. The title compound was afforded after freeze-drying as a light brown solid (0.006 g).
LC/MS SYSTEM B $R_t$=2.59 mins, m/z=577 MH$^+$.

Example 50

5-(5R-{6-Ethyl-propylamino)-2-[2(1-methyl-1H-imidazol-4-yl)-ethylamino]-purin-9-yl}-3S,4R-dihydroxy-tetrahydro-furan-2S-yl)-isoxazole-3-carbaldehyde oxime diformate A mixture of N-hydroxy-2-hydroxyimino-acetimidoyl chloride (0.016 g, 0.13 mmol) and Intermediate 28 (0.02 g, 0.044 mmol) in ethyl acetate (2 mL) and water (0.1 mL) was stirred vigorously with solid sodium bicarbonate (0.081 g, 0.96 mmol) at room temperature. More reagents [N-hydroxy-2-hydroxyimino-acetimidoyl chloride (0.032 g, 0.26 mmol), solid sodium bicarbonate (0.162 g, 1.92 mmol) and water (0.1 mL)] were added at 169.5 h and a further 4 days. After another 20 h, the reaction was diluted with water (5 mL), extracted with ethyl acetate (2×3 mL). Combined organic solution was evaporated a brown gum. The resultant crude product was purified by autoprep. HPLC to afford the title compound after freeze-drying as a creamy white solid (0.001 g).

LC/MS SYSTEM C $R_t$=2.25 mins, m/z=541 MH$^+$.

Example 51

(2S,3S,4R,5R)-2-(3-Ethyl-isoxazol-5-yl)-5-[6-(1S-hydroxymethyl-2-phenyl-ethylamino)-2-(2-morpholin-4-yl-ethylamino)-purin-9-yl]-tetrahydro-furan-3,4-diol diformate Intermediate 3 (0.025 g), (S)-(−)-2-amino-3-phenyl-1-propanol (0.008 g), N,N-diisopropylethylamine (0.007 g) in isopropanol (0.7 ml) were allowed to stand at room temperature for 16 h. The solvent was removed in vacuo, 4-(2-aminoethyl)morpholine (0.05 ml) and DMSO (0.05 ml) were added and the mixture heated in a sealed vial (eg Reacti-vial™) at 90° C. for 32 h. 4-(2-aminoethyl) morpholine (0.05 ml) was added and the mixture heated at 110° C. for a further 16 h. Purification by Autoprep HPLC twice followed by freeze-drying yielded the title compound as a white solid (0.004 g). LC/MS System B Rt=2.40 min, m/z 595 (MH$^+$).

Example 52

(2S,3S,4R,5R)-2-(3-Ethyl-isoxazol-5-yl)-5-[6-benzylamino-2-(2-pyridin-2-yl-ethylamino)-purin-yl]-tetrahydro-furan-3,4-diol diformate Intermediate 3 (0.025 g), benzylamine (0.006 g), N,N-diisopropylethylamine (0.007 g) in isopropanol (0.7 ml) were allowed to stand at room temperature for 16 h. The solvent was removed in vacuo, 2-(2-aminoethyl)-pyridine (0.05 ml) and dimethylsulphoxide (0.05 ml) were added and the mixture heated in a sealed vial (eg Reacti-vial™) at 900° C. for 32 h . 4(2-aminoethyl)morpholine (0.05 ml) was added and the mixture heated at 110° C. for a further 16 h. Purification by Autoprep HPLC twice followed by freeze-drying yielded the title compound as a cream coloured solid (0.002 g). LC/MS System B Rt=2.56 min, m/z=543 (MH$^+$).

Example 53

(2S,3S,4R,5R)-2-(3-Ethyl-isoxazol-5-yl)-5-{6-(1-ethyl-propylamino)-2-[2-(pyridin-2-ylamino)-ethylamino]-purin-9-yl}-tetrahydro-furan-3,4-diol diformate Example 53 was prepared in an analogous manner to Example 46 2-(pyridin-2-ylamino)ethylamine (0.017 g, 0.126 mmol) at 90° C. for 73.5 h. The title compound was afforded after freeze-drying as a white solid (0.005 g).

LC/MS SYSTEM A Rt=3.41 mins, m/z=538 MH$^+$.

Example 54

(2R,3R,4S,5S)-2-[6-(1-Ethyl-propylamino)-2-(2-piperidin-1-yl-ethylamino)-purin-9-yl]-5-[3-(1-hydroxy-ethyl)-isoxazol-5-yl]-tetrahydro-furan-3,4-diol diformate Example 54 was prepared in an analogous manner to Example 67 using Intermediate 23 (0.022 g, 0.04 mmol). The title compound was afforded after freeze-drying as a light brown solid (0.004 g). LC/MS SYSTEM A Rt=3.25 mins, m/z=545 MH$^+$.

Example 55

(2R,3R,4S,5S)-2-[6-(1-Ethyl-propylamino)-2-(2-piperidin-1-yl-ethylamino)-purin-9-yl]-5-(3-methyl-isoxazol-5-yl)-tetrahydro-furan-3,4-diol diformate Example 55 was prepared in an analogous manner to Example 67 using Intermediate 20 (0.022 g, 0.045 mmol) at 90–95° C. for 57 h. The title compound was afforded after freeze-drying as a creamy white solid (0.008 g). LC/MS SYSTEM A Rt=3.38 mins, m/z=515 MH$^+$.

Example 56

(2R,3R,4S,5S)-2-[6-(1-Ethyl-propylamino)-2-(2-piperidin-yl-ethylamino)-purin-9-yl]-5-(3-propyl-isoxazol-5-yl)-tetrahydro-furan-3,4-diol diformate Example 56 was prepared in an analogous manner to Example 67 using Intermediate 21 (0.027 g, 0.045 mmol) at 90–95° C. for 57 h. The title compound was afforded after freeze-drying as a creamy white solid (0.01 g).

LC/MS SYSTEM A Rt=3.60 mins, m/z=543 MH$^+$.

Example 57

(2R,3R,4S,5S)-2-[6-(1-Ethyl-propylamino)-2-(2-piperidin-1-yl-ethylamino)-purin-9-yl]-5-(3-hydroxymethyl-isoxazol-5-yl)-tetrahydro-furan-3,4-diol diformate Example 57 was prepared in an analogous manner to Example 67 using Intermediate 24 (0.028 g, 0.051 mmol) at 95° C. for 16.5 h. The title compound was afforded after freeze-drying as a brown solid (0.002 g).

LC/MS SYSTEM A Rt=3.21 mins, m/z=531 MH$^+$.

Example 58

(2R,3R,4S,5S)-2-{6-(1-Ethyl-propylamino)-2-[2-(1-methyl-1H-imidazol-4-yl)-ethylamino]-purin-9-yl}-5-[3-(1-hydroxy-ethyl)-isoxazol-5-yl]-tetrahydro-furan-3,4-diol diformate A mixture of Intermediate 23 (0.022 g, 0.04 mmol) and 2-(1-methyl-1H-imidazol-4-yl)ethylamine (0.038 g, 0.3 mmol; generated from the corresponding bishydrochloride by neutralisation with slight deficient of solid sodium hydroxide in methanol and evaporation of any volatile matters under a jet of nitrogen) was dissolved in dry DMSO (0.1 ml) in a sealed vial (e.g. Reacti-vial™). Mixture was heated at 110° C. for 28.5 h. The resultant crude product was purified by autoprep. HPLC to afford the title compound after freeze-drying as a light brown solid (0.001 g). LC/MS SYSTEM A Rt=3.17 mins, m/z=542 MH$^+$.

Example 59

(2R,3R,4S,5S)-2-{6-(1-Ethyl-propylamino)-2-[2-(1-methyl-1H-imidazol-4-yl)-ethylamino]-purin-9yl}-5-(3-methyl-isoxazol-5-yl)-tetrahydro-furan-3,4-diol diformate Example 59 was prepared in an analogous manner to Example 58 using Intermediate 20 (0.022 g, 0.045 mmol) at 110° C. for 28.5 h. The title compound was afforded after freeze-drying as a brown solid (0.019 g). LC/MS SYSTEM A Rt=3.23 mins, m/z=512 MH+.

Example 60

(2R,3R,4S,5S)-2-{6-(1-Ethyl-propylamino)-2-[2-(1-methyl-1H-imidazol-4-yl)-ethylamino]-purin-9-yl}-5-(3-propyl-isoxazol-5-yl)-tetrahydro-furan-3,4-diol diformate Example 60 was prepared in an analogous manner to Example 58 using Intermediate 21 (0.027 g, 0.045 mmol) at 110° C. for 28.5 h. The title compound was afforded after freeze-drying as a creamy white solid (0.011 g).

LC/MS SYSTEM A Rt=3.42 mins, m/z=540 MH+.

Example 61

(2R,3R,4S,5S)-2-{6-(1-Ethyl-propylamino)-2-[2-(1-methyl-1H-imidazol-4-yl)-ethylamino]-purin-9-yl}-5-(3-hydroxymethyl-isoxazol-5-yl)-tetrahydro-furan-3,4-diol diformate Example 61 was prepared in an analogous manner to Example 58 using Intermediate 24 (0.028 g, 0.051 mmol) at 110° C. for 16.5 h. A mixture of Intermediate 24 (0.028 g, 0.051 mmol) and 2-(1-methyl-1 H-imidazol-4-yl)ethylamine (0.038 g, 0.3 mmol; generated from the corresponding bishydrochloride by neutralisation with slight deficient of solid sodium hydroxide in methanol and evaporation of any volatile matters under a jet of nitrogen) was dissolved in dry DMSO (0.1 ml) in a sealed vial (e.g. Reacti-vial™). The mixture was heated at 110° C. for 16.5 h. The resultant crude product was purified by autoprep. HPLC to afford the title compound after freeze-drying as a brown solid (0.007 g). LC/MS SYSTEM A Rt=3.12 mins, m/z=528 MH+.

Example 62

(2S,3S,4R,5R)-2-(3-Ethyl-isoxazol-5-yl)-5-{6-(1S-hydroxymethyl-2-phenyl-ethylamino)-2-[2-(pyridin-2-ylamino)-ethylamino]-purin-9-yl}-tetrahydro-furan-3,4-diol diformate Intermediate 26 (0.110 g, 0.22 mmol) was dissolved in dry DMSO (2.5 ml). An aliquot of this solution (0.5 ml, 0.044 mmol) was added to Intermediate 27 (0.060 g, 0.44 mmol) in a sealed vial (e.g. Reacti-vial™). Mixture was heated at 90° C. for 80 h. Purification using Autoprep HPLC yielded the title compound after freeze-drying as an off-white solid (0.016 g). LC/MS SYSTEM A Rt=3.52 mins, m/z=602 MH+.

Example 63

(2S,3S,4R,5R)-2-(3-Ethyl-isoxazol-5-yl)-5-[6-(1S-hydroxymethyl-2-phenyl-ethylamino)-2-(2-pyrrolidin-1-yl-ethylamino)-purin-9-yl]-tetrahydro-furan-3,4-diol diformate Example 63 was prepared in an analogous manner to Example 62 using 1-(2-aminoethyl)-pyrrolidine (0.050 g, 0.44 mmol) at 90° C. for 80 h. The title compound was afforded after freeze-drying as a white solid (0.024 g). LC/MS SYSTEM A Rt=3.43 mins, m/z=579 MH+.

Example 64

(2R,3R,4S,5S)-2-[2-(2-Amino-ethylamino)-6-(1S-hydroxymethyl-2-phenyl-ethylamino)-purin-9-yl]-5-(3-ethyl-isoxazol-5-yl)-tetrahydro-furan-3,4-diol diformate Example 64 was prepared in an analogous manner to Example 62 using ethylenediamine (0.026 g, 0.44 mmol) at 90° C. for 20 h. The title compound was afforded after freeze-drying as an off-white solid (0.018 g). LC/MS SYSTEM A Rt=3.36 mins, m/z=525 MH+.

Example 65

(2S,3S,4R,5R)-2-(3-Ethyl-isoxazol-5yl)-5-[6-(3-iodo-benzylamino)-2-(2-piperidin-1-yl-ethylamino)-purin-9-yl]-tetrahydro-furan-3,4-diol diformate Intermediate 25 (0.015 g, 0.026 mmol) dissolved in dry DMSO (1.0 ml) was added to 2-piperidinoethylamine (0.016 g, 0.13 mmol) in a sealed vial (e.g. Reacti-vial™). Mixture was heated at 90° C. for 76 h. Purification using Autoprep HPLC yielded the title compound after freeze-drying as an off-white solid (0.003 g). LC/MS SYSTEM A Rt=4.56 mins, m/z=592 MH+.

Example 66

(2R,3R,4S,5S)-2-[2-Ethylamino-6-(3-iodo-benzylamino)-purin-9-yl]-5-(3-ethyl-isoxazol-5-yl)-tetrahydro-furan-3,4-diol formate Example 66 was prepared in an analogous manner to Example 65 using ethylamine (0.017 g, 0.44 mmol, 70% wt solution in water) 90° C. for 76 h. The title compound was afforded after freeze-drying as an off-white solid (0.004 g).

LC/MS SYSTEM A Rt=3.64 mins, m/z=675 MH+.

Example 67

(2S,3S,4R,5R)-2-(3-Bromo-isoxazol-5-yl)-5-[6-(1-ethyl-propylamino)-2-(2-piperidin-1-yl-ethylamino)-purin-9-yl]-tetrahydro-furan-3,4-diol diformate A mixture of Intermediate 18 (0.021 g, 0.037 mmol) and piperidin-1-yl-2-ethylamine (0.038 g, 0.3 mmol) was dissolved in dry DMSO (0.1 ml) in a sealed vial (e.g. Reacti-vial™). Mixture was heated at 90° C. for 28.5 h. The resultant crude product was purified by autoprep. HPLC to afford the title compound after freeze-drying as a creamy white solid (0.003 g). LC/MS SYSTEM A Rt=3.48 mins, m/z=579 MH+ for $C_{24}H_{35}{}^{79}BrN_8O_4$.

Example 68

5-(5R-{6-(1-Ethyl-propylamino)-2-[2-(1-methyl-1H-imidazol-4-yl)-ethylamino]-purin-9-yl}-3S,4R-dihydroxy-tetrahydro-furan-2S-yl)-isoxazole-3-carboxylic acid ethyl ester diformate Example 68 was prepared in an analogous manner to Example 50 using chloro-hydroxyimino-acetic acid ethyl ester (0.02 g, 0.13 mmol) and solid sodium bicarbonate (0.081 g, 0.96 mmol). More reagents were added at 169.5 h [chloro-hydroxyimino-acetic acid ethyl ester (0.128 g, 0.845 mmol), solid sodium bicarbonate (0.322 g, 3.83 mmol and water (0.1 mL)] and a further 4 days [chloro-hydroxyimino-acetic acid ethyl ester (0.04 g, 0.26 mmol) and solid sodium bicarbonate (0.162 g, 1.92 mmol)]. The title compound was afforded after freeze-drying as a light brown solid (0.002 g). LC/MS SYSTEM C $R_t$=2.39 mins, m/z=570 MH+.

Example 69

(2S,3S,4R,5R)-2-(3-Ethyl-isoxazol-5-yl)-5-[6-(1S-hydroxymethyl-2-methyl-propylamino)-2-(2-pyrrolidin-1-yl-ethylamino)-purin-9-yl]-tetrahydro-furan-3,4-diol diformate Intermediate 29 (0.113 g, 0.25 mmol) was dissolved in dry DMSO (7 ml). An aliquot of this solution (1 ml, 0.036 mmol) was added to 1-(2-aminoethyl)-pyrrolidine (0.041 g, 0.36 mmol) in a sealed vial (e.g. Reacti-vial™). Mixture was heated at 90° C. for 90 h. Purification using Autoprep HPLC yielded the title compound after freeze-drying as a brown gum (0.005 g). LC/MS SYSTEM C $R_t$=2.20 mins, m/z=531 MH$^+$.

Example 70

(2S,3S,4R,5R)-2-(3-Ethyl-isoxazol-5-yl)-5-[6-(1(1S-hydroxymethyl-2-methyl-propylamino)-2-(2-piperidin-1-yl-ethylamino)-purin-9-yl]-tetrahydro-furan-3,4-diol diformate Example 70 was prepared in an analogous manner to Example 69 using 2-piperidinoethylamine (0.044 g, 0.36 mmol) at 90° C. for 90 h. The title compound was afforded after freeze-drying as a brown gum (0.009 g). LC/MS SYSTEM C $R_t$=3.39 mins, m/z=545 MH$^+$.

Example 71

(2S,3S,4R,5R)-2-(3-Ethyl-isoxazol-5-yl)-5-{6-(1S-hydroxymethyl-2-methyl-propylamino)-2-[2-(pyridin-2-ylamino)-ethylamino]-purin-9-yl}-tetrahydro-furan-3,4-diol diformate Example 71 was prepared in an analogous manner to Example 69 using Intermediate 27 (0.049 g, 0.36 mmol) at 90° C. for 159 h. The title compound was afforded after freeze-drying as a pale brown foam (0.01 1 g). LC/MS SYSTEM C $R_t$=3.39 mins, m/z=554 MH$^+$.

Example 72

(2S,3S,4R,5R)-2-(3-Ethyl-isoxazol-5-yl)-5-{6-(1S-hydroxymethyl-2-methyl-propylamino)-2-(1S-hydroxymethyl-2-phenyl-ethylamino)-purin-9-yl}-tetrahydro-furan-3,4-diol diformate Example 72 was prepared in an analogous manner to Example 69 using 3-(S)-(−)-2amino-3-phenyl propanol (0.054 g, 0.36 mmol) at 90° C. for 159 h. The title was afforded after freeze-drying as a yellow foam (0.006 g). LC/MS SYSTEM C $R_t$=2.79 mins, m/z=568 MH$^+$.

Biological Data

The compounds of the Examples were tested in screen (1) (agonist activity against receptor subtypes) and the results obtained were as follows:

| Example No. | A2a | A3 | A1 |
|---|---|---|---|
| 1 | 0.52 | >436 | 288.5 |
| 2 | 0.43 | >545 | 88.9 |
| 3 | 1.32 | >375 | 231 |
| 4 | 0.92 | >267 | 109.3 |
| 5 | 0.11 | >237 | 30.1 |
| 6 | 0.49 | >393 | 66.4 |
| 7 | 0.35 | >312 | >=309.4 |
| 8 | 0.67 | >310 | 49.1 |
| 9 | 2.05 | >323 | 132.3 |
| 10 | 2.07 | >180 | 59.38 |
| 11 | 3.66 | >303 | 32.9 |
| 12 | 3.39 | >410 | 260.3 |
| 13 | 3.03 | >146 | 61.9 |
| 14 | 4.99 | >254 | 77.1 |
| 15 | 3.66 | >146 | 26.05 |
| 16 | 0.35 | >1004 | 442 |
| 17 | 0.34 | >298 | 1172 |
| 18 | 0.72 | >460 | 2580 |
| 19 | 2.41 | >295 | 670.2 |
| 20 | 2.04 | >267 | 310.9 |
| 21 | 1.55 | >267 | 1624.29 |
| 22 | 9.17 | >254 | 8026.2 |
| 23 | 13.4 | >282 | >=3263 |
| 24 | 0.23 | >248 | 573.6 |
| 25 | 5.46 | >198 | 103.8 |
| 26 | 6.89 | >286 | 273.3 |
| 27 | 3 | >273 | 3.18 |
| 28 | 14.5 | >263 | 165.8 |
| 29 | 5.03 | >298 | 27.24 |
| 30 | 4.58 | >257 | 108.8 |
| 31 | 10.59 | >310 | 577.2 |
| 32 | 3.79 | >176 | 31.75 |
| 33 | 13.44 | >365 | 1281.4 |
| 34 | 2.92 | >198 | 19.86 |
| 35 | 2.53 | >223 | 89.16 |
| 36 | 4.7 | >207 | 68.32 |
| 37 | 2.65 | >207 | 136.56 |
| 38 | 5.29 | >737 | 44.1 |
| 39 | 2.12 | >85 | 86.8 |
| 40 | 3.38 | >88 | 70.53 |
| 41 | 27.39 | >395 | 2907.96 |
| 42 | 41.06 | >395 | 1369.08 |
| 43 | 3.53 | >335 | 672.4 |
| 44 | 10.3 | >221 | 725.4 |
| 45 | 1.93 | >189 | 54.04 |
| 46 | 20.06 | >518 | 148.72 |
| 47 | 10.42 | >363 | 148.34 |
| 48 | 11.48 | >363 | 177.71 |
| 49 | 7.79 | >350 | 28.28 |
| 50 | 7.26 | >113 | >6188 |
| 51 | 4.86 | >340 | 22.53 |
| 52 | 21.63 | >340 | 1359.98 |
| 53 | 2.11 | >229 | 128.9 |
| 54 | 0.066 | >350 | 10.18 |
| 55 | 0.175 | >353 | 155.3 |
| 56 | 5.19 | >525 | 101.31 |
| 57 | 0.79 | >525 | 80.76 |
| 58 | 0.244 | >525 | 812.2 |
| 59 | 0.13 | >385 | 194.3 |
| 60 | 4.53 | ≧248.4 | 155.86 |
| 61 | 0.09 | >314 | 38.58 |
| 62 | 1.03 | >303 | 21.37 |
| 63 | 10.57 | >262 | 148.43 |
| 64 | 16.03 | >262 | 44.21 |
| 65 | 4.74 | >262 | 128.27 |
| 66 | 8.32 | >262 | 189.98 |
| 67 | 2.59 | >238 | 219.1 |
| 68 | 30.23 | >113 | 60.30 |
| 69 | 23.73 | >180 | 298.75 |
| 70 | 27.39 | >184 | 149.86 |
| 71 | 12.75 | >184 | 79.51 |
| 72 | 5.39 | >158 | 23.79 |

Values given in the Table are $EC_{50}$ values as a ratio of that of NECA.

Abbreviations

TMSOTf Trimethylsilyltrifluoromethylsulfonate
THP tetrahydropyran
TMS trimethylsilyl
TFA trifluoroacetic acid DMF N,N-dimethylformamide
HMDS 1,1,1,3,3,3-Hexamethyidisilazane
NECA N-ethylcarboxamideadenosine
DMAP 4-dimethylaminopyridine
TEMPO 2,2,6,6-tetramethyl-1-piperidinyloxy, free radical
TMSOTf Trimethylsilyltrifluoromethylsulphonate
DBU 1,8-diazabicyclo[5.4.0]undec-7-ene
BSA bistrimethylsilylacetamide
DCM dichloromethane
DAST diethylaminosulphur trifluoride
Ph phenyl
CdI carbonyldiimidazole
NSAID non-steroidal antiinflammatory drug
THF tetrahydrofuran
Ac acetyl ($CH_3CO$)
Me methyl
Et ethyl
DMSO dimethylsulphoxide

What is claimed is:

1. A compound of formula (I):

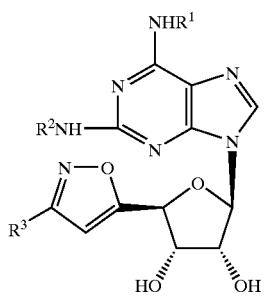

(I)

wherein $R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkylC$_{1-6}$alkyl-;
(v) $C_{1-8}$alkyl-;
(vi) arylC$_{1-6}$alkyl-;
(vii) $R^4R^5$N—C$_{1-6}$alkyl-;
(viii) $C_{1-6}$alkyl-CH(CH$_2$OH)—;
(ix) arylC$_{1-5}$alkyl-CH(CH$_2$OH)—;
(x) arylC$_{1-5}$alkyl-C(CH$_2$OH)$_2$—;
(xi) $C_{3-8}$cycloalkyl independently substituted by one or more —(CH$_2$)$_p$R$^6$ groups;
(xii) H$_2$NC(=NH)NHC$_{1-6}$alkyl-;
(xiii) a group of formula

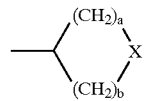

or such a group in which one methylene carbon atom adjacent to X, or both if such exist, is substituted by methyl;
(xiv) —C$_{1-6}$alkyl-OH;
(xv) —C$_{1-8}$haloalkyl;
(xvi) a group of formula

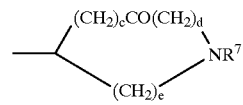

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;
$R^3$ represents methyl, ethyl, —CH=CH$_2$, n-propyl, —CH$_2$CH=CH$_2$, —CH=CHCH$_3$, isopropyl, isopropenyl, cyclopropyl, cyclopropenyl, cyclopropylmethyl, cyclopropenylmethyl, —CH(OH)CH$_3$, —(CH$_2$)$_q$halogen, —(CH$_2$)$_h$Y(CH$_2$)$_i$H, —(CH$_2$)$_k$Z, —(CH$_2$)$_h$CO(CH$_2$)$_o$H, —(CH$_2$)$_r$S(O)$_t$(CH$_2$)$_s$H or —(CH$_2$)$_k$C((CH$_2$)$_u$H)=NO(CH$_2$)$_l$H;
Y represents O, S or N(CH$_2$)$_j$H;
Z represents —COO(CH$_2$)$_i$H or —CON(CH$_2$)$_m$H((CH$_2$)$_n$H);
a and b independently represent an integer 0 to 4 provided that a+b is in the range 3 to 5;
c, d and e independently represent an integer 0 to 3 provided that c+d+e is in the range 2 to 3;
f represents 2 or 3 and g represents an integer 0 to 2;
p represents 0 or 1;
q represents an integer 0 to 3;
h represents an integer 0 to 2;
i represents an integer 0 to 2 such that h+i is in the range 0 to 3;
j represents an integer 0 to 2 such that h+i+j is in the range 0 to 3;
k represents 0 or 1;
l represents 1 or 2, such that k+l is in the range 1 to 2;
m and n independently represent an integer 0 to 2 such that k+m+n is in the range 0 to 2;
o represents an integer 0 to 2 such that h+o is in the range 0 to 2;
r and s independently represent 1 or 2 such that r+s is in the range 2 to 3;
t represents 1 or 2;
u and v independently represent 0 or 1 such that k+u+v is in the range 0 to 1;
$R^4$ and $R^5$ independently represent hydrogen, C$_{1-6}$alkyl, aryl, arylC$_{1-6}$alkyl- or NR$^4$R$^5$ together may represent pyridinyl, pyrrolidinyl, piperidinyl, morpholinyl, azetidinyl, azepinyl, piperazinyl, N—C$_{1-6}$alkylpiperazinyl or 2-(1-methyl-1H-imidazol-4-yl)-;
$R^6$ represents —OH, —NH$_2$, —NHCOCH$_3$ or halogen;
$R^7$ represents hydrogen, —C$_{1-6}$alkyl, —C$_{1-6}$alkylaryl or —COC$_{1-6}$alkyl;
X represents NR$^7$, O, S, SO or SO$_2$;
and salts and solvates thereof.

2. A compound of formula (I) according to claim 1 wherein $R^3$ represents methyl, ethyl or n-propyl and $R^7$ represents hydrogen, —C$_{1-6}$alkyl, —C$_{1-6}$alkylaryl or —COCH$_3$.

3. A compound of formula (I) according to claim 1 wherein $R^1$ and $R^2$ do not both represent hydrogen.

4. A compound of formula (I) according to claim 1 wherein $R^1$ represents C$_{3-8}$cycloalkyl, aryl$_2$CHCH$_2$—, arylC$_{1-6}$alkyl-, C$_{1-8}$alkyl-, aryl, —(CH$_2$)$_f$SO$_2$NH$_g$(C$_{1-4}$alkyl)$_{2-g}$, tetrahydropyran-n-yl or tetrahydrothiopyran-n-yl where n is 3 or 4, $C_{3-8}$cycloalkyl$C_{1-6}$alkyl-, hydrogen, or $R^4R^5N$—$C_{1-6}$alkyl- where $NR^4R^5$ together represents piperidinyl or morpholinyl.

5. A compound of formula (I) according to claim 1 wherein $R^1$ represents $C_{1-6}$alkyl-CH(CH$_2$OH)—, 1,1-dioxo-hexahydro-1-λ-6-thiopyran-4-yl, N-acetyl-piperidin-4-yl, 1S-hydroxymethyl-2-phenylethyl, piperidin-4-yl, or 1-oxo-hexahydro-1-λ-4-thiopyran-4-yl.

6. A compound of formula (I) according to claim 1 wherein $R^1$ represents —CH$_2$CHPh$_2$, —CH(Et)$_2$ or phenylethyl.

7. A compound of formula (I) according to claim 1 wherein $R^2$ represents —$C_{1-6}$alkyl-OH, $H_2NC(=NH)NHC_{1-6}$alkyl-, $R^4R^5NC_{1-6}$alkyl- where $NR^4R^5$ together represents pyridinyl, piperidinyl, morpholinyl or 2-(1-methyl-1H-imidazol-4-yl), aryl$C_{1-5}$alkylCH(CH$_2$OH)—, aryl, $C_{3-8}$cycloalkyl$C_{1-6}$alkyl-, tetrahydro-1,1-dioxide thiophen-3-yl, $C_{3-8}$cycloallkyl, $C_{1-6}$alkyl-CH(CH$_2$OH)—, aryl$C_{1-6}$alkyl-, pyrrolidin-3-yl, 2-oxopyrrolidin-4-yl, 2-oxopyrrolidin-5yl, piperidin-3-yl, aryl $C_{1-6}$alkyl, $C_{3-8}$cycloalkyl independently substituted by one or more —(CH$_2$)$_p$R$^6$ groups, or piperidin-4-yl in which the ring nitrogen is optionally substituted by $C_{1-6}$alkyl.

8. A compound of formula (I) according to claim 1 wherein $R^2$ represents $C_{1-8}$alkyl or $R^4R^5NC_{1-6}$alkyl- wherein $R^4$ and $R^5$ independently represent hydrogen or aryl or $R^4R^5N$ together represents pyrrolidinyl.

9. A compound of formula (I) according to claim 1 wherein $R^2$ represents piperidin-1-ylethyl or 2-(1-methyl-1H-imidazol-4-yl)ethyl.

10. A compound of formula (I) according to claim 1 wherein $R^3$ represents —CH=NOH, cyclopropyl, —COOCH$_3$, —COOCH$_2$CH$_3$, —CH$_2$OH, —CH(OH)CH$_3$ or halogen.

11. A compound of formula (I) according to claim 1 wherein $R^3$ represents methyl, ethyl or n-propyl.

12. A compound of formula (I) according to claim 1 wherein $R^3$ represents ethyl or —CH$_2$OH.

13. A compound of formula (I) according to claim 12 wherein $R^3$ represents ethyl.

14. A compound of formula (I) according to claim 1 wherein $R^4$ and $R^5$ independently represent hydrogen, $C_{1-6}$alkyl, aryl, aryl$C_{1-6}$alkyl- or $NR^4R^5$ together may represent pyrrolidinyl, piperidinyl, morpholinyl, azetidinyl, azepinyl, piperazinyl or N—$C_{1-6}$alkylpiperazinyl.

15. A compound of formula (I) according to claim 14 wherein $R^4$ and $R^5$ independently represent hydrogen, $C_{1-6}$alkyl or aryl or $NR^4R^5$ together represent pyrrolidinyl, piperidinyl, morpholinyl, azetidinyl, azepinyl or N-methylpiperazinyl.

16. A compound of formula (I) according to claim 1 which is (2R,3R,4S,5S)-2-[6-(2,2-Diphenyl-ethylamino)-2-(2-piperidin-1-yl-ethylamino)-purin-9-yl]-5-(3-ethyl-isoxazol-5-yl)-tetrahydro-furan-3,4-diol or a salt or solvate thereof.

17. A compound of formula (1) according to claim 1 which is (2R,3R,4S,5S)-2-(3-Ethyl-isoxazol-5-yl)-5-[6-phenethylamino-2-(2-piperidin-1-yl-ethylamino)-purin-9-yl]-tetrahydro-furan-3,4-diol or a salt or solvate thereof.

18. A compound of formula (1) according to claim 1 which is (2S,3S,4R,5R)-2-(3-Ethyl-isoxazol-5-yl)-5-[6-(1-ethyl-propylamino)-2-(2-piperidin-1-yl-ethylamino)-purin-9-yl]-tetrahydro-furan-3,4-diol or a salt or solvate thereof.

19. A compound of formula (1) according to claim 1 which is (2R,3R,4S,5S)-2-{6-(1-Ethyl-propylamino)-2-[2-(1-methyl-1H-imidazol-4-yl)-ethylamino]-purin-9-yl}-5-(3-hydroxymethyl-isoxazol-5-yl)-tetrahydro-furan-3,4-diol or a salt or solvate thereof.

20. A compound of formula (I) according to claim 1 which is (2R,3R,4S,5S)-2-[6-(2,2-Diphenyl-ethylamino)-2-(2-morpholin-4-yl-ethylamino)-purin-9-yl]-5-(3-ethyl-isoxazol-5-yl)-tetrahydro-furan-3,4-diol; (2R,3R,4S,5S)-2-[6-(2,2-Diphenyl-ethylamino)-2-(2-hydroxy-ethylamino)-purin-9-yl]-5-(3-ethyl-isoxazol-5-yl)-tetrahydro-furan-3,4-diol; (2S,3S,4R,5R)-2-(3-Ethyl-isoxazol-5-yl)-5{-6-(1-ethyl-propylamino)-2-[2-(1-methyl-1H-imidazol-4-yl)-ethylamino]-purin-9-yl}-tetrahydro-furan-3,4-diol; (2R,3R,4S,5S)-2-{6-(3,3-Dimethyl-butylamino)-2-[2-(1-methyl-1H-imidazol-4-yl)-ethylamino]-purin-9-yl}-5-(3-ethyl-isoxazol-5-yl)-tetrahydro-furan-3,4-diol; (2S,3S,4R,5R)-2-(3-Ethyl-isoxazol-5-yl)-5-[6-(cyclopentylamino)-2-(2-piperidin-1-yl-ethylamino)-purin-9-yl]-tetrahydro-furan-3,4-diol; N-{2-[9-[5S-(3-Ethyl-isoxazol-5-yl)-3R,4S-dihydroxy-tetrahydro-furan-2R-yl]-6-(tetrahydro-thiopyran-4-ylamino)-9H-purin-2-ylamino]-ethyl}-guanidine; (2S,3S,4R,5R)-2-(3-Ethyl-isoxazol-5-yl)-5-[6(3-fluoro-4-hydroxy-phenylamino)-2-(2-piperidin-1-yl-ethylamino)-purin-9-yl]-tetrahydro-furan-3,4-diol; 2-[9-[5S-(3-Ethyl-isoxazol-5-yl)-3R,4S-dihydroxy-tetrahydro-furan-2R-yl]-2-(2-piperidin-1-yl-ethylamino)-9H-purin-6-ylamino]-ethanesulfonic acid methylamide; (2S,3S,4R,5R)-2-(3-Ethyl-isoxazol-5-yl)-5-[2-(2-piperidin-1-yl-ethylamino)-6-(tetrahydro-thiopyran-4-ylamino)-purin-9-yl]-tetrahydro-furan-3,4-diol; (2S,3S,4R,5R)-2-(3-Ethyl-isoxazol-5-yl)-5-[2-(2-pyridin-2-yl-ethylamino)-6-(tetrahydro-pyran-4-ylamino)-purin-9-yl]-tetrahydro-furan-3,4-diol; (2S,3S,4R,5R)-2-(3-Ethyl-isoxazol-5-yl)-5-[2-(2-piperidin-1-yl-ethylamino)-6-(tetrahydro-pyran-4-ylamino)-purin-9-yl]-tetrahydro-furan-3,4-diol; (2S,3S,4R,5R)-2-(3-Ethyl-isoxazol-5-yl)-5-[2(1S-hydroxymethyl-2-phenyl-ethylamino)-6-(tetrahydro-pyran-4-ylamino)-purin-9-yl]-tetrahydro-furan-3,4-diol; (2R,3R,4S,5S)-2-{6-(2,2-Diphenyl-ethylamino)-2-[2-(pyridin-2-ylamino)-ethylamino]-purin-9-yl}-3-(5-(3-ethyl-isoxazol-5-yl)-tetrahydro-furan-3,4-diol; (2R,3R,4S,5 S)-2-[6-(2,2-Diphenyl-ethylamino)-2-(1S-hydroxymethyl-2-phenyl-ethylamino)-purin-9-yl]-5-(3-ethyl-isoxazol-5-yl)-tetrahydro-furan-3,4-diol; 4-(2-{6-Amino-9-[5S-(3-ethyl-isoxazol-5-yl)-3R,4S-dihydroxy-tetrahydrofuran-2R-yl]-9H-purin-2-ylamino}-ethyl)-benzenesulfonamide; (2R,3R,4S,5S)-2-[2-(trans-4-Amino-cyclohexylamino)-6-(2,2-diphenyl-ethylamino)-purin-9-yl]-5-(3-ethyl-isoxazol-5-yl)-tetrahydro-furan-3,4-diol; (2S,3S,4R,5R)-2-(3-Ethyl-isoxazol-5-yl)-5-{6-(3-iodo-benzylamino)-2-[2-(1-methyl-1H-imidazol-4-yl)-ethylamino]-purin-9-yl}-tetrahydro-furan-3,4-diol; (2R,3R,4S,5S)-2-{6-(2-Cyclohexyl-ethylamino)-2-[2-(1-methyl-1H-imidazol-4-yl)-ethylamino]-purin-9-yl}-5-(3-ethyl-isoxazol-5-yl)-tetrahydro-furan-3,4-diol; (2R,3R,4S,5S)-2-[6-(2-Cyclohexyl-ethylamino)-2-(1S-hydroxymethyl-2-phenyl-ethylamino)-purin-9-yl]-5-(3-ethyl-isoxazol-5-yl)-tetrahydro-furan-3,4-diol; N-(2-{6-(2,2-Diphenyl-ethylamino)-9-[5S-(3-ethyl-isoxazol-5-yl)-3R,4S-dihydroxy-tetrahydro-furan-2R-yl]-9H-purin-2-ylamino}-ethyl)-guanidine; N-(4-{6-(2,2-Diphenyl-ethylamino)-9-[5S-(3-ethyl-isoxazol-5-yl)-3R,4S-dihydroxy-tetrahydro-furan-2R-yl]-9H-purin-2-ylamino}-cyclohexyl)-acetamide; 2-[9-[5S-(3-Ethyl-isoxazol-5-yl)-3R,4S-dihydroxy-tetrahydro-furan-2R-yl]-2-(2- guanidino-ethylamino)-9H-purin-6-ylamino]-ethanesulfonic acid methylamide; N-(2-{6-(1,1-Dioxo-hexahydro-1.lambda.6-thiopyran-4-ylamino)-9-[5S-(3-ethyl-isoxazol-5-yl)-3R,4S-dihydroxy-tetrahydro-furan-2R-yl]-9H-purin-2-ylamino}-ethyl)-guanidine; 2-[9-[5S-(3-Ethyl-isoxazol-5-yl)-3R,4S-dihydroxy-tetrahydro-furan-2R-yl]-2-(1S-hydroxymethyl- 2-phenyl-ethylamino)-9H-purin-6-ylamino]-ethanesulfonic acid methylamide; 1-{4-[9-[5S-(3-Ethyl-isoxazol-5-yl)-3R,4S-dihydroxy-tetrahydro-furan-2R-yl]-2-(1S-hydroxymethyl-2-phenyl-ethylamino)-9H-purin-6-ylamino]-piperidin-1-yl}-ethanone; 1-(4-{2-(trans-4-Amino-cyclohexylamino)-9-[5S-(3-ethyl-isoxazol-5-yl)-3R,4S-dihydroxy-tetrahydro-furan-2R-yl]-9H-purin-6-ylamino}-piperidin-1-yl)-ethanone; (2R,3R,4S,5S)-2-(3-Ethyl-isoxazol-5-yl)-5-[2-(2-pyridin-2-yl-ethylamino)-6-(tetrahydro-thiopyran-4-ylamino)-purin-9-yl]-tetrahydro-furan-3,4-diol; (2R,3R,4S,5S)-2-[6-(1,1-Dioxo-hexahydro-1.lambda.6-thiopyran-4-ylamino)-2-(2-piperidin-1-yl-ethylamino)-purin-9-yl]-5-(3-ethyl-isoxazol-5-yl)-tetrahydro-furan-3,4-diol; (2R,3R,4S,5S)-2-[2-(trans-4-Amino-cyclohexylamino)-6-(1,1-dioxo-hexahydro-1.lambda.6-thiopyran-4-ylamino)-purin-9-yl]-5-(3-ethyl-isoxazol-5-yl)-tetrahydro-furan-3,4-diol; N-(2-{6-(1-Acetyl-piperidin-4-ylamino)-9-[5S-(3-ethyl-isoxazol-5-yl)-3R,4S-dihydroxy-tetrahydro-furan-2R-yl]-9H-purin-2-ylamino}-ethyl)-guanidine; N-{2-[9-[5S-(3-ethyl-isoxazol-5-yl)-3R,4S-dihydroxy-tetrahydro-furan-2R-yl]-6-(piperidin-4-ylamino)-9H-purin-2-ylamino]-ethyl}-guanidine; (2S,3S,4R,5R)-2-(3-Ethyl-isoxazol-5-yl)-5-[2-(1S-hydroxymethyl-2-phenyl-ethylamino)-6-(tetrahydro-thiopyran-4-ylamino)-purin-9-yl]-tetrahydro-furan-3,4-diol; (2S,3S,4R,5R)-2-(3-ethyl-isoxazol-5-yl)-5-[2-(1S-hydroxymethyl-2-phenyl-ethylamino)-6-(1-oxo-hexahydro-1.lambda.4-thiopyran-4-ylamino)-purin-9-yl]-tetrahydro-furan-3,4-diol); (2S,3S,4R,5R)-2-(3-Ethyl-isoxazol-5-yl)-5-[6-(1-ethyl-propylamino)-2-(1S-hydroxymethyl-2-phenyl-ethylamino)-purin-9-yl]-tetrahydro-furan-3,4-diol; (2S,3S,4R,5R)-2-(3-Ethyl-isoxazol-5-yl)-5-[6-(1-ethyl-propylamino)-2-(pyrrolidin-3R-ylamino)-purin-9-yl]-tetrahydro-furan-3,4-diol; (2S,3S,4R,5R)-2-(3-Ethyl-isoxazol-5-yl)-5-[6-(1-ethyl-propylamino)-2-(2-pyridin-2-yl-ethylamino)-purin-9-yl]-tetrahydro-furan-3,4-diol; (2S,3S,4R,5R)-2-(3-Ethyl-isoxazol-5-yl)-5-[6-(1-ethyl-propylamino)-2-(2-morpholin-4-yl-ethylamino)-purin-9-yl]-tetrahydro-furan-3,4-diol; (2R,3R,4S,5S)-2-[2-(trans-4-Amino-cyclohexylamino)-6-(1-ethyl-propylamino)-purin-9-yl]-5-(3-ethyl-isoxazol-5-yl)-tetrahydro-furan-3,4-diol; N-{2-[9-[5S-(3-Ethyl-isoxazol-5-yl)-3R,4S-dihydroxy-tetrahydro-furan-2R-yl]-6-(1-ethyl-propylamino)-9H-purin-2-ylamino]-ethyl}-guanidine; (2R,3R,4S,5S)-2-[6-(3,3-Dimethyl-butylamino)-2-(2-piperidin-1-yl-ethylamino)-purin-9-yl]-5-(3-ethyl-isoxazol-5-yl)-tetrahydro-furan-3,4-diol; (2R,3R,4S,5S)-2-[6-(3,3-Dimethyl-butylamino)-2-(2-morpholin-4-yl-ethylamino)-purin-9-yl]-5-(3-ethyl-isoxazol-5-yl)-tetrahydro-furan-3,4-diol]; (2R,3R,4S,5S)-2-{6-Benzylamino-2-[2-(1-methyl-1H-imidazol-4-yl)-ethylamino]-purin-9-yl}-5-(3-ethyl-isoxazol-5-yl)-tetrahydro-furan-3,4-diol; (2R,3R,4S,5S)-2-[6-Benzylamino-2-(2-piperidin-1-yl-ethylamino)-purin-yl]-5-(3-ethyl-isoxazol-5-yl)-tetrahydro-furan-3,4-diol; (2S,3S,4R,5R)-2-(3-Ethyl-isoxazol-5-yl)-5-[6-(1S-hydroxymethyl-2-phenyl-ethylamino)-2-(2-piperidin-1-yl-ethylamino)-purin-9-yl]-tetrahydro-furan-3,4-diol; (2R,3R,4S,5S)-2-[2-(Cyclopentylamino)-6-(1-ethyl-propylamino)-purin-9-yl]-5-(3-ethyl-isoxazol-5-yl)-tetrahydro-furan-3,4-diol; (2R,3R,4S,5S)-2-[2-(3,4-Dimethoxyphenyl-ethylamino)-6-(1-ethyl-propylamino)-purin-9-yl]-5-(3-ethyl-isoxazol-5-yl)-tetrahydro-furan-3,4-diol; (2R,3R,4S,5S)-2-[2-(4-tetrahydropyranyl-amino)-6-(1-ethyl-propylamino)-purin-9-yl]-5-(3-ethyl-isoxazol-5-yl)-tetrahydro-furan-3,4-diol; (2R,3R,4S,5S)-2-[2-(1-Benzyl-pyrrolidin-3S-1-ylamino)-6-(1-ethyl-propylamino)-purin-9-yl]-5-(3-ethyl-isoxazol-5-yl)-tetrahydro-furan-3,4-diol; 5-(5R-{6-(1-Ethyl-propylamino)-2-[2-(1-methyl-1H-imidazol-4-yl)-ethylamino]-purin-9-yl}-3 S,4R-dihydroxy-tetrahydro-furan-2S-yl)-isoxazole-3-carbaldehyde oxime; (2S,3S,4R,5R)-2-(3-Ethyl-isoxazol-5-yl)-5-[6-(1S-hydroxymethyl-2-phenyl-ethylamino)-2-(2-morpholin-4-yl-ethylamino)-purin-9-yl]-tetrahydro-furan-3,4-diol; (2S,3S,4R,5R)-2-(3-Ethyl-isoxazol-5-yl)-5-[6-benzylamino-2-(2-pyridin-2-yl-ethylamino)-purin-9-yl]-tetrahydro-furan-3,4-diol; (2S,3S,4R,5R)-2-(3-Ethyl-isoxazol-5-yl)-5-{6-(1-ethyl-propylamino)-2-[2-(pyridin-2-ylamino)-ethylamino]-purin-9-yl}-tetrahydro-furan-3,4-diol; (2R,3R,4S,5S)-2-[6-(1-Ethyl-propylamino)-2-(2-piperidin-1-yl-ethylamino)-purin-9-yl]-5-[3-(1-hydroxy-ethyl)-isoxazol-5-yl]-tetrahydro-furan-3,4-diol; (2R,3R,4S,5S)-2-[6-(1-Ethyl-propylamino)-2-(2-piperidin-1-yl-ethylamino)-purin-9-yl]-5-(3-methyl-isoxazol-5-yl)-tetrahydro-furan-3,4-diol; (2R,3R,4S,5S)-2-[6-(1-Ethyl-propylamino)-2-(2-piperidin-1-yl-ethylamino)-purin-9-yl]-5-(3-propyl-isoxazol-5-yl)-tetrahydro-furan-3,4-diol; (2R,3R,4S,5S)-2-[6-(1-Ethyl-propylamino)-2-(2-piperidin-1-yl-ethylamino)-purin-9-yl]-5-(3-hydroxymethyl-isoxazol-5-yl)-tetrahydro-furan-3,4-diol; (2R,3R,4S,5S)-2-{6-(1-Ethyl-propylamino)-2-[2-(1-methyl-1H-imidazol-4-yl)-ethylamino]-purin-9-yl}-5-[3(1-hydroxy-ethyl)-isoxazol-5-yl]-tetrahydro-furan-3,4-diol; (2R,3R,4S,5S)-2-{6-(1-Ethyl-propylamino)-2-[2-(1-methyl-1H-imidazol-4-yl)-ethylamino]-purin-9-yl}-5-(3-methyl-isoxazol-5-yl)-tetrahydro-furan-3,4-diol; (2R,3R,4S,5S)-2-{6-(1-Ethyl-propylamino)-2-[2-(1-methyl-1H-imidazol-4-yl)-ethylamino]-purin-9-yl}-5-(3-propyl-isoxazol-5-yl)-tetrahydro-furan-3,4-diol; (2S,3S,4R,5R)-2-(3-Ethyl-isoxazol-5-yl)-5-{6-(1S-hydroxymethyl-2-phenyl-ethylamino)-2-[2-(pyridin-2-ylamino)-ethylamino]-purin-9-yl}-tetrahydro-furan-3,4-diol; (2S,3S,4R,5R)-2-(3-Ethyl-isoxazol-5-yl)-5-[6-(1S-hydroxymethyl-2-phenyl-ethylamino)-2-(2-pyrrolidin-1-yl-ethylamino)-purin-9-yl]-tetrahydro-furan-3,4-diol; (2R,3R,4S,5S)-2-[2-(2-Amino-ethylamino)-6-(1S-hydroxymethyl-2-phenyl-ethylamino)-purin-9-yl]-5-(3-ethyl-isoxazol-5-yl)-tetrahydro-furan-3,4-diol; (2S,3S,4R,5R)-2-(3-Ethyl-isoxazol-5-yl)-5-[6-(3-iodo-benzylamino)-2-(2-piperidin-1-yl-ethylamino)-purin-9-yl]-tetrahydro-furan-3,4-diol; (2R,3R,4S,5S)-2-[2-Ethylamino-6-(3-iodo-benzylamino)-purin-9-yl]-5-(3-ethyl-isoxazol-5-yl)-tetrahydro-furan-3,4-diol; (2S,3S,4R,5R)-2-(3-Bromo-isoxazol-5-yl)-5-[6-(1-ethyl-propylamino)-2-(2-piperidin-1-yl-ethylamino)-purin-9-yl]-tetrahydro-furan-3,4-diol; 5-(5R-{6-(1-Ethyl-propylamino)-2-[2-(1-methyl-1H-imidazol-4-yl)-ethylamino]-purin-9-yl}-3S,4R-dihydroxy-tetrahydro-furan-2S-yl)-isoxazole-3-carboxylic acid ethyl ester; (2S,3S,4R,5R)-2-(3-Ethyl-isoxazol-5-yl)-5-[6-(1S-hydroxymethyl-2-methyl-propylamino)-2-(2-pyrrolidin-1-yl-ethylamino)-purin-9-yl]-tetrahydro-furan-3,4-diol; (2S,3S,4R,5R)-2-(3-Ethyl-isoxazol-5-yl)-5-[6-(1S-hydroxymethyl-2-methyl-propylamino)-2-(2-piperidin-1-yl-ethylamino)-purin-9-yl]-tetrahydro-furan-3,4-diol; (2S,3S,4R,5R)-2-(3-Ethyl-isoxazol-5-yl)-5-{6-(1S-hydroxymethyl-2-methyl-propylamino)-2-[2-(pyridin-2-ylamino)ethylamino]-purin-9-yl}-tetrahydro-furan-3,4-diol; (2S,3S,4R,5R)-2-(3-Ethyl-isoxazol-5-yl)-5-{6-(1S-hydroxymethyl-2-methyl-propylamino)-2-(1S-hydroxymethyl-2-phenyl-ethylamino)-purin-9-yl}-tetrahydro-furan-3,4-diol; or a salt or solvate of any one thereof.

21. A pharmaceutical composition comprising a compound of formula (I) as defined in claim 1 or a pharmaceutically acceptable salt or solvate thereof in admixture with one or more physiologically acceptable diluents or carriers.

22. A pharmaceutically acceptable salt of a compound of formula (I) as defined in claim 1.

23. A process for preparation of a compound of formula (I) as defined in claim 1 which comprises:
(a) reacting a corresponding compound of formula (II)

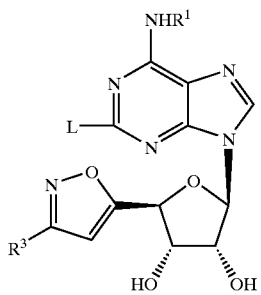

(II)

wherein $R^1$ is as defined in claim 1 and $R^3$ is as defined in claim 1 and L represents a leaving group, or a protected derivative thereof, with a compound of formula $R^2NH_2$ or a protected derivative thereof, wherein $R^2$ is as defined in claim 1;

(b) reacting a corresponding compound of formula (III)

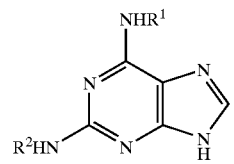

(III)

wherein $R^1$ is as defined in claim 1 and $R^2$ is as defined in claim 1, with a compound of formula (IV)

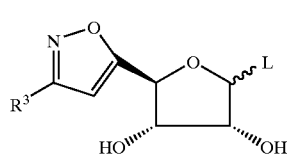

(IV)

wherein $R^3$ is as defined in claim 1 and L represents a leaving group or a protected derivative thereof;

(c) converting one compound of formula (I) to another compound of formula (I); or (d) deprotecting a compound of formula (I) which is protected;

and where desired or necessary converting a compound of formula (I) or a salt thereof into another salt thereof.

24. A process for preparation of a compound of formula (I) as defined in claim 1 which comprises reacting a corresponding compound of formula (IIa):

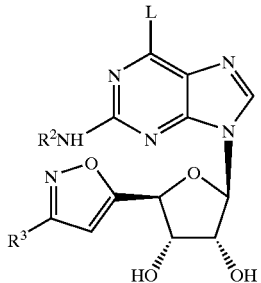

(IIa)

wherein $R^2$ is as defined in claim 1 and $R^3$ is as defined in claim 1 and L represents a leaving group or a protected derivative thereof, with a compound of formula $R^1NH_2$ or a protected derivative thereof, wherein $R^1$ is as defined in claim 1.

25. A compound of formula (II)

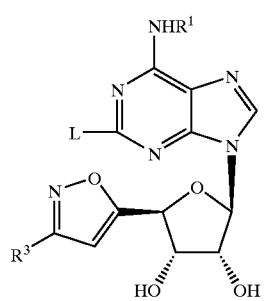

(II)

wherein $R^1$ is as defined in claim 1 and $R^3$ is as defined in claim 1 and L represents a leaving group, or a protected derivative thereof.

26. A compound of formula (IIa)

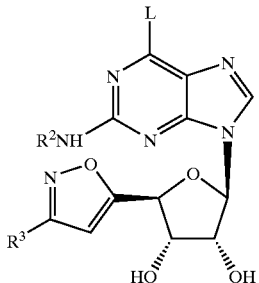

(IIa)

wherein $R^2$ is as defined in claim 1 and $R^3$ is as defined in claim 1 and L represents a leaving group, or a protected derivative thereof.

27. A compound of formula (IV)

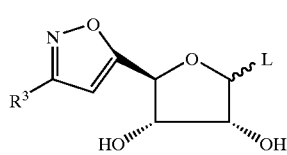

(IV)

wherein $R^3$ is as defined in claim 1 and L represents a leaving group or a protected derivative thereof.

28. A compound of formula (V)

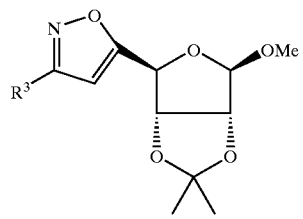

(VI)

wherein $R^3$ is as defined in claim 1.

29. A compound of formula (V)

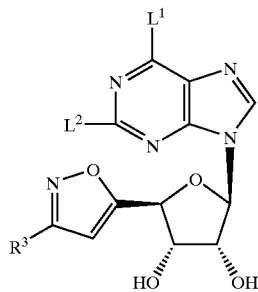

wherein R³ is as defined in claim 1 and L¹ and L² independently represent a leaving group, or a protected derivative thereof.

30. A compound of formula (VIII)¹

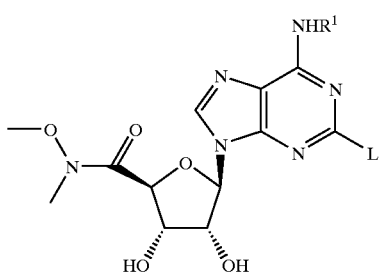

wherein R¹ is as defined in claim 1 and L is a leaving group or a protected derivative thereof.

31. A compound of formula (IX)¹

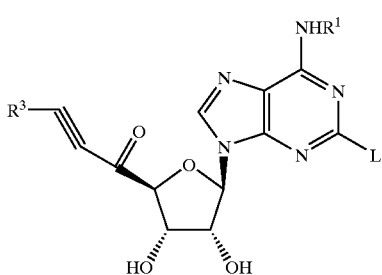

wherein R¹ is as defined in claim 1 and R³ is as defined in claim 1 and L is a leaving group or a protected derivative thereof.

32. A compound of formula (X)¹

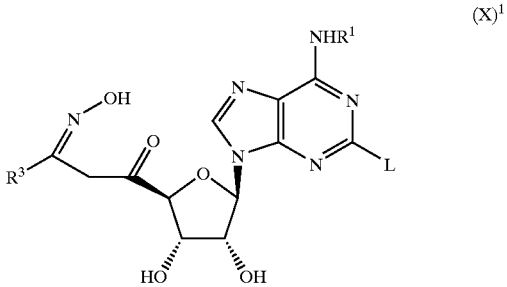

wherein R¹ is as defined in claim 1 and R³ is as defined in claim 1 and L is a leaving group or a protected derivative thereof.

33. A pharmaceutical composition comprising a compound of formula (I) as defined in claim 16 or a pharmaceutically acceptable salt or solvate thereof in admixture with one or more physiologically acceptable diluents or carriers.

34. A pharmaceutical composition comprising a compound of formula (I) as defined in claim 18 or a pharmaceutically acceptable salt or solvate thereof in admixture with one or more physiologically acceptable diluents or carriers.

35. A method of treatment or of inflammatory diseases which comprises administering to a patient an effective amount of a compound of formula (I) as defined in claim 16 or a pharmaceutically acceptable salt or solvate thereof.

36. A method of treatment of inflammatory diseases which comprises administering to a patient an effective amount of a compound of formula (I) as defined in claim 18 or a pharmaceutically acceptable salt or solvate thereof.

* * * * *